United States Patent
Poirier et al.

(10) Patent No.: US 9,708,305 B2
(45) Date of Patent: Jul. 18, 2017

(54) SUBSTITUTED 1,2,3,4-TETRAHYDROISOQUINOLINE DERIVATIVES FOR THE TREATMENT OF HORMONE-DEPENDENT DISEASES

(71) Applicant: UNIVERSITÉ LAVAL, Québec (CA)

(72) Inventors: Donald Poirier, L'Ancienne Lorette (CA); René Maltais, Québec (CA)

(73) Assignee: UNIVERSITÉ LAVAL, Québec (CA)

( * ) Notice: Subject to any disclaimer, the term of this patent is extended or adjusted under 35 U.S.C. 154(b) by 0 days.

(21) Appl. No.: 14/912,709

(22) PCT Filed: Aug. 1, 2014

(86) PCT No.: PCT/CA2014/050728
§ 371 (c)(1),
(2) Date: Feb. 18, 2016

(87) PCT Pub. No.: WO2015/024111
PCT Pub. Date: Feb. 26, 2015

(65) Prior Publication Data
US 2016/0200685 A1 Jul. 14, 2016

Related U.S. Application Data

(60) Provisional application No. 61/868,177, filed on Aug. 21, 2013.

(51) Int. Cl.
C07D 217/04 (2006.01)
C07D 217/06 (2006.01)
C07D 217/08 (2006.01)
C07D 401/10 (2006.01)
C07D 401/12 (2006.01)
C07D 401/14 (2006.01)
A61K 31/472 (2006.01)
(Continued)

(52) U.S. Cl.
CPC .......... *C07D 409/14* (2013.01); *A61K 31/472* (2013.01); *A61K 31/4725* (2013.01); *A61K 31/496* (2013.01); *A61K 31/506* (2013.01); *A61K 31/5377* (2013.01); *A61K 31/541* (2013.01); *A61K 45/06* (2013.01); *C07D 217/04* (2013.01); *C07D 217/06* (2013.01); *C07D 217/08* (2013.01); *C07D 401/10* (2013.01); *C07D 401/12* (2013.01); *C07D 401/14* (2013.01); *C07D 405/12* (2013.01); *C07D 405/14* (2013.01)

(58) Field of Classification Search
CPC .. C07D 217/04; C07D 217/06; C07D 217/08; C07D 401/10; C07D 401/12; C07D 401/14; A61K 31/472; A61K 31/4725
See application file for complete search history.

(56) References Cited

U.S. PATENT DOCUMENTS 7,601,739 B2 † 10/2009 Danso-Danquah

FOREIGN PATENT DOCUMENTS

WO 0246164 A1 6/2002

OTHER PUBLICATIONS

Agnusdei D., Iori N. Raloxifene: results from the MORE study. J. Musculoskel. Neuron Interact. 2000, 1, 127-132.
Boivin R.P., Luu-The V., Lachance R., Labrie F., Poirier D. Structure-activity relationship of 17alpha-derivatives of estradiol as inhibitors of steroid sulfatase. J. Med. Chem. 2000, 43, 4465-4478.
Bonkhoff H., Berges R. The Evolving Role of Oestrogens and Their Receptors in the Development and Progression of Prostate Cancer. Eur. Urol. 2009, 55, 533-542.
Brawer M.K. Hormonal Therapy for Prostate Cancer. Review in Urol. 2006, 8, suppl.2: S35-S47.
Bbriganti A. Oestrogens and Prostate Cancer: Novel Concepts About an Old Issue. Eur. Urol. 2009, 55, 543-545.
(Continued)

*Primary Examiner* — Kahsay Habte
(74) *Attorney, Agent, or Firm* — Beatrice Ngatcha

(57) ABSTRACT

Provided are compounds of general formula A and A', wherein $X_1$ and $X_2$ are each C, CH or N; $R_3$ and $R_4$ are each H, optionally substituted $C_1$-$C_{30}$ saturated or unsaturated chemical group, or together form an optionally substituted $C_5$-$C_8$ cycle; $Z_1$; $Z_2$ and $Z_3$ are each N or CH; V is C=O, C=S or $CH_2$; n is from 1 to 12; $W_1$ and $W_2$ are each H, $CH_2$, O or S; and $R_1$ and $R_2$ are each H, $C_1C_6$ alkyl, $C_1C_6$ aryl, $C_1C_{12}$ alkylaryl, optionally substituted phenyl, $C_1C_6$ alkoxy, $C_1C_6$ thioalkoxy, F, Cl, Br or I. These compounds inhibit steroid sulfatase (STS), act as selective estrogen receptor modulators (SERMs), increase alkaline phosphatase (ALP) activity, and are useful in the treatment of medical conditions involving hormones such as breast cancer, prostate cancer, endometriosis, osteoporosis, benign prostatic hyperplasia and endometrial cancer.

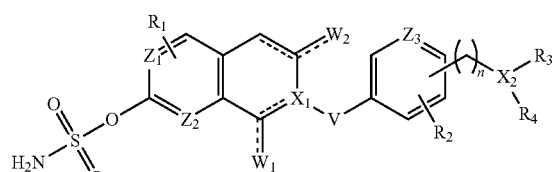

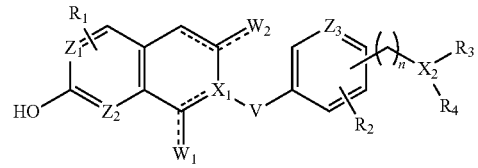

14 Claims, 14 Drawing Sheets

(51) Int. Cl.

| | |
|---|---|
| A61K 31/4725 | (2006.01) |
| C07D 409/14 | (2006.01) |
| A61K 31/496 | (2006.01) |
| A61K 31/506 | (2006.01) |
| A61K 31/5377 | (2006.01) |
| A61K 31/541 | (2006.01) |
| C07D 405/14 | (2006.01) |
| C07D 405/12 | (2006.01) |
| A61K 45/06 | (2006.01) |

(56) References Cited

OTHER PUBLICATIONS

Brooks S.C., Locke E.R., Soule H.D. Estrogen Receptor in a Human Cell Line (MCF-7) from Breast Carcinoma. J. Biol. Chem., 1973, 248, 6251-6253.

Byers M., Kuiper G.G.J.M., Gustafsson J.A., Parke-Sarge O.K. Estrogen Receptor-beta mRNA Expression in Rat Ovary: Down-Regulation by Gonadotropins. Mol. Endocrinology 1997, 11, 172 182.

Campos S.M. Aromatase Inhibitors for Breast Cancer in Postmenopausal Women. The Oncologist 2004, 9, 126-136.

Chetrite G.S., Cortes-Prieto J., Philippe J.C., Wright F., Pasqualini J.R. Comparison of estrogen concentrations, estrone sulfatase and aromatase activities in normal, and in cancerous, human breast tissues. J. Steroid Biochem. Mol. Biol. 2000, 72, 23-27.

Ciobanu L.C., Boivin R.P., Luu-The V., Labrie F., Poirier D. Potent inhibition of steroid sulfatase activity by 3-O-sulfamate 17alpha-benzyl(or 4'-tert-butylbenzyl)estra-1,3,5(10)-trienes: combination of two substituents at positions C3 and C17alpha of estradiol. J. Med. Chem. 1999, 42, 2280-2286.

Ciobanu L.C., Maltais R., Poirier D. The sulfamate functional group as a new anchor for solid-phase organic synthesis. Org. Lett. 2000, 2, 445-448.

Ciobanu L.C., Luu-The V., Poirier D. Nonsteroidal compounds designed to mimic potent steroid sulfatase Inhibitors. J. Steroid Biochem. Mol. Biol. 2002, 80, 339-353.

Ciobanu L.C., Boivin R. P., Luu-The V., Poirier D. 3beta-Sulfamate derivatives of C19 and C21 steroids bearing a t-butylbenzyl or a benzyl group: synthesis and evaluation as non-estrogenic and non-androgenic steroid sulfatase Inhibitors. J. Enzyme Inhib. Med. Chem. 2003, 18, 15-26.

Ciobanu L.C., Luu-The V., Martel C., Labrie F., Poirier D., Inhibition of Estrone Sulfate-induced Uterine Growth by Potent Nonestrogenic Steroidal Inhibitors of Steroid Sulfatase. Cancer Res., 2003, 63, 6442-6446.

Ciobanu L.C., Poirier D. Synthesis of libraries of 16beta-aminopropyl estradiol derivatives for targeting two key steroidogenic enzymes. ChemMedChem. 2006, 1, 1249 1259.

Colette S., Defrére S., Lousse J.C., Langendonckt A.V., Gotteland J.P., Loumaye E., Donnez J. Inhibition of steroid sulfatase decreases endometriosis in a in vivo murine model. Hum. Reprod. 2011, 26, 1362-1370.

Compton D.R., Sheng S., Carlson K.E., Rebacz N.A., Lee I.Y., Katzenellenbogen B.S., Katzenellenbogen J.A. Pyrazolo[1,5-alpha]pyrimidines: estrogen receptor ligands possessing estrogen receptor beta antagonist activity. J. Med. Chem. 2004, 47, 5872-5893.

De Bono J.S., Logothetis C.J., Molina A., et al Abiraterone and Increased Survival in Metastatic Prostate Cancer. New Engl. J. Med. 2011, 364, 1995-2005.

Duggan C., Marriott K., Edwards R., Cuzick J. Inherited and acquired risk factors for venous thromboembolic disease among women taking tamoxifen to prevent breast cancer. J. Clin. Oncol. 2003, 21, 3588-3593.

Ghosh D. Human sulfatases: a structural perspective to catalysis. Cell Mol. Life Sci. 2007, 64, 2013-2022.

Gianni, W., Ricci, A., Gazzaniga, P., Brama, M., Pietropaolo, M., Votano, S., Patane, F., Agliano, A. M., Spera, G., Marigliacno, V., Ammendola, S., Agnusdei, D., Migliaccio, S. Scandurra, R. Raloxifene Modulates Interleukin-6 and Tumor Necrosis Factor-alpha Synthesis in Vivo : Results from a Pilot Clinical Study. J. Clin. Endocrinol. Metab. 2004, 89, 6097-6099.

Giton F., De La Taille A., Allory Y., Galons, H., Vacherot, F., Soyeux, P. Abbou, C.C., Loric, S., Cussenot, O., Raynaud, J.P., Fiet, J. Estrone sulfate (E1S), a prognosis marker for tumor aggressiveness in prostate cancer (PCa). J. Steroid Biochem. Mol. Biol. 2008, 109, 158-167.

Harkonen P.L., Makela S.I. Role of estrogens in development of prostate cancer. J. Steroid Biochem. Mol. Biol. 2004, 92, 297-305.

Hernandez-Guzman F.G., Higashiyama T., Pangborn W., Osawa Y. Ghosh D. Structure of human estrone sulfatase suggests functional roles of membrane association. J. Biol. Chem. 2003, 278, 22989-22997.

Ho S.M. Estrogens and anti-estrogens: Key mediators of prostate carcinogenesis and new therapeutic candidates. J. Cell. Biochem. 2004, 91, 491-503.

Hobisch A., Hittmair A., Daxenbichler G., Wille, S., Radmayr, C., Hobisch-Hagen, P., Bartsch, G., Klocker, H. Culig, Z. Metastatic lesions from prostate cancer do not express oestrogen and progesterone receptors. J. Pathology 1997, 182, 356-361.

Huggins C., Hodges C.V. Studies on Prostatic Cancer. I. The Effect of Castration, of Estrogen and of Androgen Injection on Serum Phosphatases in Metastatic Carcinoma of the Prostate. Cancer Res. 1941, 1, 293-297.

Imai Y., Nakamura T., Matsumoto T., Takaoka K., Kato S. Molecular mechanisms underlying the effects of sex steroids on bone and mineral metabolism. J. Bone Miner. Metab. 2009, 27, 127-130.

Jeng, M.H., Jiang, S.Y., Jordan, V.C. Paradoxical regulation of estrogen-dependent growth factor gene expression in estrogen receptor (ER)-negative human breast cancer cells stably expressing ER. Cancer Letters. 1994, 82, 123-128.

Jonat W., Pritchard K.I., Sainsbury R., Klijn J.G. Trends in endocrine therapy and chemotherapy for early breast cancer: a focus on the premenopausal patient J. Cancer Res. Clin. Oncol. 2006, 132, 275-286.

Kawashima H., Nakatani T. Involvement of estrogen receptors in prostatic diseases. Int. J. Urol. 2012, 19, 512-522.

Labrie F., Dupont A., Bélanger A. (1985) In: Important Advances in Oncology (De Vita V.T., Hellman S., Rosenberg S.A., eds), J.B. Lippincott, Philadelphia, pp. 193.

Labrie F. Intracrinology. Mol. Cell. Endocrinol. 1991, 78, C113-118.

Labrie F., Cusan L., Gomez J.L., Diamond, P., Suburu, R., Lemay, M., Tetu, B., Fradet, Y. Candas, B. Down-staging of early stage prostate cancer before radical prostatectomy: The first randomized trial of neoadjuvant combination therapy with flutamide and a luteinizing hormone-releasing hormone agonist. Urology 1994, 44, 29-37.

Labrie F., Belanger A., Simard J. Luu-The V., Labrie C. Dhea and Peripheral Androgen and Estrogen Formation: Intracrinology. N.Y. Academy of Sciences 1995, 774, 16-28.

Labrie F., Luu-The V., Labrie C., Belanger, A., Simard, J., Lin, S.X., Pelletier, G. Endocrine and Intracrine Sources of Androgens in Women: Inhibition of Breast Cancer and Other Roles of Androgens and Their Precursor Dehydroepiandrosterone. Endocr. Rev. 2003, 24, 152-182.

Lam H.Y.P. Tamoxifen is a calmodulin antagonist in the activation of cAMP phosphodiesterase. Biochem. Biophys. Res. Comm. 1984, 118, 27-32.

Laplante Y., Cadot C., Fournier M.A., Poirier D. Estradiol and estrone C-16 derivatives as inhibitors of type 1 17beta-hydroxysteroid dehydrogenase: blocking of ER+ breast cancer cell proliferation induced by estrone. Bioorg. Med. Chem., 2008, 16, 1849-1860.

Lau K.M., Laspina M., Long J., Ho, S.M. Expression of Estrogen Receptor (ER)-alpha and ER-beta in Normal and Malignant Prostatic Epithelial Cells: Regulation by Methylation and Involvement in Growth Regulation. Cancer Res. 2000, 60, 3175-3182.

(56) References Cited

OTHER PUBLICATIONS

Leuprolide Study Group. Leuprolide versus diethylstilbestrol for metastatic prostate cancer. New Engl. J. Med. 1984, 311, 1281-1286.
Lin S.X., Chen J., Mazumdar M., Poirier D., Wang C., Azzi A., Zhou M. Molecular therapy of breast cancer: progress and future directions. Nat. Rev. Endocrinol. 2010, 6, 485-493.
Maltais R., Poirier D. Steroid sulfatase inhibitors: a review covering the promising 2000-2010 decade. Steroids. 2011, 76, 929-948.
McDonnell D.P., Wardell S. E. The molecular mechanisms underlying the pharmacological actions of ER modulators: implications for new drug discovery in breast cancer. Curr. Opin. Pharmacol. 2010, 10, 620-628.
Miki Y., Suzuki T., Hatori M., Igarashi K, Aisaki K.I., Kanno J., Nakamura Y., Uzuki M., Sawai T, Sasano H. Effects of aromatase inhibitors on human osteoblast and osteoblast-like cells: a possible androgenic bone protective effects induced by exemestane. Bone, 2007, 40, 876-887.
Mosselman S., Polman J., Dijkema R. ERbeta: Identification and characterization of a novel human estrogen receptor FEBS Lett. 1996, 392, 49-53.
Musa M.A., Omar M., Khan F., Cooperwood J.S. Medicinal chemistry and emerging strategies applied to the development of selective estrogen receptor modulators (SERMs). Curr. Med. Chem. 2007, 14, 1249-1261.
Nelles J.L., Hu W.Y., Prins G.S. Estrogen action and prostate cancer. Expert Rev. Endocrionol. Metab. 2011, 6, 437-451.
Nicholson R.I., Walker K.J., Turkes, A., Turkes, O., Dyas, J., Blamey, R.W, Campbell, F.C., Robinson, M.R.G. Griffiths, K. Therapeutic significance and the mechanism of action of the LH-RH agonist ICI 118630 in breast and prostate cancer. J. Steroid Biochem. 1984, 20, 129-135.
Nunez-Nateras R., Castle E.P. Effect of the simultaneous blockade of androgen and estrogen receptors on prostate cancer Preliminary results. J. Clin. Oncol. 2011, 29, suppl 7: abstr 168.
O'Brian C.A., Liskamp R.M., Solomon D.H., Weinstein, B.I. Inhibition of Protein Kinase C by Tamoxifen. Cancer Res. 1985, 45, 2462-2465.
Obiorah I., Jordan, V.C. Progress in endocrine approaches to the treatment and prevention of breast cancer. Maturitas. 2011, 70, 315-321.
Orimo H. The mechanism of mineralization and the role of alkaline phosphatase in health and disease. J. Nippon Med. Sch. 2010, 77, 4-12.
Ouellet E., Maltais R., Ouellet C., Poirier D. Investigation of a tetrahydroisoquinoline scaffold as dual-action steroid sulfatase inhibitors generated by parallel solid-phase synthesis. Med. Chem. Commun. 2013, 4, 681-692.
Parenti G., Meroni G., Ballabio A. The sulfatase gene family. Curr. Opin. Gen. Develop. 1997, 7, 386-391.
Pasqualini J.R., Gelly C., Nguyen B.-L., Vella C. Importance of estrogen sulfates in breast cancer. J. Steroid Biochem. 1989, 34, 155-163.
Pasqualini J.R., Chetrite G., Blacker C., Feinstein M.-C., Delalonde L., Talbi M., Maloche C. Concentration of estrone, estradiol, and estrone sulfate and evaluation of sulfatase and aromatase activities in pre- and post-menopausal breast cancer patients. J. Clin. Endocrinol. Metab. 1996, 81, 1460-1464.
Peterson E.M., Brownell J, Vince R. Synthesis and biological evaluation of 5'-sulfamoylated purinyl carbocyclic nucleosides. J. Med. Chem., 1992, 35, 3991-4000.
Pickar J.H., MacNeil T., Ohleth K. SERMs: Progress and future perspectives. Maturitas 2010, 67, 129-138.
Poirier D., Ciobanu L.C., Berube M. A multidetachable sulfamate linker successfully used in a solid-phase strategy to generate libraries of sulfamate and phenol derivatives. Bioorg. Med. Chem. Lett. 2002, 12, 2833-2838.
Poirier D., Roy J., Lefebvre J., Maltais R. (2011) A potent steroid sulfatase inhibitor blocks the DHEAS-stimulated growth of androgen-sensitive tissues and human prostate cancer xenografts (LNCaP cells) in nude mice. Congress on Steroid Research. Chicago MI, Mar. 27-29.p. 2-46.
Price D., Stein B., Sieber P., Tutrone R. Bailen J., Goluboff, E, Burzon D., Bostwick D., Steiner M. Toremifene for the Prevention of Prostate Cancer in Men With High Grade Prostatic Intraepithelial Neoplasia: Results of a Double-Blind, Placebo Controlled, Phase IIB Clinical Trial. J. Urol. 2006, 176, 965-970.
Purohit A., Dauvois S., Parker M.G., Potter B.V.L., Williams G.J. Reed M.J. The hydrolysis of oestrone sulphate and dehydroepiandrosterone sulphate by human steroid sulphatase expressed in transfected COS-1 cells. J. Steroid Biochem. Molec. Biol. 1994, 50, 101-104.
Purohit A., Foster P.A. Steroid sulfatase inhibitors for estrogen- and androgen-dependent cancers. J. Endocrinol. 2012, 212, 99-110.
Qu Q., Perala-Heape M., Kapanen A., Dahllund J., Salo J., Vaananen H.K., Harkonen P. Estrogen enhances differentiation of osteoblasts in mouse bone marrow culture. Bone. 1998, 22, 201-209.
Rasmussen G.H. Chapter 18. Chemical Control of Androgen Action. Ann. Rep. Med. Chem. 1986, 21, 179-188.
Rohlff C., Blagosklonny M.V., Kyle E., Kesari A., Kim I.Y., Zelner D.J., Hakim F., Trepel, J. Bergan, R.C. Prostate cancer cell growth inhibition by tamoxifen is associated with inhibition of protein kinase C and induction of p21(waf1/cip1). Prostate 1998, 37, 51-59.
Roy J., Lefebvre J., Maltais R., Poirier D. Inhibition of dehydroepiandrosterone sulfate action in androgen-sensitive tissues by EM-1913, an inhibitor of steroid sulfatase. Mol. Cell. Endocrinol. 2013, 376, 148-155.
Royuela M., De Miguel M.P., Bethencourt F.R., Sanchez-Chapado, M., Fraile, B., Arenas, M.I, Paniagua R. Estrogen receptors alpha and beta in the normal, hyperplastic and carcinomatous human prostate. J. Endocrinol. 2001, 168, 447 454.
Rozhin J., Corombos, J.D., Horwitz, J.P., Brooks, S.C. Endocrin steroid sulfotransferases: Steroid alcohol sulfotransferaxe from human breast carcinoma cell line MCF-7. J. Steroid Biochem. 1986, 25, 973-979.
Saito T., Yoshizawa M., Yamauchi Y., Kinoshita S., Fujii T., Mieda M., Sone H., Yamamoto Y., Koizumi N. Effects of the novel orally active antiestrogen TZE-5323 on experimental endometriosis. Arzneimittelforschung. 2003, 53, 507-514.
Santner S.J., Feil P.D., Santen R.J. In situ estrogen production via the estrone sulfatase pathway in breast tumors: relative importance versus the aromatase pathway. J. Clin. Endocrinol. Metab. 1984, 59, 29-33.
Setlur S.R., Mertz K.D., Hoshida Y. et al. Estrogen-Dependent Signaling in a Molecularly Distinct Subclass of Aggressive Prostate Cancer. J. Natl. Cancer Inst. 2008, 100, 815-825.
Smith M.R., Morton R.A., Barnette K.G., Sieber P.R., Malkowicz S.B., Rodriguez D., Hancock M.L., Steiner M.S. Toremifene to Reduce Fracture Risk in Men Receiving Androgen Deprivation Therapy for Prostate Cancer. J. Urol. 2010, 184, 1316-1321.
Stein C., Hille A., Seidel J., Rijnbout S., Waheed A., Schmidt B., Geuze, H. Von Figura K. Cloning and expression of human steroid-sulfatase. Membrane topology, glycosylation, and subcellular distribution in BHK-21 cells. J. Biol. Chem. 1989, 264, 13865-13872.
Steiner M.S. Role of peptide growth factors in the prostate: a review. Urology 1993, 42, 99-110.
Steiner M.S. Review of Peptide Growth Factors in Benign Prostatic Hyperplasia and Urological Malignancy. J. Urol. 1995, 153, 1085-1096.
Steiner M.S., Raghow, S. Neubaeur B.L. Selective estrogen receptor modulators fort the chemoprevention of prostate cancer. Urology. 2001, 57 (Suppl 4A) 68-72.
Steiner M.S., Raghow S. Antiestrogens and selective estrogen receptor modulators reduce prostate cancer risk. World J. Urol. 2003, 21, 31-36.
Subramanian A., Salhab M., Mokbel K. Oestrogen producing enzymes and mammary carcinogenesis: a review. Breast Cancer Res. Treat. 2008, 111, 191-202.
Sun J., Huang Y.R., Harrington W.R., Sheng S., Katzenellenbogen J.A., Katzenellenbogen B.S. Antagonists selective for estrogen receptor alpha. Endocrinology. 2002, 143, 941-947.

(56) References Cited

OTHER PUBLICATIONS

Suzuki T., Moriya T., Ishida T., Ohuchi N., Sasano H. Intracrine mechanism of estrogen synthesis in breast cancer. Biomed. Pharmacother. 2003, 57, 460-462.
Taneja S.S., Smith M.R., Dalton J.T., Raghow, S., Barnette, G., Steiner. M., Veverka, K.A. Toremifene—a promising therapy for the prevention of prostate cancer and complications of androgen deprivation therapy. Expert Opin. Investig. Drugs 2006, 15, 293-305.
Tripathi R.P., Verma S.S., Pandey J., Tiwari V.K. Recent development on catalytic reductive amination and applications. Curr. Org. Chem. 2008, 12, 1093-1115.
Wakeling A.E., Bowler J. Novel antiestrogens without partial agonist activity. J. Steroid Biochem. 1988, 31, 645-653.
Wang T., You Q., Huang F.S., Xiang H. Recent advances in selective estrogen receptor modulators for breast cancer Mini Rev. Med. Chem. 2009, 9, 1191-1201.
Wirth M., Froehner M., A review of studies of hormonal adjuvant therapy in prostate cancer. Eur. Urol. 1999, 36 (suppl 2), 14-19.
International Search Report and Written Opinion, Nov. 5, 2014.
CAS Registry No. 1184430-24-7, Sep. 15, 2009.
CAS Registry No. 1506657-69-7, Dec. 30, 2013.
Ouellet, Étienne, et al. "Investigation of a tetrahydroisoquinoline scaffold as dual-action steroid sulfatase inhibitors generated by parallel solid-phase synthesis." MedChemComm 4.4 (2013): 681-692.†

† cited by third party

A

B

A

B

A

B

SUBSTITUTED 1,2,3,4-TETRAHYDROISOQUINOLINE DERIVATIVES FOR THE TREATMENT OF HORMONE-DEPENDENT DISEASES

CROSS-REFERENCE TO RELATED APPLICATIONS

This application is a National Entry Application of PCT application no PCT/CA2014/050728 filed on Aug. 1, 2014 and published in English under PCT Article 21(2), which itself claims benefit of U.S. provisional application Ser. No. 61/868,177, filed on Aug. 21, 2013. All documents above are incorporated herein in their entirety by reference.

FIELD OF THE INVENTION

The invention relates generally to compounds for the treatment of medical conditions involving hormones. More specifically, the invention relates to compounds, their preparation and their use in the treatment of hormone-dependent diseases including hormone-dependent cancers. A compound of the invention presents more than one biological activity.

BACKGROUND OF THE INVENTION

Hormonal therapy is currently used for the treatment of estrogen-sensitive breast cancers. As the majority of breast cancers are initially estrogen-dependent, with approximately 55% in premenopausal women and 75% in post-menopausal women, this therapy efficiently blocks the stimulating effect of estrogens in breast cancer cells.[1] Selective estrogen receptor modulator (SERM) compounds, such as tamoxifen and raloxifene, are presently used to treat breast cancer.[2] In breast tissues, SERMs effectively block the activation of estrogen receptor alpha (ERα) by endogenous ligands and prevent the transcription of genes mediated by estrogen response elements (EREs).[3] This class of compounds possesses the particularity of having tissue specific effects on ERα, resulting in antagonist activity in breast and uterus tissues and agonist activity in bone tissues. Although tamoxifen and raloxifene possess the desired SERM activity, they also increase the risk of venous thromboembolism.[4,5] There remains a need for SERM compounds which exhibit fewer side effects.[6]

Inhibition of steroid sulfatase (STS) is a therapeutic approach for the treatment of estrogen-dependent breast cancers. In this regard, various types of STS inhibitors have been developed during the past years.[7-9] STS is an enzyme that converts inactive sulfated steroids, mainly pregnenolone sulfate (PREGS), estrone sulfate (E1S) and dehydroepiandrosterone sulfate (DHEAS), into unconjugated hormones. This is outlined in FIG. 1.[10] E1S and DHEAS are particularly abundant in circulation and act as reservoir of steroid precursors.[11] It is also known that STS activity in breast cancer tumors is much higher than aromatase, activity and that in situ formation of estrone (E1) and estradiol (E2) is mainly done via the STS pathway rather than the aromatase pathway.[12-14] Therefore blocking STS could prevent estrogen-sensitive carcinomas from transforming sulfated steroids into potent estrogens, mainly estrone (E1), estradiol (E2) and 5-androstenediol (5-diol).

The dual blockade of ERα and STS to reach a maximum estrogen blockade for the treatment of estrogen receptor-positive (ER+) breast cancers represents an interesting therapeutic approach. However, the maximum estrogen blockade obtained by this approach induces an estrogen depletion condition that could provoke undesirable side effects such as osteoporosis.[15]

An approach investigated in our laboratory relates to the design and development of dual-action compounds, i.e., compounds that are inhibitors of STS and that also possess estrogen modulator activity. More specifically, our approach aims at developing a non-steroidal sulfamoylated inhibitor of the enzyme STS that also possesses, among others, a selective estrogen receptor modulator (SERM) activity such as to attenuate a potential problem related to estrogen depletion induced by the inhibition of STS.[16]

There is a need for compounds that are inhibitors of STS and that also possess SERM capacity. Advantageously, such compounds may also present other biological activities of interest. For example, such compounds may have the ability to increase alkaline phosphate (ALP) activity.

Turning to androgen-dependent cancers such as prostate cancer:

Steroid Sulfatase (STS) and Prostate Cancer

Steroid hormones play an important role in the growth of androgen-sensitive cancers.[17,18] This type of cancer represents approximately 30% of all cancers in men in Canada.[19] The blockade of the action of the active steroids on the androgen receptor has allowed for the development of new therapies. The use of these therapies which are more specific and generally better tolerated than chemotherapy, has led to interesting results in the treatment of prostate cancer (use of an antiandrogen with a lutheinizing hormone releasing hormone (LHRH) agonist).[20,21] For an optimal use of this approach, it is important to completely block hormonal stimulation such as to avoid any subsequent recovery in the growth of tumors. Until now, it has merely been a partial blockade of hormone action, which has not allowed for a full exploitation of this approach. Indeed, the competitive blockade of hormone receptors by a pure antihormone is not optimal, since it can cause the accumulation of active steroids that compete for the binding to the receptor, thereby reducing the effectiveness of the blockade. In addition, we must take into account the ability of peripheral tissues to synthesize in large quantities, the active hormones from dehydroepiandrosterone sulfate (DHEAS) and also the ability of tumors to synthesize de novo active androgens.[22] It is increasingly evident that a maximum blockade of the hormonal action will be ultimately reached by the combined effect of antihormone (receptor blockade) and an effective enzyme inhibitor (blocking of steroidogenesis).

Removal of endocrine glands responsible for steroidogenesis has been and is still regarded as a way of blocking the production of steroid hormones. This surgical approach has however the disadvantage of being an irreversible process that is not without side effects for the patient physically and psychologically. For this reason, the development of medical strategies that are reversible was encouraged, particularly chemical blocking. The strategy used to produce a chemical or medical castration is to block the release of gonadotropins by the pituitary gland, and thus stop the formation of steroidal hormones.[23,24] Although chemical castration is effective, it still leaves significant portion of residual steroids of adrenal origin. In addition, since the affinity of antiandrogens used to block the androgen receptor is quite low, receptor blockade is not complete. Other means should be considered that completely eliminate the production of steroid hormones involved in the stimulation of hormone-sensitive cancers. Selective blocking of an enzyme involved in steroidogenesis is an interesting approach as it would then be possible to block the formation of a class of hormones produced locally by intracrinology without harming others, resulting in reduced side effects for the patient. This approach, which consists of blocking the biosynthesis of active steroids, has been successful for the treatment of advanced prostate cancers—an inhibitor of CYP17A1 (17α-hydroxylase/17,20-lyase) such as abiraterone acetate was used.[25]

Steroid sulfatase (STS) is also a key enzyme in the androgen biosynthesis, accordingly also represents a target. Sulfatases are a group of enzymes that catalyze the conversion of sulfate compounds ($R-OSO_3H$) into corresponding unconjugated compounds ($R-OH$).[26] Nine members of the large family of sulfatases have been isolated from humans and their corresponding gene identified.[27] Of these families, STS catalyzes the hydrolysis of 3-hydroxysteroid sulfate such as dehydroepiandrosterone sulfate (DHEAS), estrone sulfate (E1S) and pregnenolone sulfate (PREGS), which are inactive on their respective receptor, into their corresponding free steroids, DHEA, E1 and PREG, which are assets and/or available for steroidogenesis (FIG. 2).[28] Given the large amounts of DHEAS which is a precursor of androgens in peripheral tissues targeted, it is important to monitor the activity of the STS.[22] Potentially, there are several advantages of using an STS inhibitor in the context of prostate cancer. Firstly, it would prevent the intracrine transformation of abundant precursor DHEAS produced by the adrenal androgenic hormones in peripheral tissues such as the prostate and seminal vesicles. Also, it would prevent the transformation of the intratumoral androgen DHEAS which is active in androgen-sensitive tumors of the prostate or metastasis.[22] Furthermore, while androgens have generally been considered to be the main stimulus for the development and growth of tumors of the prostate, estrogens are now being pointed out to be potentially a significant actor in the progression of the disease.[29-32] High concentrations of E1S have been found in prostate cancer cells, and E1S has been found to be a prognosis marker of tumor aggressiveness in prostate cancer.[33] Since STS is involved in the conversion of E1S to estradiol (E2), the most potent estrogen, an STS inhibitor could also be efficient to prevent the estrogenic stimulation of the tumors. Recently, a Phase I clinical trial using an STS inhibitor (irosutat) in patients with castrate-resistant prostate cancer has been initiated in North America.[34]

Estrogen Receptor, SERM and Prostate Cancer

Estrogen receptors (ERs) are members of a nuclear receptor superfamily of ligand activated transcription factors.[35] To date, two different ERs (ERα and ERβ) have been described and shown to be critically and differentially involved in the regulation of the normal function of reproductive tissues.[36,37] In normal prostate tissues, the ERα is expressed specifically in the stromal cells and the ERβ in the epithelial cells. However, in prostate cancer cells, both ERα and ERβ are expressed in a similar proportion.[39] There is currently increasing evidence on the role played by estrogens in prostate cancer initiation and progression.[31,40] Estrogens are involved in the activation or inhibition of key proteins like TGFα,[41] insulin growth like factor,[42] TGFβ,[42] calmodulin,[43] protein kinase C,[44] p21wasfll/cipl CIPI[45] and TMPRSS2:ERG.[46] Thus it appears that, in addition to androgens, estrogens are also fundamentally involved in the regulation of malignant growth in the prostate.[47,48]

A selective estrogen receptor modulator (SERM) interacts with estrogen receptors as agonist or antagonist depending on the target tissue. Currently available SERM compounds are used to treat and prevent breast cancer and osteoporosis, to treat ovulatory dysfunction in women, and for contraception.[49] However, the literature suggests that an SERM may also be used to treat prostate cancer.[38,47,48] In recent studies, the SERM toromifene was found to suppress the development of high grade of prostatic intraperithelial neoplasia (PIN) and to decrease the incidence of adenocarcinoma in the prostate transgenic mouse model showing the potential of a SERM compound to treat prostate cancer.[50,51] All these data point toward an important role for estrogen in prostate cancer, and also indicate that a SERM compound may be of great interest in the management and treatment of prostate cancer.

ISTS-SERM and Prostate Cancer

Obtaining a compound that is inhibitor of STS (ISTS) and that also possess SERM-like behavior may be greatly advantageous given that the biosynthesis of active hormones (androgen from DHEAS and estrogen from E1S respectively) as well as the estrogen receptor (ERα) will be simultaneously blocked (FIG. 3). A synergical effect due to the concerted actions of an ISTS-SERM compound may induce an increased apoptotic rate in prostate cancer cells as it has been observed in a recent study involving a combined antiandrogen and SERM for targeting the blockade of both androgen receptor (AR) and estrogen receptor (ER).[52]

Furthermore, as an important complementary effect, an ISTS-SERM compound will also prevent important side effects related to androgen deprivation. Indeed, complications stemming from the blockade of the formation of androgens (osteoporosis, hot flashes, loss of sexual desire, impotence, breast tenderness) observed with androgen deprivation therapies (ex: LHRH agonist/antagonist or anti-androgen) often discourage men to pursuing and fully complete their long-term treatment against recurrence of prostate cancer.[53] Supporting this potential adjuvant role of an ISTS-SERM compound, a recent study has shown that the SERM toromifene reduces the fracture risk in men receiving androgen deprivation therapy for prostate cancer.[54]

Endometrosis and Other Medical Conditions

Endometriosis is another medical condition that may be treated using compounds that are inhibitors of STS and that possess SERM capacity.[79,80] Other medical conditions include for example osteoporosis and benign prostatic hyperplasia.

In the development of treatments for estrogen- and androgen-dependent diseases, there is a need for compounds that are inhibitors of STS and that possess SERM capacity. Advantageously, such compounds may also present other biological activities of interest. For example, they may increase alkaline phosphate (ALP) activity.

SUMMARY OF THE INVENTION

The inventors have developed compounds that present more than one biological activity. In particular, the compounds are dual-action compounds. More specifically, the compounds according to the invention inhibit STS as well as acting as SERMs. The compounds also present other biological activities of interest, such as increasing alkaline phosphate (APL) activity. The compounds according to the invention are useful in the treatment of medical conditions involving hormones. Such conditions include for example hormone-dependent cancers such as breast cancer and prostate cancer, endometriosis, osteoporosis, benign prostatic hyperplasia, endometrial cancer. The invention thus provides the following according to aspects thereof:

(1) A compound of general formula A or A' below, or a pharmaceutically acceptable salt thereof, or a solvate or hydrate thereof,

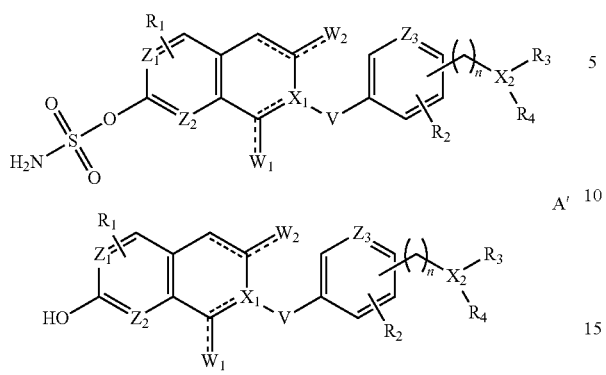

wherein:
X$_1$ and X$_2$ are each independently C, CH or N;
R$_3$ and R$_4$ are each independently H or a C$_1$-C$_{30}$ saturated or unsaturated chemical group that optionally includes at least one heteroatom selected from O, S, F, Cl, Br and I, optionally the group includes at least one C$_5$-C$_8$ cycle which is optionally substituted, optionally R$_3$ and R$_4$ together form a C$_5$-C$_8$ cycle which is optionally substituted, the C$_5$-C$_8$ cycle optionally containing at least one heteroatom selected from O, S, F, Cl, Br and I and being substituted with at least one of R$_1$ and R$_2$ as defined below;
V is C=O, C=S or CH$_2$;
R$_1$ and R$_2$ are each independently H, a C$_1$-C$_6$ alkyl, a C$_1$-C$_6$ aryl, a C$_1$-C$_{12}$ alkylaryl, phenyl optionally substituted, a C$_1$-C$_6$ alkoxy, a C$_1$-C$_6$ thioalkoxy, F, Cl, Br or I;
n is an integer from 1 to 12;
Z$_1$, Z$_2$ and Z$_3$ are each independently CH or N; and
W$_1$ and W$_2$ are each independently H, CH$_2$, O or S.

(2) A compound of general formula A or A' below, or a pharmaceutically acceptable salt thereof, or a solvate or hydrate thereof,

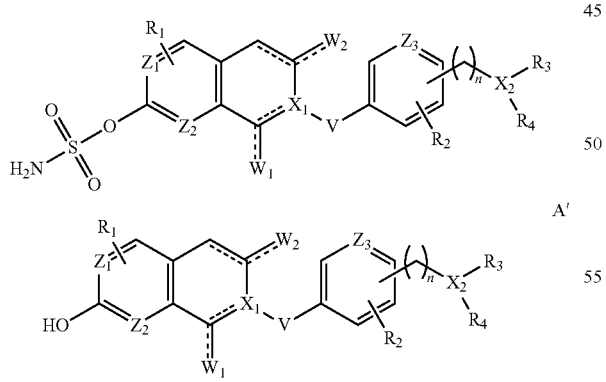

wherein:
X$_1$ and X$_2$ are each independently C, CH or N;
R$_3$ and R$_4$ are each independently H or a C$_1$-C$_{30}$ saturated or unsaturated chemical group that optionally includes at least one heteroatom selected from O, S, F, Cl, Br and I, optionally the group includes at least one C$_5$-C$_8$ cycle which is optionally substituted, optionally R$_3$ and R$_4$ together form a C$_5$-C$_8$ cycle which is optionally substituted, the C$_5$-C$_8$ cycle optionally containing at least one heteroatom selected from O, S, F, Cl, Br and I and being substituted with at least one of R$_1$ and R$_2$ as defined below;
V is C=O, C=S or CH$_2$;
R$_1$ and R$_2$ are each independently H, a C$_1$-C$_6$ alkyl, a C$_1$-C$_6$ aryl, a C$_1$-C$_{12}$ alkylaryl, phenyl optionally substituted, a C$_1$-C$_6$ alkoxy, a C$_1$-C$_6$ thioalkoxy, F, Cl, Br or I;
n is an integer from 1 to 12;
Z$_1$, Z$_2$ and Z$_3$ are each independently CH or N; and
W$_1$ and W$_2$ are each independently H, CH$_2$, O or S,
with the proviso that when: X$_1$ is N; V is C=O; R$_1$ and R$_2$ are each H; n is 1; Z$_1$, Z$_2$ and Z$_3$ are each CH; W$_1$ and W$_2$ are each H, then the group —X$_2$(R$_3$)(R$_4$) is different from:

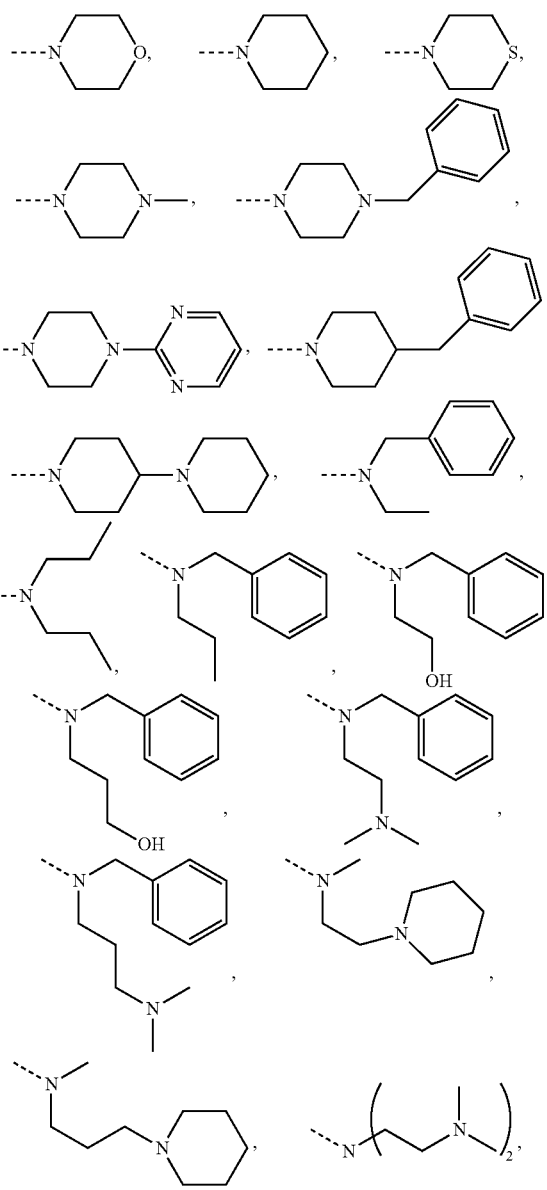

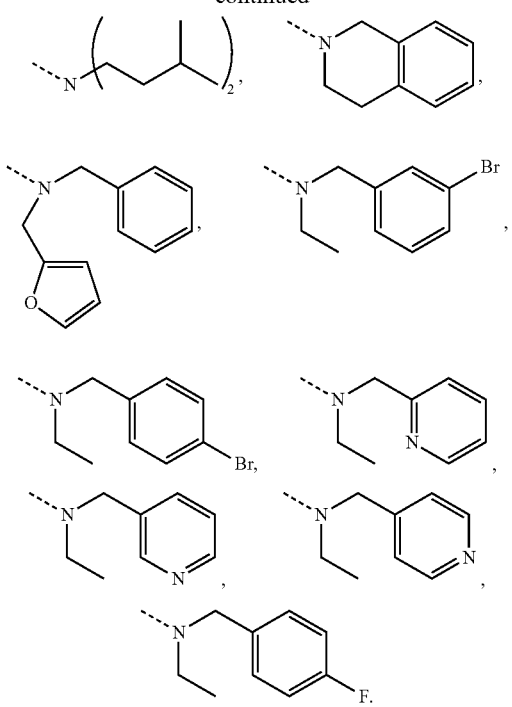

(3) A compound of general formula B or B' below, or a pharmaceutically acceptable salt thereof, or a solvate or hydrate thereof,

B

B' wherein $X_1$, $X_2$, $R_1$ to $R_4$, V and n are as defined in item (1) or in item (2).

(4) A compound of general formula C or C' below, or a pharmaceutically acceptable salt thereof, or a solvate or hydrate thereof,

C

C' wherein $X_2$, $R_1$ to $R_4$ and n are as defined in item (1) or in item (2).

(5) A compound of general formula D or D' below, or a pharmaceutically acceptable salt thereof, or a solvate or hydrate thereof,

D

D' wherein R is —$N(CH_2)_{m1}R_5(CH_2)_{m2}R_6$, m1 and m2 being each independently an integer from 1 to 12; and $R_5$ and $R_6$ being each independently a $C_1$-$C_{30}$ saturated or unsaturated chemical group that optionally includes at least one heteroatom selected from O, S, F, Cl, Br and I, optionally the group includes at least one $C_5$-$C_8$ cycle which is optionally substituted.

(6) A compound of general formula D or D' below, or a pharmaceutically acceptable salt thereof, or a solvate or hydrate thereof,

D

D' wherein R is selected from:

-continued
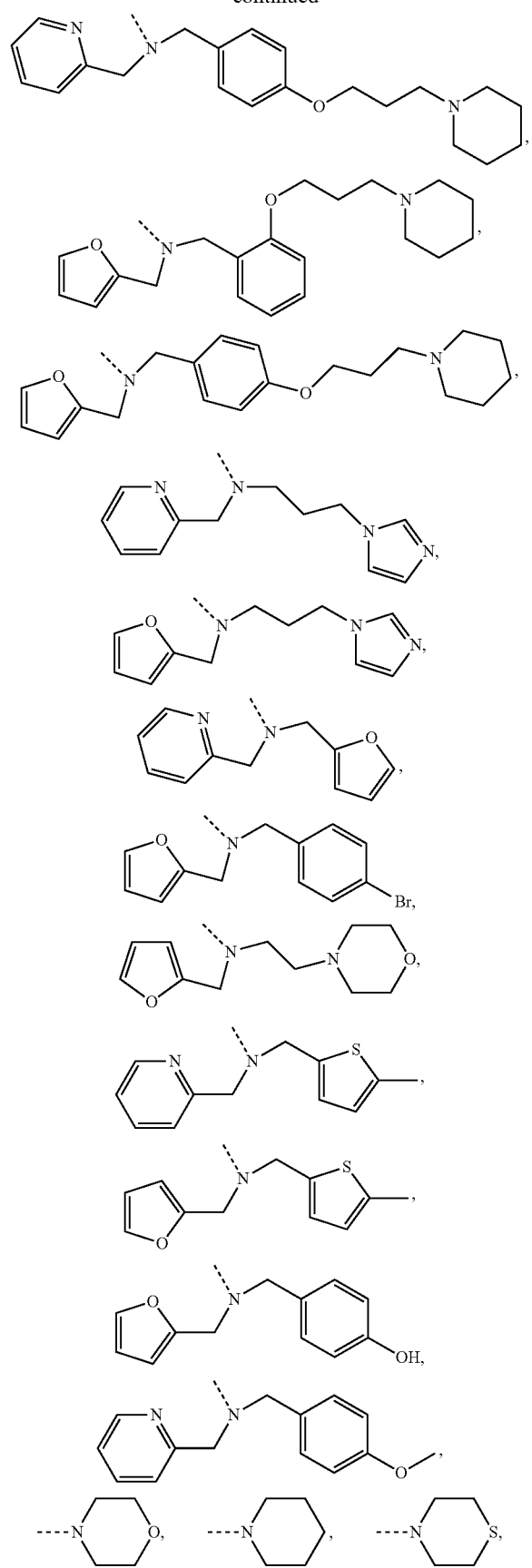
-continued
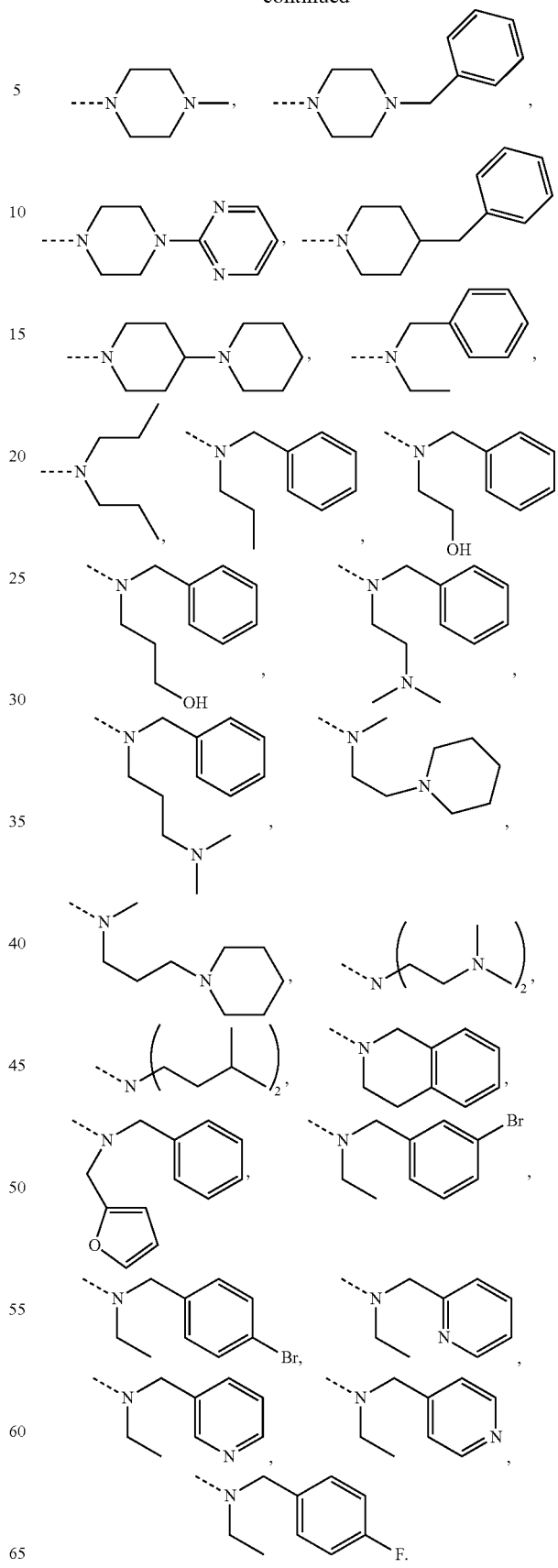

(7) A compound of general formula D or D' below, or a pharmaceutically acceptable salt thereof, or a solvate or hydrate thereof,

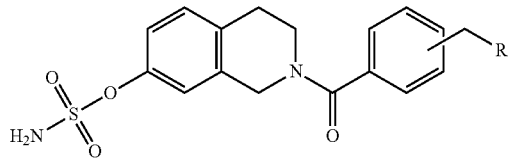

D

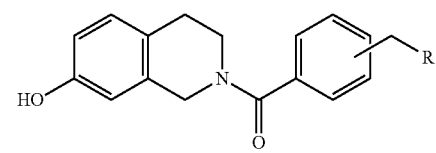

D' wherein R is selected from:

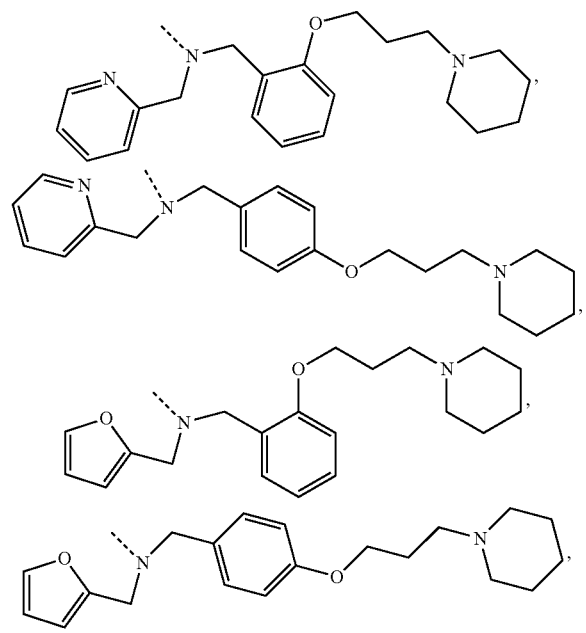

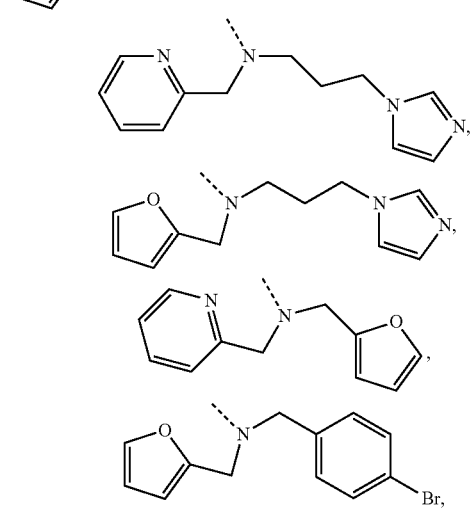

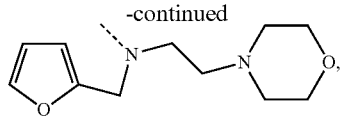

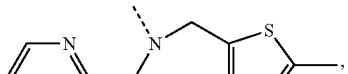

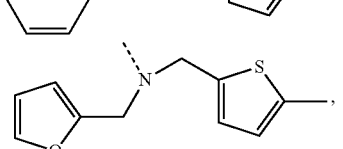

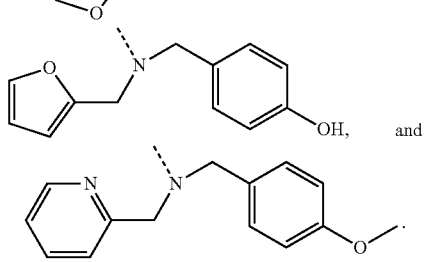

(8) A compound of general formula D or D' below, or a pharmaceutically acceptable salt thereof, or a solvate or hydrate thereof,

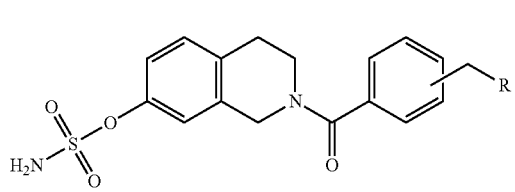

D

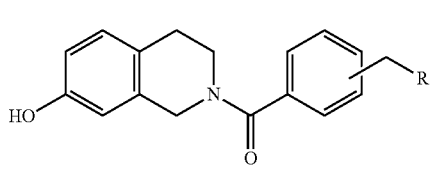

D' wherein R is selected from:

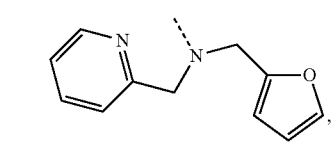

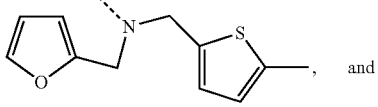

and

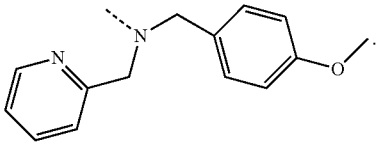

(9) A pharmaceutical composition comprising a compound as defined in any one of items (1) to (8), and a pharmaceutically acceptable carrier.

(10) A method of treating a medical condition involving hormones, comprising administering to a subject a therapeutically effective amount of a compound as defined in any one of items (1) to (8) or a therapeutically effective amount of a pharmaceutical composition as defined in item (9).

(11) A method according to item (10), wherein the medical condition is selected from: hormone-dependent cancers including breast cancer and prostate cancer, endometriosis, osteoporosis, benign prostatic hyperplasias and endometrial cancer.

(12) Use of a compound as defined in any one of items (1) to (8) or a pharmaceutical composition as defined in item (8), for treating a medical condition involving hormones.

(13) Use according to item (12), wherein the medical condition is selected from: hormone-dependent cancers including breast cancer and prostate cancer, endometriosis, osteoporosis, benign prostatic hyperplasias and endometrial cancer.

(14) Use of a compound as defined in any one of items (1) to (8), in the manufacture of a medicament for treating a medical condition involving hormones.

(15) Use according to item (14), wherein the medical condition is selected from: hormone-dependent cancers including breast cancer and prostate cancer, endometriosis, osteoporosis, benign prostatic hyperplasias and endometrial cancer.

(16) A compound as defined in anyone of items (1) to (8), for use in the treatment of a medical condition involving hormones.

(17) A compound as defined in anyone of items (1) to (8), for use in the treatment of a medical condition selected from: hormone-dependent cancers including breast cancer and prostate cancer, endometriosis, osteoporosis, benign prostatic hyperplasias and endometrial cancer.

(18) A method according to item (10) or (11) or use according to item (12) or (13), further comprising treating the subject with a second cancer therapy.

(19) A method or use according to item (18), wherein the second cancer therapy is selected from: chemotherapy, toxin therapy, radiation therapy, hormone or anti-hormone therapy, surgery, cryotherapy, immunotherapy and combinations thereof.

(20) A method according to item (10) or (11) or use according to item (12) or (13), wherein the compound is administered intravenously, intra-arterially, subcutaneously, topically or intramuscularly.

(21) A method according to item (10) or (11) or use according to item (12) or (13), wherein the cancer is multi-drug resistant, metastatic and/or recurrent.

(22) A method according to item (10) or (11) or use according to item (12) or (13), wherein the method or use comprises inhibiting cancer growth, killing cancer cells, reducing tumor burden, reducing tumor size, improving the subject's quality of life and/or prolonging the subject's length of life.

(23) A method according to item (10) or (11) or use according to item (12) or (13), wherein the subject is a human.

(24) A method according to item (10) or (11) or use according to item (12) or (13), wherein the subject is a non-human animal.

(25) A method of concurrently inhibiting steroid sulfatase (STS) activity and inducing selective estrogen receptor modulator (SERM) effects, in a subject in need thereof, the method comprising administering to the subject a therapeutically effective amount of a compound as defined in any one of items (1) to (8) or a therapeutically effective amount of a pharmaceutical composition as defined in item (9).

(26) Use of a therapeutically effective amount of a compound as defined in any one of items (1) to (8) or a therapeutically effective amount of a pharmaceutical composition as defined in item (9), for concurrently inhibiting steroid sulfatase (STS) activity and inducing selective estrogen receptor modulator (SERM) effects, in a subject in need thereof.

(27) A method of concurrently inhibiting steroid sulfatase (STS) activity, inducing selective estrogen receptor modulator (SERM) effects, and increasing alkaline phosphatase (ALP) activity, in a subject in need thereof, the method comprising administering to the subject a therapeutically effective amount of a compound as defined in any one of items (1) to (8) or a therapeutically effective amount of a pharmaceutical composition as defined in item (9).

(28) Use of a therapeutically effective amount of a compound as defined in any one of items (1) to (8) or a therapeutically effective amount of a pharmaceutical composition as defined in item (9), for concurrently inhibiting steroid sulfatase (STS) activity, inducing selective estrogen receptor modulator (SERM) effects, and increasing alkaline phosphatase (ALP) activity, in a subject in need thereof.

(29) A method of concurrently inhibiting steroid sulfatase (STS) activity and selectively blocking activation of estrogen receptor in a first group of cells while stimulating estrogen receptor in a second group of cells, in a subject in need thereof, the method comprising administering to the subject a therapeutically effective amount of a compound as defined in any one of items (1) to (8) or a therapeutically effective amount of a pharmaceutical composition as defined in item (9).

(30) Use of a therapeutically effective amount of a compound as defined in any one of items (1) to (8) or a therapeutically effective amount of a pharmaceutical composition as defined in item (9), for concurrently inhibiting steroid sulfatase (STS) activity and selectively blocking activation of estrogen receptor in a first group of cells while stimulating estrogen receptor in a second group of cells, in a subject in need thereof.

(31) A method of concurrently inhibiting steroid sulfatase (STS) activity, selectively blocking activation of estrogen receptor in a first group of cells while stimulating estrogen receptor in a second group of cells, and increasing alkaline phosphatase (ALP) activity in the second group of cells, in a subject in need thereof, the method comprising administering to the subject a therapeutically effective amount of a compound as defined in any one of items (1) to (8) or a therapeutically effective amount of a pharmaceutical composition as defined in item (9).

(32) Use of a therapeutically effective amount of a compound as defined in any one of items (1) to (8) or a therapeutically effective amount of a pharmaceutical composition as defined in item (9), for concurrently inhibiting steroid sulfatase (STS) activity, selectively blocking activation of estrogen receptor in a first group of cells while stimulating estrogen receptor in a second group of cells, and increasing alkaline phosphatase (ALP) activity in the second group of cells, in a subject in need thereof.

(33) A method of concurrently blocking activation of estrogen receptor in a first group of cells and stimulating estrogen receptor in a second group of cells, in subject in need thereof, the method comprising administering to the subject a therapeutically effective amount of a compound as defined in any one of items (1) to (8) or a therapeutically effective amount of a pharmaceutical composition as defined in item (9).

(34) Use of a therapeutically effective amount of a compound as defined in any one of items (1) to (8) or a therapeutically effective amount of a pharmaceutical composition as defined in item (9), for concurrently blocking activation of estrogen receptor in a first group of cells and stimulating estrogen receptor in a second group of cells, in subject in need thereof.

(35) A method of concurrently blocking activation of estrogen receptor in a first group of cells, stimulating estrogen receptor in a second group of cells, and increasing alkaline phosphatase (ALP) activity in the second group of cells, in subject in need thereof, the method comprising administering to the subject a therapeutically effective amount of a compound as defined in any one of items (1) to (8) or a therapeutically effective amount of a pharmaceutical composition as defined in item (9).

(36) Use of a therapeutically effective amount of a compound as defined in any one of items (1) to (8) or a therapeutically effective amount of a pharmaceutical composition as defined in item (9), for concurrently blocking activation of estrogen receptor in a first group of cells, stimulating estrogen receptor in a second group of cells, and increasing alkaline phosphatase (ALP) activity in the second group of cells, in subject in need thereof.

(37) A method according to any one of items (29), (31), (33) and (35) or use according to any one of items (29), (31) and (35), wherein the cells of the first group are breast cells or prostate cells, and the cells of the second group are bone cells.

(38) A method of concurrently inhibiting steroid sulfatase (STS) activity and inducing selective estrogen receptor modulator (SERM) effects, in cells, the method comprising contacting the cells with a compound as defined in any one of items (1) to (8), the method being performed in vitro.

(39) A method of concurrently inhibiting steroid sulfatase (STS) activity, inducing selective estrogen receptor modulator (SERM) effects, and increasing alkaline phosphatase (ALP) activity, in cells, the method comprising contacting the cells with of a compound as defined in any one of items (1) to (8), the method being performed in vitro.

(40) A method of concurrently inhibiting steroid sulfatase (STS) activity and selectively blocking activation of estrogen receptor in a first group of cells while stimulating estrogen receptor in a second group of cells, the method comprising contacting the cells with a compound as defined in any one of items (1) to (8), the method being performed in vitro.

(41) A method of concurrently inhibiting steroid sulfatase (STS) activity, selectively blocking activation of estrogen receptor in a first group of cells while stimulating estrogen receptor in a second group of cells, and increasing alkaline phosphatase (ALP) activity in the second group of cells, the method comprising contacting the cell with a compound as defined in any one of items (1) to (8), the method being performed in vitro.

(42) A method of concurrently blocking activation of estrogen receptor in a first group of cells and stimulating estrogen receptor in a second group of cells, the method comprising contacting the cells with a compound as defined in any one of items (1) to (8), the method being performed in vitro.

(43) A method of concurrently blocking activation of estrogen receptor in a first group of cells, stimulating estrogen receptor in a second group of cells, and increasing alkaline phosphatase (ALP) activity in the second group of cells, the method comprising contacting the cells with a compound as defined in any one of items (1) to (8), the method being performed in vitro.

(44) A method according to any one of items (40) to (43), wherein the cells of the first group are breast cells or prostate cells, and the cells of the second group are bone cells.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this disclosure pertains.

As used herein, the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used herein, term "alkyl" or "alk" represents a monovalent group derived from a straight or branched chain saturated hydrocarbon.

As used herein, the term "aryl" represents mono- and/or bicyclic carbocyclic ring systems and/or multiple rings fused together.

As used herein, the term "alkylaryl" represents an aryl group attached to the parent molecular group through an alkyl group.

As used herein, the terms "alkoxy" represents an alkyl group attached to the parent molecular group through an oxygen atom.

As used herein, the term "thioalkoxy" represents an alkyl group attached to the parent molecular group through a sulfur atom.

Figure 1:
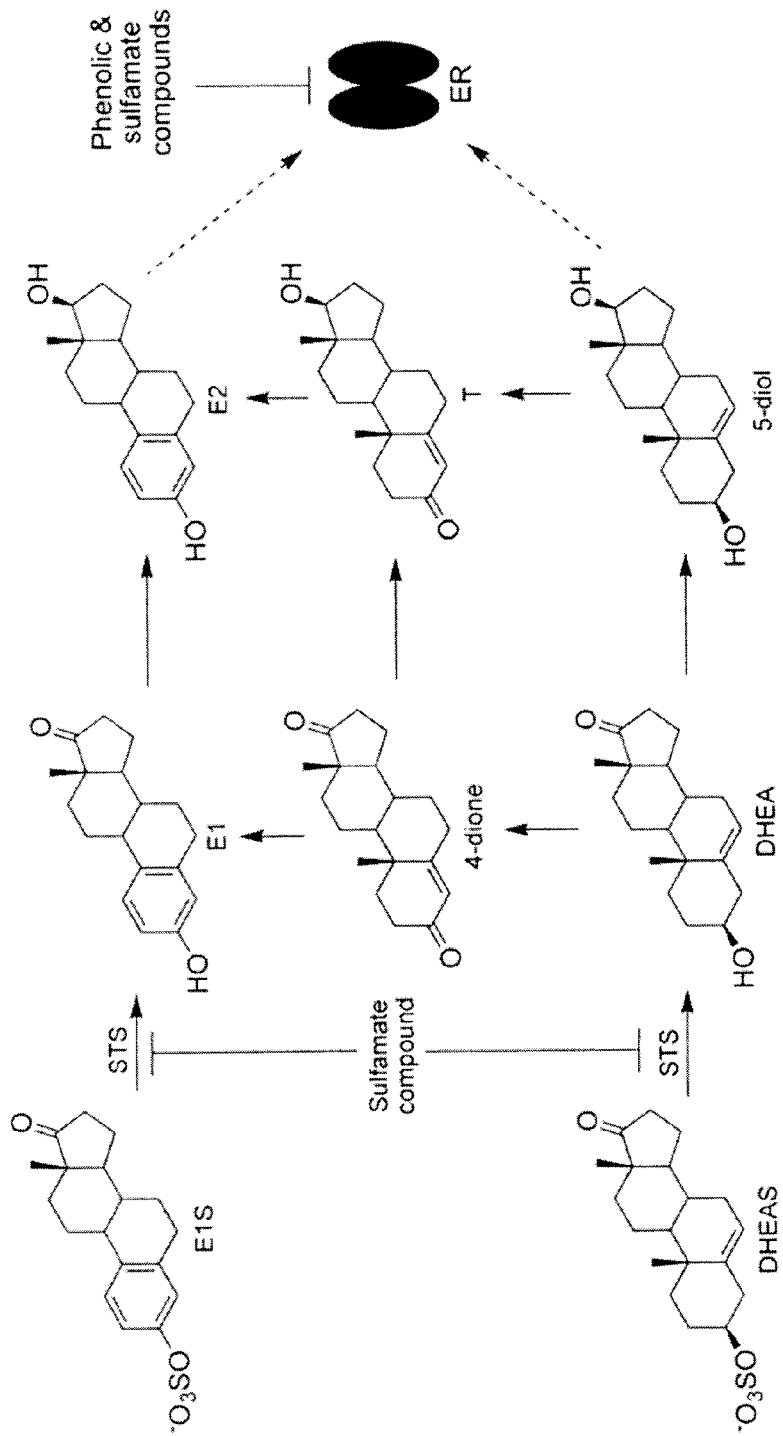
FIG. 1 illustrates the transformation by steroid sulfatase (STS) of sulfated steroids E1S and DHEAS into their corresponding active hormones, and the site of action of dual-action compounds (sulfamates and phenols). The sulfamate compound inhibits the conversion of the inactive sulfated precursors E1S and DHEAS into active E1 and DHEA, respectively, by releasing the phenolic analogue. Both the sulfamate and the phenolic compounds potentially block the estrogen receptor (ER) from activation by E2 and 5-diol in breast tissue.
Figure 2:
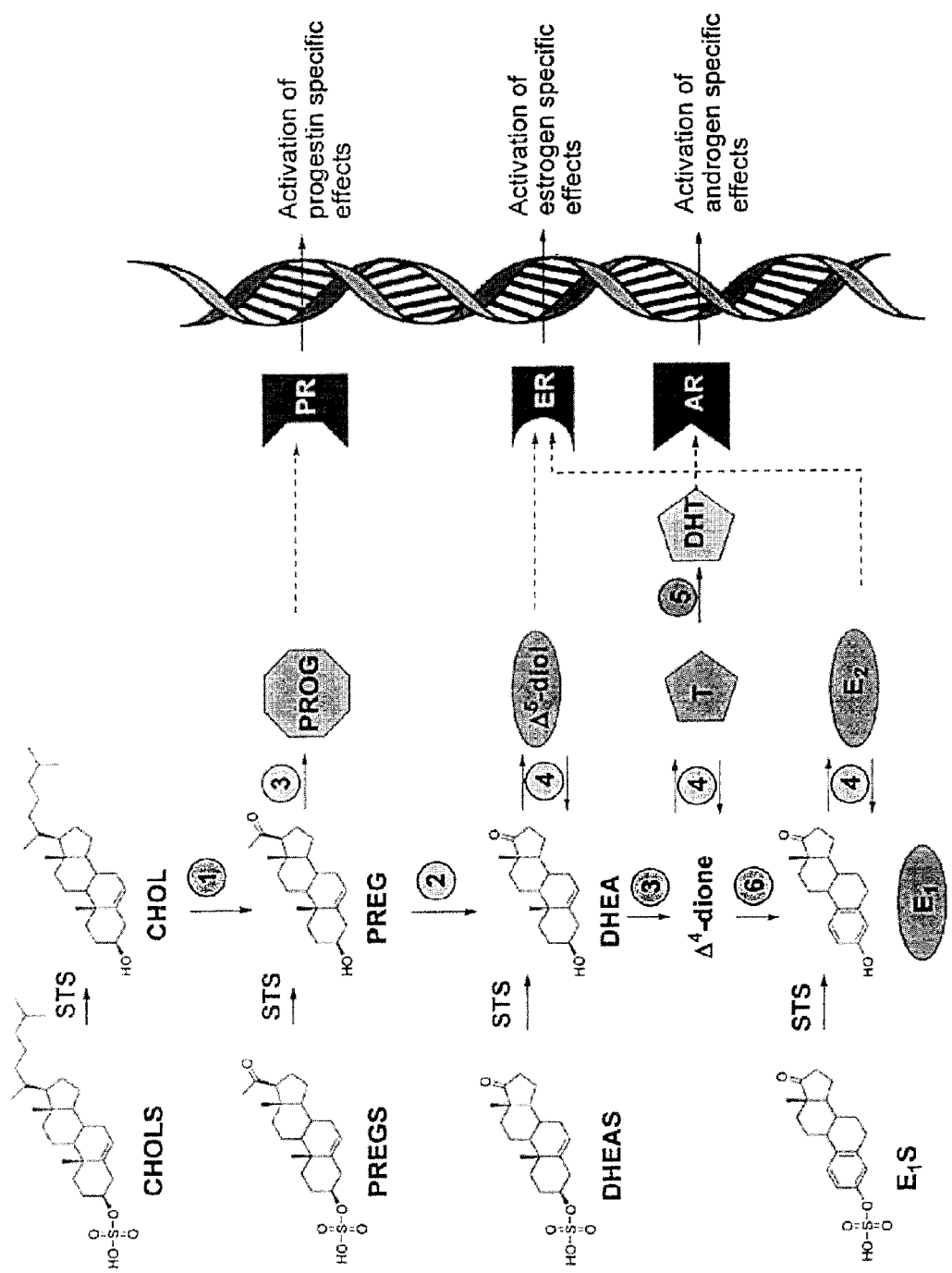
FIG. 2 illustrates the role of STS in the transformation of inactive sulfated steroids into their corresponding active 3-OH forms. STS: steroid sulfatase; 1: P450 side-chain cleavage; 2: P450 17α-hydroxyl/P450-17,20 lyase; 3: 3β-hydroxysteroid dehydrogenases/$\Delta^5$-$\Delta^4$ isomerase; 4: 17β-hydroxysteroid dehydrogenases; 5: 5α-reductases; AR: androgen receptor; ER: estrogen receptor; PR: progesterone receptor; CHOLS: cholesterol sulfate; DHEAS: dehydroepiandrosterone sulfate; DHT: dihydrotestosterone; E1S: estrone sulfate; E2: estradiol; PREGS: pregnenolone sulfate; PROG: progesterone; T: testosterone; $\Delta^5$-diol: androst-5-ene-3β,17β-diol; $\Delta^4$-dione: androst-4-ene-3,17-dione.
Figure 3:
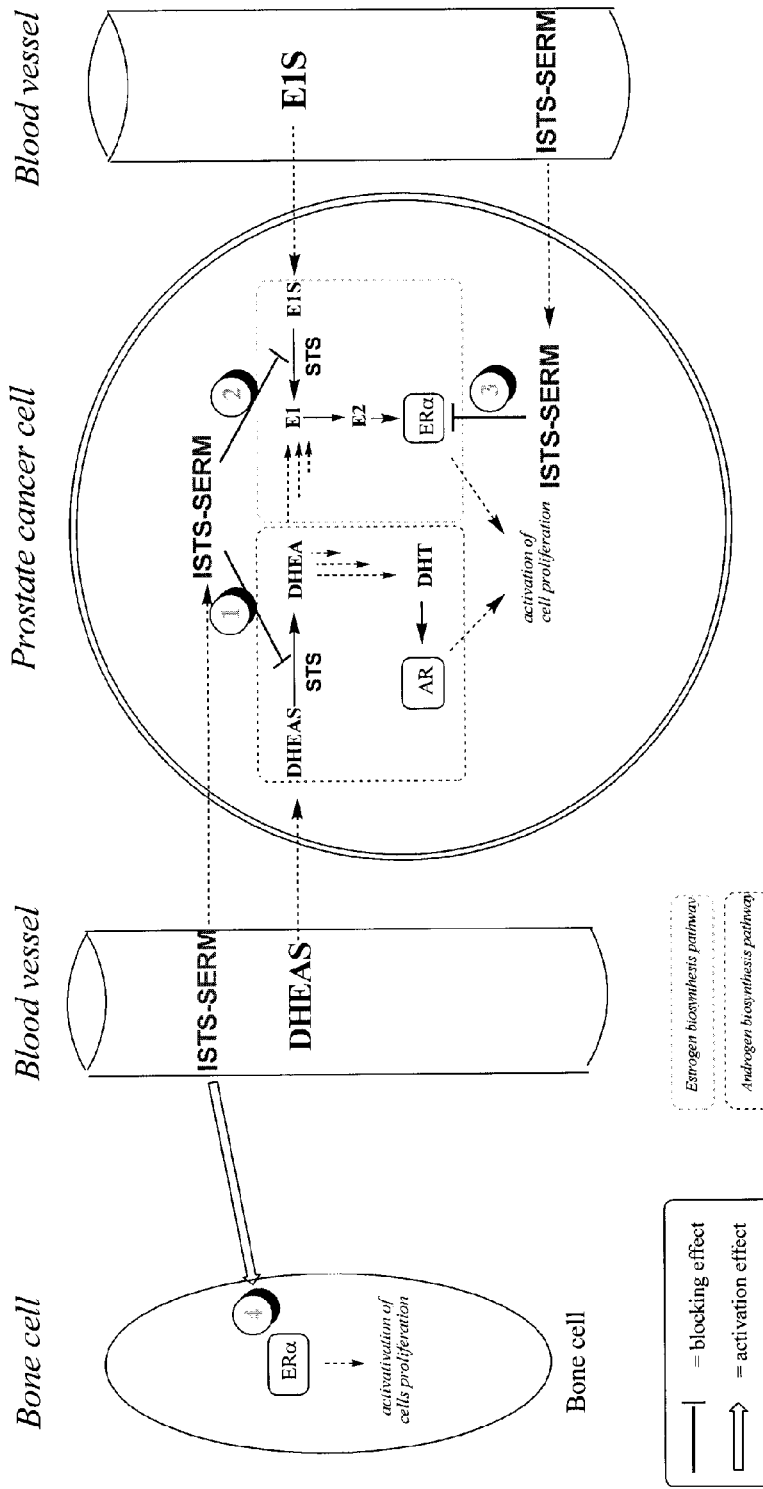
FIG. 3 illustrates the targets areas (1-4) for the ISTS-SERM compounds developed (ex: EO-33) are: 1) blockade of androgen biosynthesis (DHEAS to DHT) through STS inhibition (antiproliferation effect in prostate cancer cells); 2) blockade of estrogen biosynthesis (E1S to E2) through STS inhibition (antiproliferation effect in prostate cancer cells); 3) blockade of estrogen receptor (ERα) (antiproliferation effect in prostate cancer cells); and 4) activation of the estrogen receptor (ERα) in bone tissues (proliferation effect on bone cells).
Figure 4:
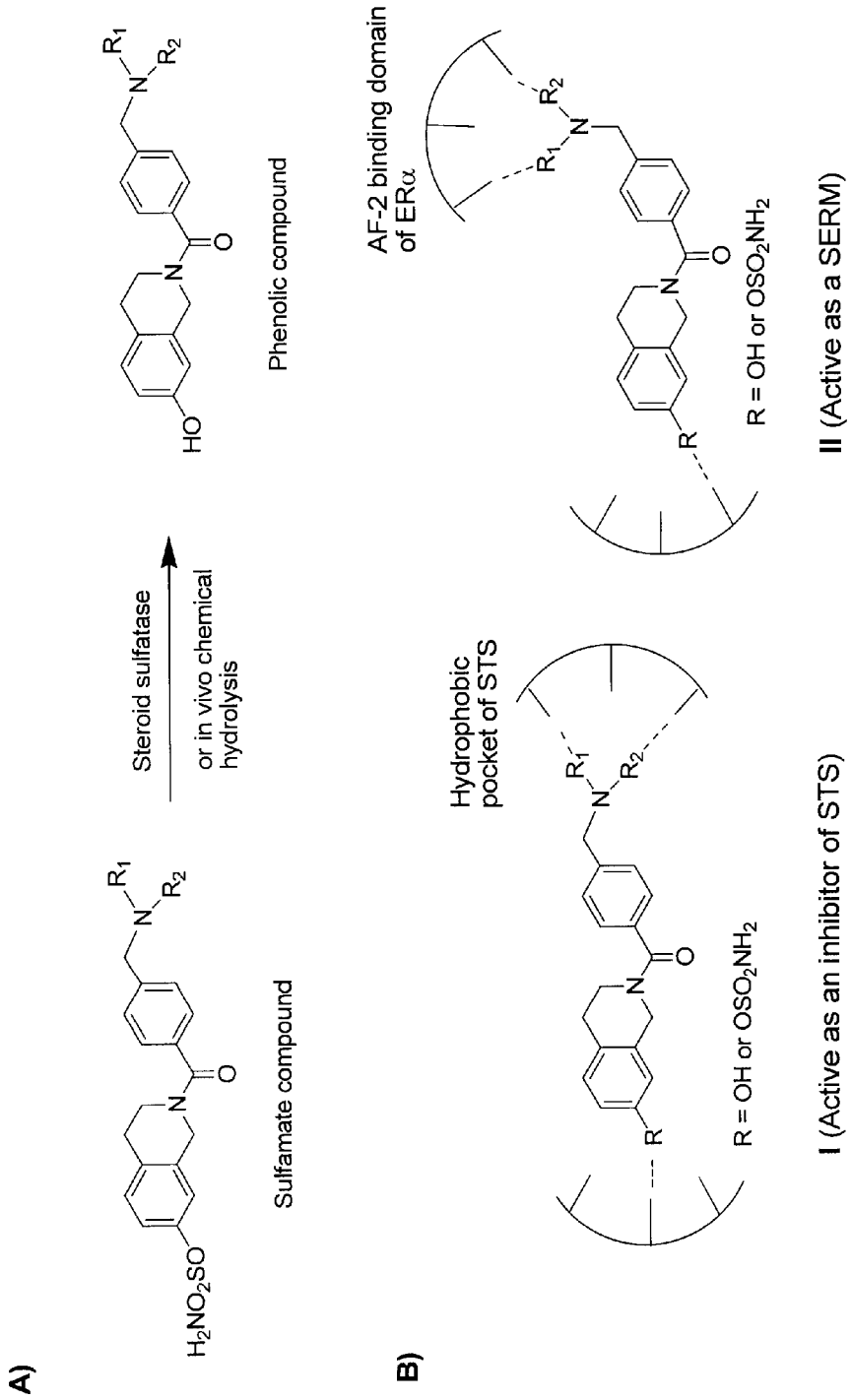
FIG. 4 illustrates A) the conversion of sulfamate compounds into their corresponding phenolic compounds by steroid sulfatase (STS) or by chemical hydrolysis. B) the binding of sulfamate to the active site of the enzyme, thus inactivating the STS. The sulfamate by itself or via the released phenol could act as an SERM compound on ERα.

The compounds according to the invention are non-steroidal compounds. They were synthesized by parallel solid-phase chemistry using a multidetachable sulfamate linker.[56-58] The sulfamate-containing STS inhibitors release the phenolic analogues after the irreversible cleavage by STS or chemical hydrolysis. This is outlined in FIG. 4.

For the initial screening, a library of phenolic compounds was tested on estrogen-sensitive breast cancer T-47D cells. Three phenolic compounds showed good initial results and were selected with corresponding sulfamate compounds for further testing. The six selected compounds were tested in HEK-293 transfected cells as STS inhibitors, on T-47D cells to evaluate their non-estrogenic and antiestrogenic properties and on osteoblast-like Saos-2 cells to evaluate their capacity to stimulate cell proliferation and alkaline phosphatase activity.

Chemistry
Selection and Chemical Synthesis of Secondary Amines as Building Blocks Referring to Scheme 1 below, the choice of the secondary amines building blocks (compounds 1a-b, 2a-b, 3c, 4c, 5-11) used to prepare the phenol library (compounds 19-31) was guided by their potential capacity to interact either with STS enzyme (hydrophobic substituent) or with the estrogen receptor (H-bond acceptor groups). In the case of STS, it is well known that hydrophobic chains are well tolerated considering the presence of a large hydrophobic pocket in the active site of the enzyme.[59] We thus selected secondary amines that bear hydrophobic substituent like 4-bromophenyl, furan and thiophene groups. Interestingly, the 4-bromophenyl and furan groups were previously found to be the most potent substituents from a series of tetrahydroisoquinoline derivatives synthesized as STS inhibitors in a precedent structure activity relationship (SAR) study.[16]

In parallel to hydrophobic chains for STS inhibition, we were interested by amines that bear hydrogen bond acceptor group, like pyridine, imidazole, morpholine or piperidine, to favor interaction with the estrogen receptor key amino acid. Indeed, it is well known that key amino acids involved in the stabilisation of the H12 helix of estrogen receptor like Asp351 could be targeted to induce SERM activity.[60] In that purpose, we selected amines of different sizes, shape and hydrogen bond acceptor capacity. Particularly, we synthesized the phenoxypropyl-piperidine chains which have been frequently reported as constituting an important pharmacophore in several SERM compounds.[61]

Example 1—Chemical Synthesis of Secondary Amines as Building Blocks (Compounds 1a-b, 2a-b, 3c, 4c, 5-11)

The secondary amines 1a-b, 2a-b, 3c, 4c and 5-11 were synthesized by reacting the aldehydes 1-4 and appropriate amines a-c under classic conditions of reductive amination using molecular sieves in ethanol followed by the reduction of the intermediate imine with sodium borohydride. This is outlined in Scheme 1 below.[62] The aldehydes 1 and 2 were beforehand synthesized by reacting 2- or 4-hydroxybenzaldehyde and 1-(3-chloropropyl)piperidine with sodium carbonate and sodium iodide in refluxing acetone.

Scheme 1
Scheme 1. Preparation of building blocks (secondary amines 1a-b, 2a-b, 3c and 4c) and structures of all commercially available secondary amines 5-11 used for the synthesis of targeted tetrahydroisoquinoline phenolic derivatives.

Aldehydes:

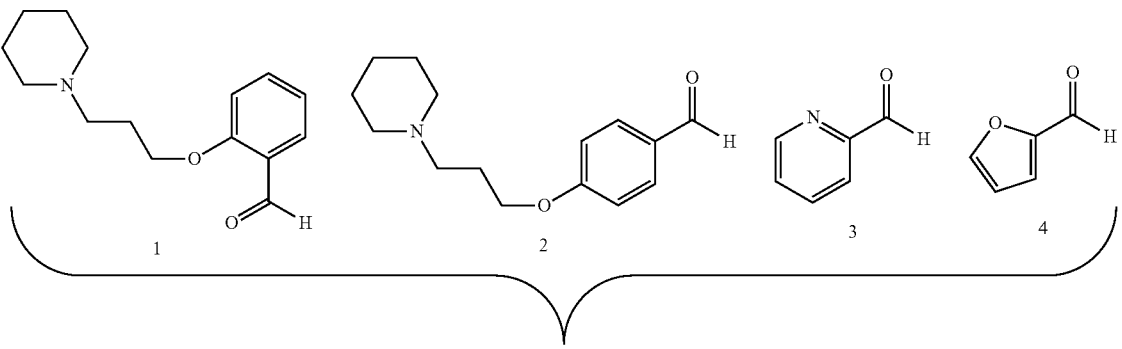

Primary Amines:

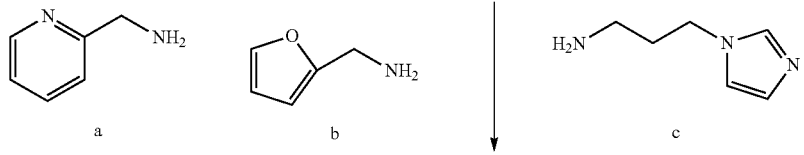

Secondary Amines:

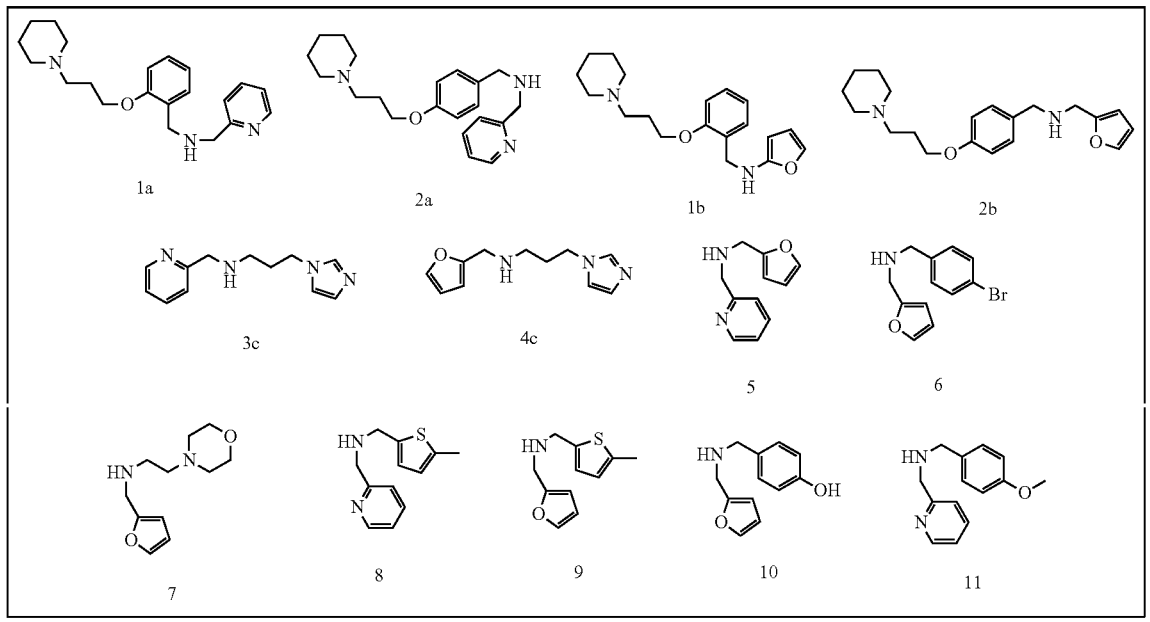

Example 2—Chemical Synthesis of Phenol Library (Compounds 19-31)

The general synthetic methodology for the preparation of all library members is outlined in Scheme 2 below. The starting compound 1,2,3,4-tetrahydroisoquinolin-7-ol (12) was selectively protected as the N-Fmoc derivative 13, which after a sulfamoylation of the phenol yielded the sulfamate 14. This sulfamate derivative was then reacted with the trityl chloride resin to give the solid-phase bounded compound 15. Removal of the Fmoc protecting group provided resin 16 with a free NH, which was acylated with carboxybenzaldehyde to give resin 17. The diversification of 17 was obtained by performing a reductive amination with various secondary amines that yielded resin 18. Finally, the phenol derivatives 19-31 were obtained by a nucleophilic cleavage from resin 18. The released compounds were found sufficiently pure to proceed to the estrogenicity test on T-47D (ER$^+$) cells. The compounds that showed no trace of estrogenicity and toxicity (compounds 25, 29 and 31) were then purified by flash chromatography and submitted to a series of biological assays.

Scheme 2
Scheme 2. Reagents and conditions for the chemical synthesis of phenol library (compounds 19-31) and sulfamate compounds (32-34).
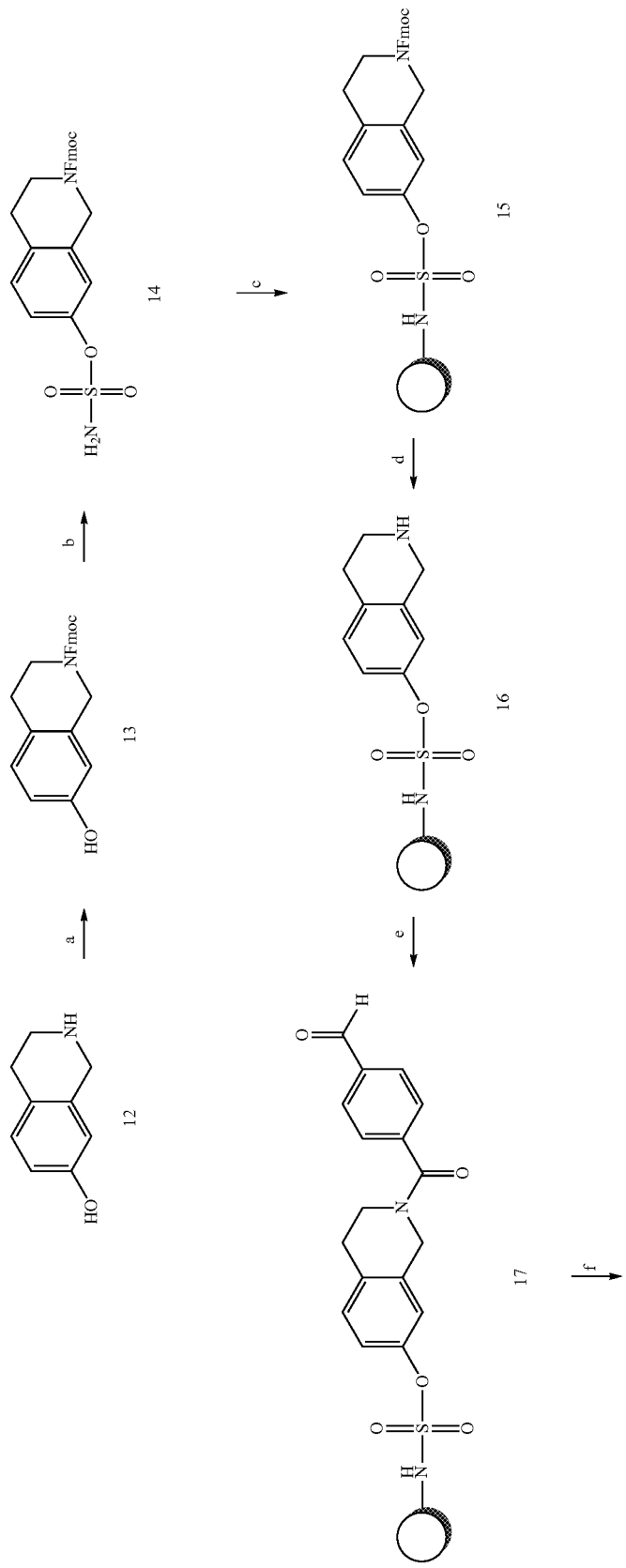

-continued
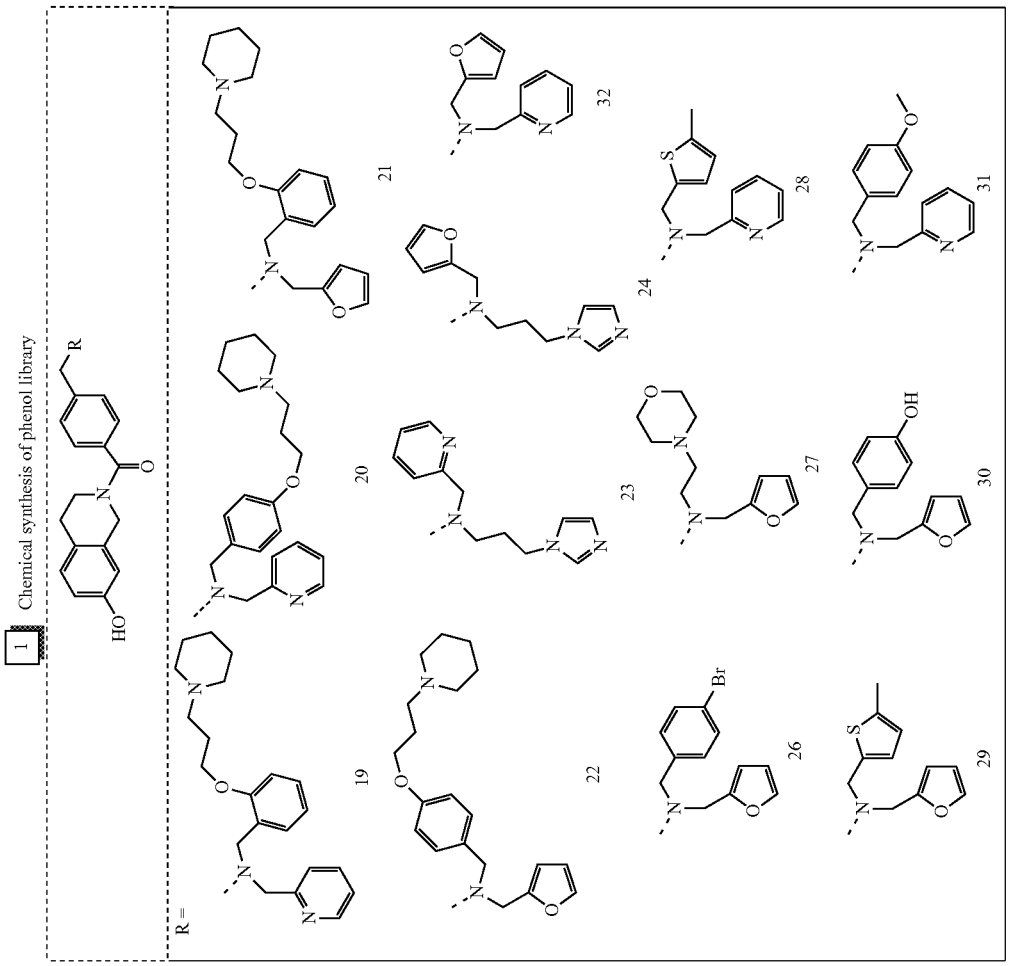
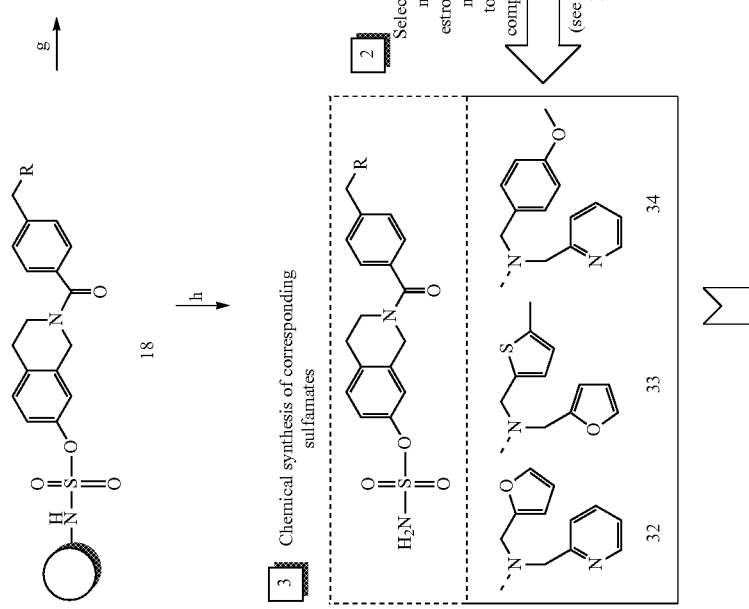
Representation of the four steps (1-4) behind the identification of dual-action compounds. (a) Fmoc-O-succinimide, NaHCO₃, H₂O; (b) NH₂SO₂Cl, 2,6-di-tert-butyl-4-methylpyridine, DCM; (c) trityl chloride resin, DIPEA, DMA/DCM; (d) 20% piperidine in DMF; (e) carboxybenzaldehyde, DIPEA, HOBt, PyBOP, DMF; (f) secondary amine (R₁R₂NH), NaBH(OAc)₃, 10% AcOH, in NMP; (g) 30% DEA in THF, 60° C.; (h) 30% HFIP in DCM.

Example 3—Chemical Synthesis of Sulfamates 32-34

The corresponding sulfamates 32-34 of phenols 25, 29 and 31 were synthesized using the same solid phase chemical synthesis route as for the phenol derivatives. In that case, however, an acid cleavage using HFIP was used at the end of the synthesis to release the sulfamate compounds 32-34. The compounds were then purified by flash chromatography.

Biological Assays

Initial Screening

The library of phenolic compounds described above was tested on estrogen-sensitive breast cancer T-47D cells. The results obtained are outlined in Table 1 below.

TABLE 1

| ID | R | Proliferation of T-47D cells (%) | | |
|---|---|---|---|---|
| | | 0.01 μM | 0.1 μM | 1 μM |
| 19 | | 102.8 ± 6.9 | 99.8 ± 4.2 | 37.1 ± 4.2 |
| 20 | | 105.9 ± 1.0 | 104.5 ± 4.8 | 60.7 ± 6.4 |
| 21 | | 96.8 ± 1.2 | 105.9 ± 5.6 | 0 ± 9.1 |
| 22 | | 95.6 ± 1.8 | 119.7 ± 4.8 | 133.7 ± 3.0 |
| 23 | | 102.8 ± 2.2 | 112.9 ± 3.7 | 39.2 ± 2.9 |
| 24 | | 94.9 ± 1.3 | 98.5 ± 4.5 | 114.6 ± 5.9 |
| 25 | | 104.1 ± 2.3 | 103.2 ± 2.5 | 103.5 ± 6.5 |
| 26 | | 106.3 ± 0.6 | 109.4 ± 1.2 | 59.2 ± 3.1 |

TABLE 1-continued

[Core structure: HO-substituted tetrahydroisoquinoline linked via N to C(=O)-phenyl-CH2-R]

| ID | R | Proliferation of T-47D cells (%) 0.01 μM | 0.1 μM | 1 μM |
|---|---|---|---|---|
| 27 | -N(CH2-furan-2-yl)(CH2CH2-morpholine) | 108.2 ± 5.5 | 105.9 ± 1.5 | 118.8 ± 9.6 |
| 28 | -N(CH2-pyridin-2-yl)(CH2-(5-methylthiophen-2-yl)) | 100.6 ± 3.8 | 105.4 ± 4.4 | 78.9 ± 6.8 |
| 29 | -N(CH2-furan-2-yl)(CH2-(5-methylthiophen-2-yl)) | 97.1 ± 2.6 | 103.2 ± 1.8 | 96.8 ± 2.2 |
| 30 | -N(CH2-furan-2-yl)(CH2-(4-hydroxyphenyl)) | 108.2 ± 5.5 | 138.0 ± 1.2 | 200.3 ± 4.9 |
| 31 | -N(CH2-pyridin-2-yl)(CH2-(4-methoxyphenyl)) | 105.6 ± 0.6 | 104.6 ± 7.4 | 100.9 ± 7.9 |

In Table 1, cell proliferation of control cells is set to 100%. Results are expressed as mean±SD of one experiment in triplicate.

Compounds were discarded if they stimulated the proliferation of T-47D cells (estrogenic activity) or if they showed some cytotoxicity by reducing the cell number. Amongst the library of phenolic compounds, the compounds 25, 29 and 31 showed interesting results. They showed neither estrogenicity nor cytotoxicity on T-47D cells at the concentrations tested (0.01 μM, 0.1 μM and 1 μM). The results obtained suggest that these three compounds do not possess the ability to activate ERα in breast cancer cells and consequently to induce unwanted cell proliferation.

Example 4—Steroid Sulfatase (STS) Inhibition

Figure 5:
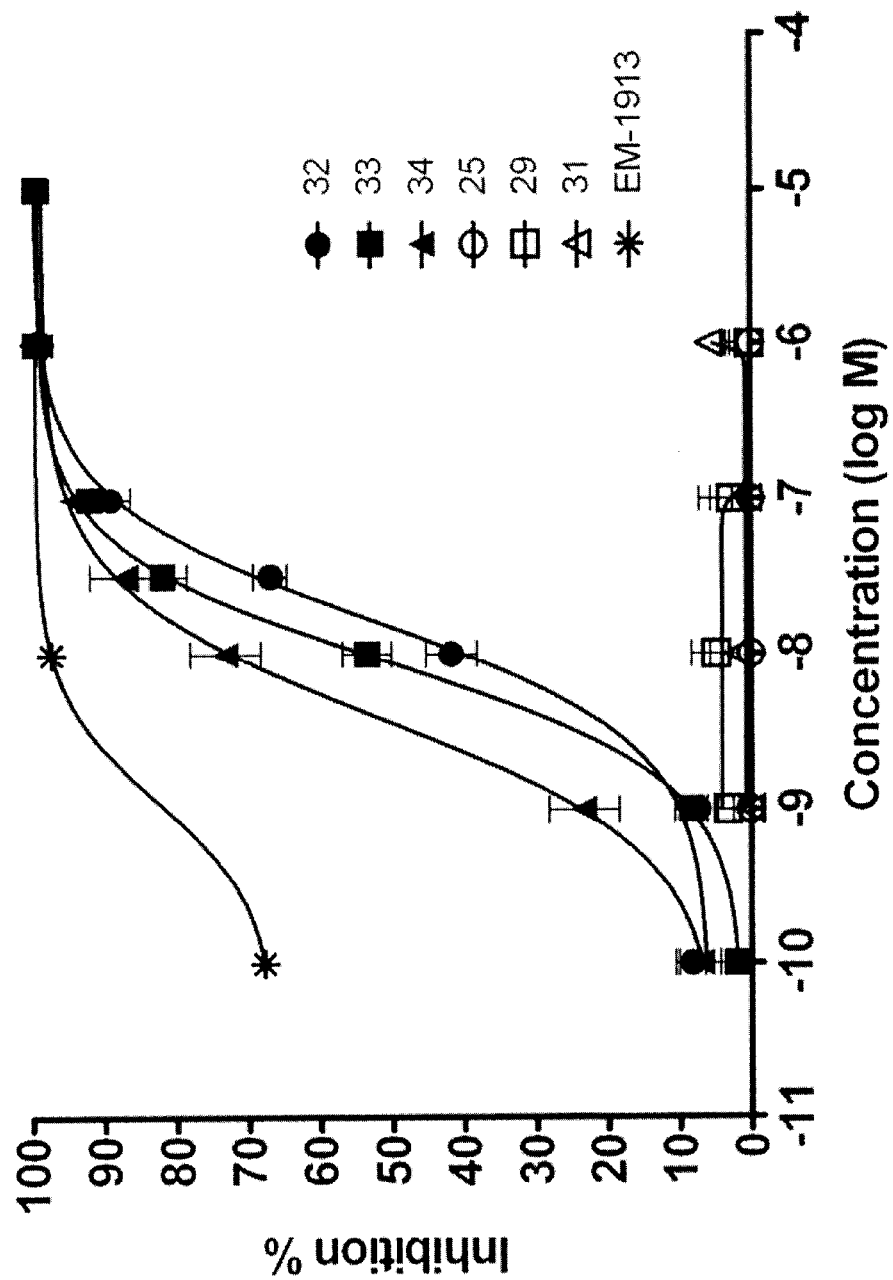
FIG. 5 illustrates the effect of the sulfamate compounds 32, 33 and 34 and their respective corresponding phenolic analogues 25, 29 and 31 on steroid sulfatase activity in homogenates of transfected HEK-293 cells. The three sulfamate derivatives inhibited STS while the three phenolic analogues showed no significant inhibition of STS. Results are expressed as % inhibition of [$^3$H]-E1S conversion into [$^3$H]-E1 by STS. Each point represents the mean±SD of triplicate measurements in one experiment.
Figure 6:
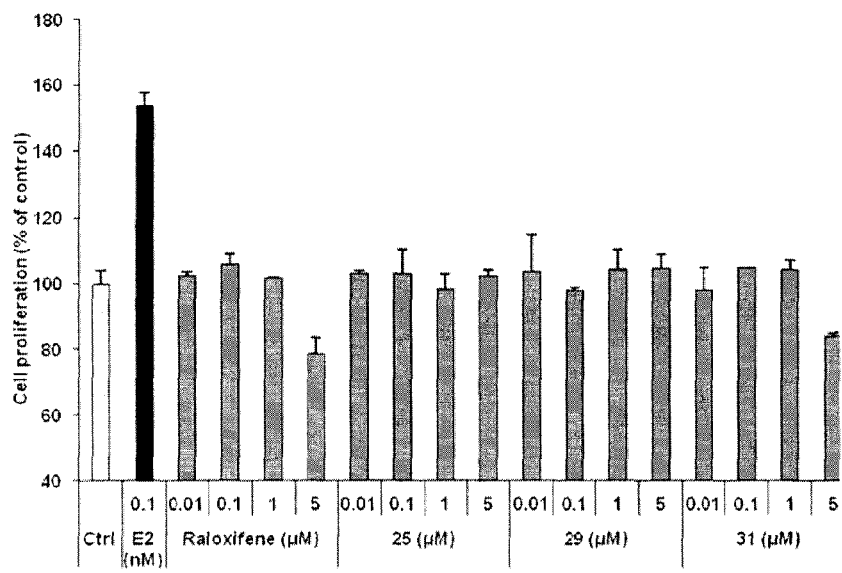
FIG. 6 illustrates the effect of phenolic (A) and sulfamate (B) compounds on T-47D cell proliferation after 7 days of treatment. The estrogenicity of the phenol derivatives 25, 29 and 31 as well as their respective corresponding sulfamate derivatives 32, 33 and 34 was evaluated by incubating the cells with different concentrations (0.01 µM to 5 µM) of each compound. The proliferation of control cells is set to 100%. Results are expressed as means±SD of triplicate measurements.
Figure 6:
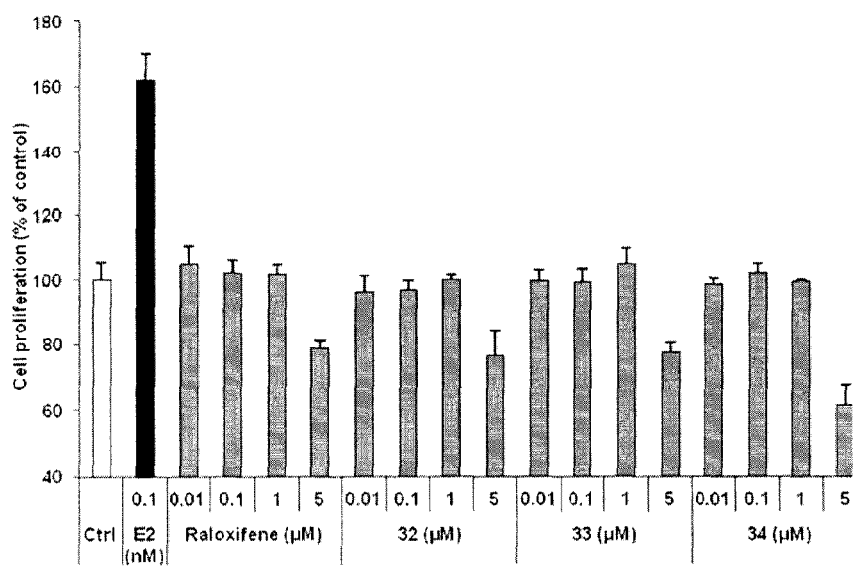

Following the results obtained with the phenolic derivatives 25, 29 and 31 in the initial screening, we synthesized the sulfamate analogues (compounds 32, 33 and 34) and evaluated their capacity to inhibit the steroid sulfatase (STS) activity. To test STS inhibition, we used homogenated HEK-293 cells overexpressing STS and evaluated the capacity of our compounds to inhibit the conversion of [$^3$H]-E1S into [$^3$H]-E1. In the test we used EM-1913, a known potent steroidal STS inhibitor, as a reference compound.[55] As reported previously in the literature, phenolic inhibitors of STS are less potent than their sulfamoylated analogues.[60, 72,73] Our results confirm the previous report, since only the sulfamate compounds inhibited STS. This is outlined in FIG. 5. Effectively, the phenolic compounds showed no significant inhibition while the sulfamate compounds showed good inhibition of STS with $IC_{50}$ values of 16.6±2.7 nM for 32, 8.9±1.2 nM for 33 and 3.9±1.1 nM for 34.

Example 5—Effect on Breast Cancer T-47D Cells

As the three sulfamate compounds 32, 33 and 34 are good inhibitors of STS, we wanted to know if they were also devoid of estrogenic activity. Along with their phenolic analogues 25, 29 and 31, to reconfirm the results of the initial screening, we tested the compounds on estrogen-sensitive T-47D cells. The results are outlined in FIGS. 4 (A and B). We used the reference compound estradiol (E2), as positive control of cell proliferation stimulation, and raloxifene, an SERM with no estrogenicity in breast tissue. E2, at a concentration of 0.1 nM, induced approximately 160% cell proliferation while raloxifene showed no estrogenic activity. Our six compounds showed good results because none of them stimulated the proliferation of T-47D cells. On the other hand, we observed cytotoxicity at 5 μM for some of the compounds. This should not be a problem as 5 μM is a high dose hardly achievable in vivo and that even raloxifene, a SERM used in clinic, induced some cytotoxicity at this concentration. The results obtained show that both the sulfamate and phenolic compounds can be used in the treatment of breast cancer without stimulation of the proliferation of cancer cells.

Figure 7:
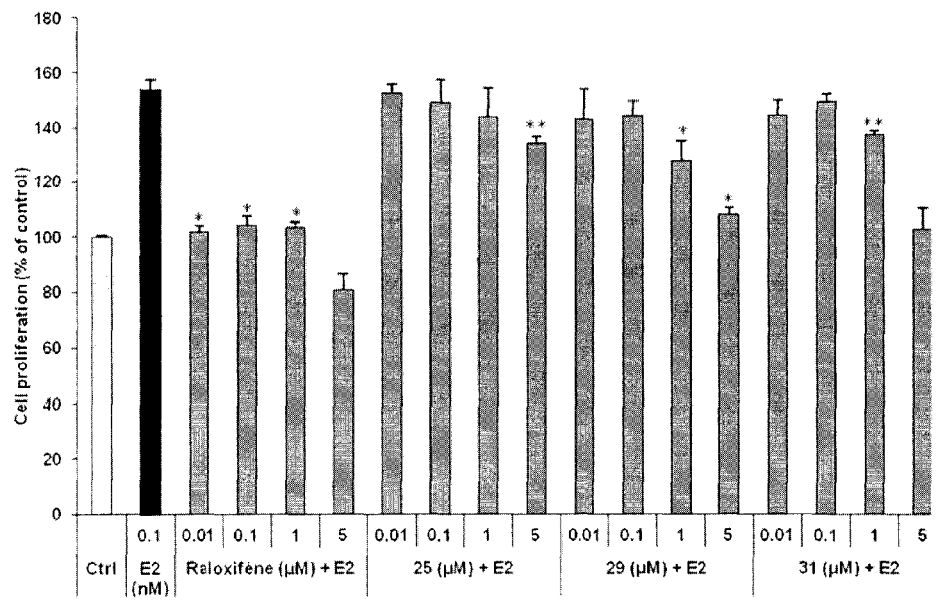
FIG. 7 illustrates the effect of phenolic (A) and sulfamate (B) compounds on T-47D cell proliferation after 7 days of treatment. The antiestrogenicity of the phenol derivatives 25, 29 and 31 as well as their respective corresponding sulfamate derivatives 32, 33 and 34 was evaluated by incubating the cells with different concentrations (0.01 µM to 5 µM) of each compound and 0.1 nM of E2. The proliferation of control cells is set to 100%. Results are expressed as means±SD of triplicate measurements. * p≤0.01 vs. E2, ** p≤0.05 vs. E2.
Figure 7:
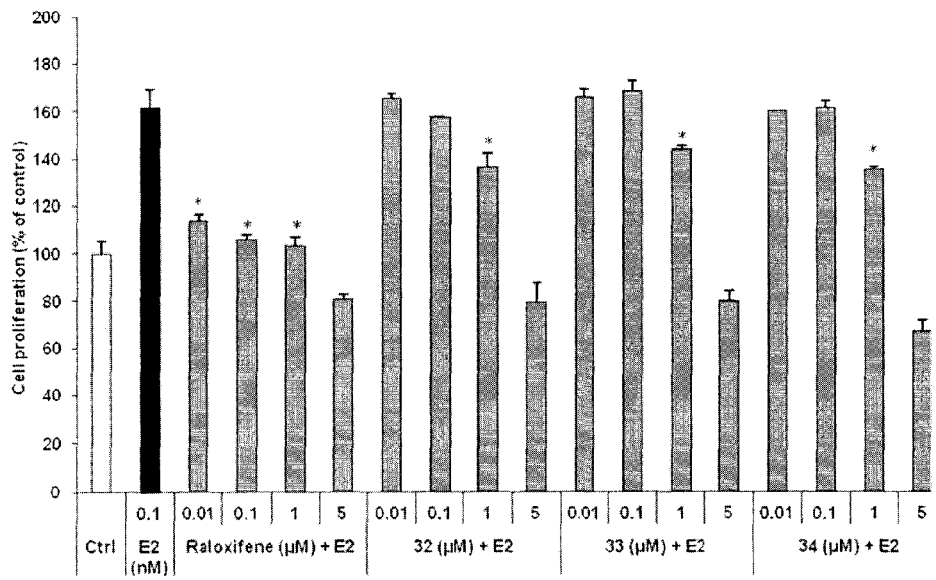

Next, we wanted to evaluate the capacity of the six compounds 25, 29, 31-34 to block the stimulation of proliferation in T-47D cells induced by E2. The results are outlined in FIGS. 7 (A and B). The cells were incubated with our six compounds and raloxifene at different concentrations in presence of E2 (0.1 nM). Raloxifene was able to block the E2 stimulation at concentrations of 0.01 µM to 1 µM and showed some cytotoxicity at 5 µM. For our six compounds, the results show that they all possess some antiestrogenic activity in T-47D cells. Because some compounds showed cytotoxicity at 5 µM in the previous test, their antiestrogenicity at this concentration was not considered. The phenol derivative 29 possesses good antiestrogenic activity since it blocked approximately 84% (at 5 µM) of the stimulation induced by E2.

Effect on Osteoblast-Like Saos-2 Cells

Example 6—Cell Proliferation

Figure 8:
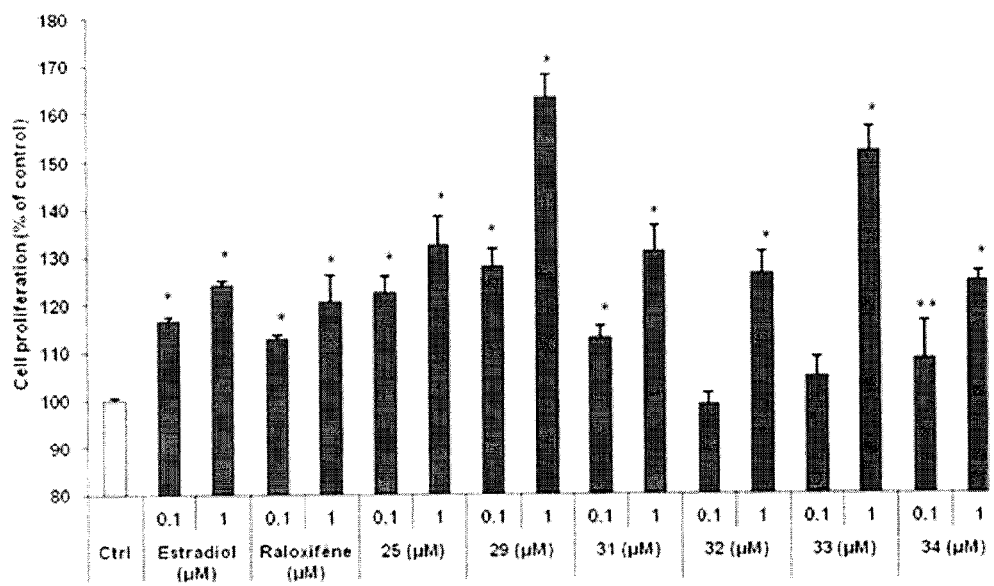
FIG. 8 illustrates the effect of phenolic and sulfamate compounds on Saos-2 cell proliferation after 7 days of treatment. A) Saos-2 cells were incubated with E2, raloxifene, the compounds 25, 29, 31, 32, 33 and 34 at 0.1 µM and 1 µM. B) The cells were incubated with raloxifene, the phenolic compound 29 or the sulfamate compound 33 at concentrations ranging from 1 nM to 10 µM. The proliferation of control cells is set to 100%. Results are expressed as means±SD of triplicate measurements. * p≤0.01 vs. control, ** p≤0.05 vs. control.
Figure 8:
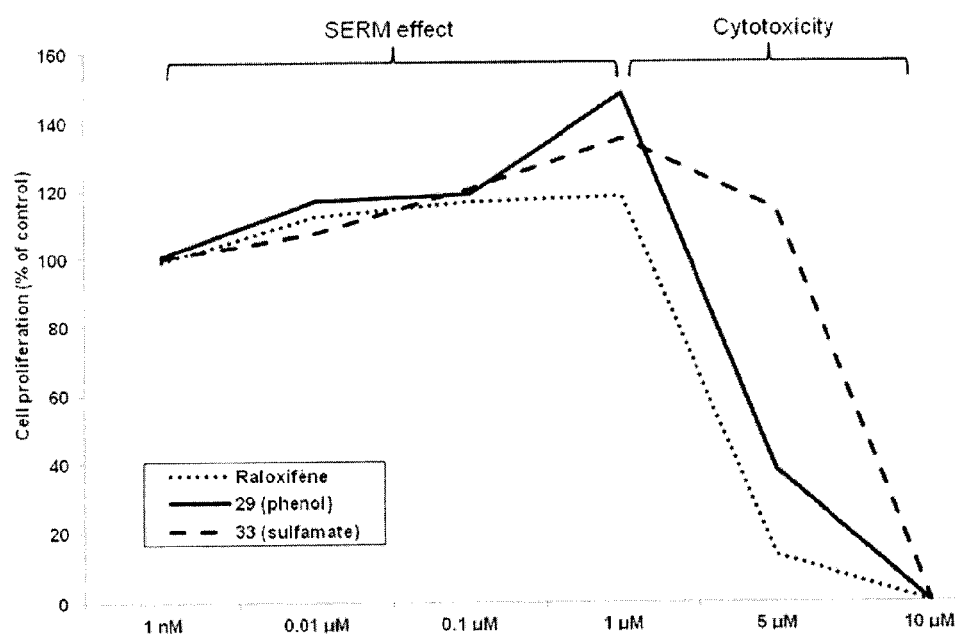

As SERMs possess the ability to block ERα in breast tissue and to activate ERα in other tissues, such as bone tissue, we investigated the action of the six compounds 25, 29, 31-34 on the osteoblast-like Saos-2 cells. First, we wanted to evaluate their effect on cell proliferation. To do so, we incubated Saos-2 cells for 7 days with estradiol (E2) or raloxifene, as a reference compound, and our six compounds at concentrations of 0.1 µM and 1 µM. This is outlined in FIG. 8A. All compounds, including E2 and raloxifene, induced cell proliferation of Saos-2 significantly at 1 µM. However, the cell proliferation induced is quite low, with the exception of the phenolic compound 29 and its sulfamate analogue 33, which both induced cell proliferation approximately by 150%. The slight cell proliferation observed is probably due to the osteoblast cells in themselves. One of the main roles of osteoblasts in bone tissue is to construct a calcified extracellular matrix.[15] As such, bone formation is not principally due to osteoblasts proliferation but rather osteoblasts maturation into mature osteocytes. To further investigate the high cell proliferation induced by the compounds 29 and 33 and to confirm the previous results obtained, Saos-2 cells were incubated for 7 days with 29 or 33 at a wider range of concentration. This is outlined in FIG. 8B. We observed an apparent dose-dependent response from 1 nM to 1 µM for raloxifene, 29 and 33. At higher concentrations, all three compounds induced cytotoxicity in Saos-2 cells.

Example 7—Alkaline Phosphatase (ALP) Activity

Figure 9:
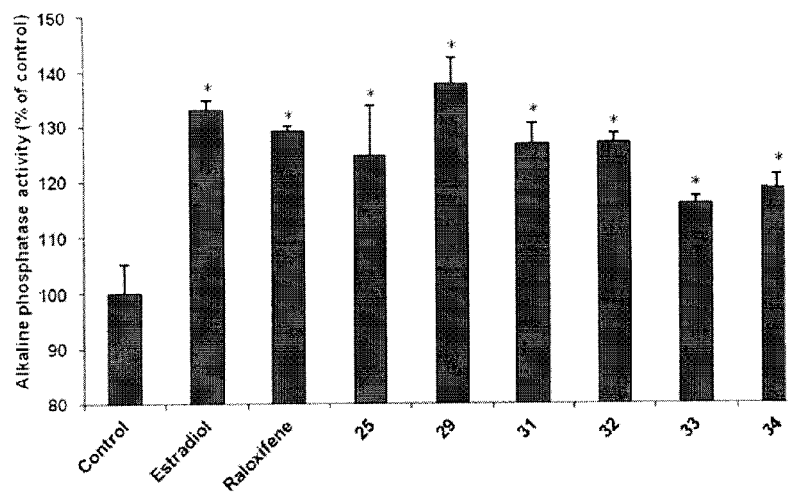
FIG. 9 illustrates the effect of the phenolic and sulfamate compounds on alkaline phosphatase (ALP) activity in Saos-2 cells after 3 days of treatment. A) Saos-2 cells were incubated with E2, raloxifene or compounds of interest at a concentration of 0.1 nM. B) Saos-2 cells were treated with 0.1 nM of E2, raloxifene or the compound 29 in presence of MPP (ERα antagonist), PHTPP (ERβ antagonist) or ICI-164,384 (pure antiestrogen) at a concentration of 1 µM. The ALP activity of control cells is set to 100%. Results are expressed as means±SD of triplicate measurements. * p≤0.01 vs. control.
Figure 9:
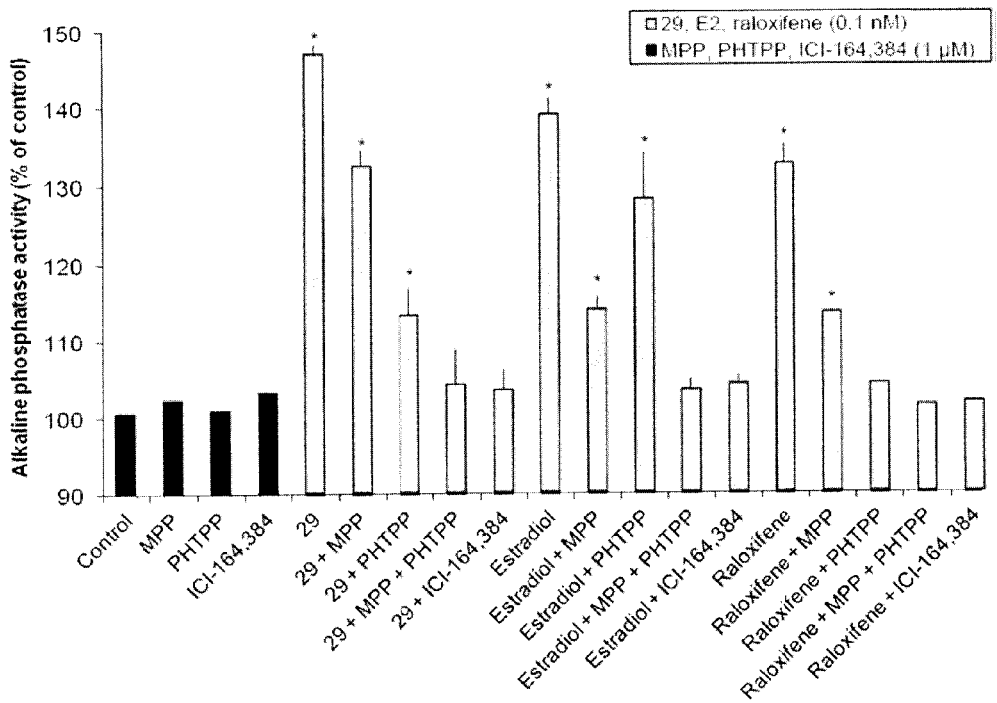

Our six compounds 25, 29, 31, 32, 33 and 34 had an apparently beneficial effect on osteoblasts. Since they induced only a slight stimulation on Saos-2 cells proliferation, we decided to investigate the activity of a differentiation marker, the alkaline phosphatase (ALP). ALP is an enzyme that releases inorganic phosphate from different intracellular substrates such as pyrophosphate and pyridoxal 5'-phosphate.[63] The inorganic phosphate is used in the formation of hydroxyapatite crystals which are then inserted in the extracellular protein scaffold to form the solid part of bone tissue. In osteoblasts cells, ALP is regulated by estrogens and constitutes a good indicator of osteoblast differentiation.[64] We tested our compounds, raloxifene or E2 on Saos-2 cells and investigated their effect on ALP activity. The results are outlined in FIG. 9A. All compounds significantly increased ALP activity in Saos-2 cells, but it is interesting to see that 29 induced the highest ALP activity (138%) similarly to the activity obtained in the cell proliferation assay.

To confirm that the observed stimulation of ALP activity induced by our compounds is mediated by estrogen receptors. We used 1,3-bis(4-hydroxyphenyl)-4-methyl-5-[4-(2-piperidinylethoxy)phenol]-1H pyrazole dihydrochloride (MPP), an ERα antagonist, 4-[2-phenyl-5,7-bis(trifluoromethyl)pyrazolo[1,5-α]pyrimidin-3-yl]phenol (PHTPP), an ERβ antagonist, and ICI 164,384, a pure antiestrogen.[65,66,71] We incubated Saos-2 cells 3 days with E2, raloxifene or compound 29, which compounds induced the highest ALP activity, in presence of 1 µM of either MPP, PHTPP, a combination of both ER subtype antagonists or with ICI 164,384. This is outlined in FIG. 9B. First, E2, raloxifene and 29 stimulated ALP activity similarly to the previous test and the three antagonists used had no effect on ALP in Saos-2 cells. The results also demonstrate that E2, raloxifene and 29 stimulated ALP activity in Saos-2 cells via estrogen receptors as the use of either ICI-164,384 or the combination of both MPP and PHTPP completely blocked the stimulation. When the antagonist MPP or PHTPP was used alone, we observed some differences in the mechanism by which E2, raloxifene and 29 stimulated ALP activity. Effectively, it seems that the stimulation induced by E2 is mediated more by ERα than by ERβ, since MPP had a greater impact than PHTPP on the decrease of ALP activity.

3D Modelization

Example 8—Superimposition of Compound 32 with Reference Compounds

Figure 10:
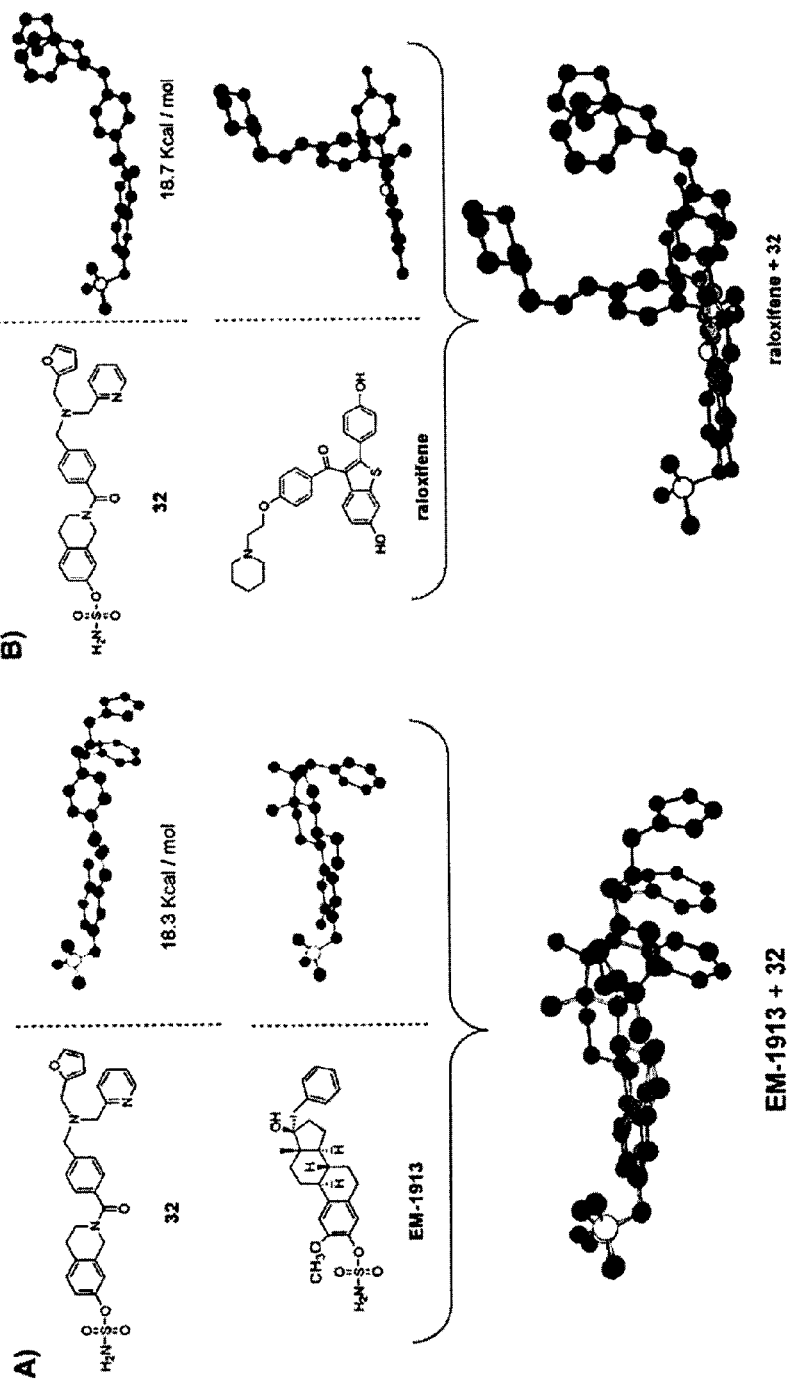
FIG. 10 illustrates A) minimized conformation energies of the compounds 32 and EM-1913 and superimposition of the two compounds; B) minimized conformation energies of the compounds 32 and raloxifene and superimposition of the two compounds.

In order to visualize and better understand the structural determinants that could be important in the STS inhibition and SERM activity observed, we proceeded to a 3D molecular modelization of one of the compound of the study, compound 32. The modelization as well as related superimposition of compound 32 with a STS inhibitor (EM-1913) and an SERM (raloxifene) was performed using Chem3D software. This is outlined in FIG. 10.[67] The two sulfamate compounds (32 and EM-1913) were first submitted to an automated MM2 energy minimization followed by a step of manual iteration in order to find the best minimum energy conformation possible. For raloxifene, the minimum conformation was converted from PDB file of raloxifene-ER complex to a Chem3D structure.[68]

Compound 32 was first superimposed to 3-O-sulfamate 17α-benzyl-2-methoxy-estra-1,3,5(10)-trien-17β-ol (EM-1913), a potent STS inhibitor that possesses a benzyl substituent at the position 17α of the E2 core.[55] This 17α-benzyl group was found to be an important pharmacophore that interacts favorably with the hydrophobic pocket of the STS.[69,70] The superimposition of the minimized structures showed a good recovery of the tetrahydroisoquinoline core of 32 with steroid scaffold of EM-1913 and a good recovery of the N-substituted moiety of compound 32 with the 17α-benzyl group of EM-1913. This is outlined in FIG. 10A.

Compound 32 was superimposed with raloxifene with an acceptable recovery following a pivotal of the N-dialkyl substituent moiety by a rotation of 180°. This is outlined in FIG. 10B. The resulting global value of steric energy for this new conformation was very close to energy conformation found for STS inhibition (18.7 Kcal/mol vs. 18.3 Kcal/mol). In this conformation targeting SERM action, we observed that the pyridine group was reasonably close (5.4 Å) to the piperidine group of raloxifene to potentially form an H-bond with key amino acid Asp351. Compound 32 could also make hydrogen bonds with the key amino acids Glu353, Arg394 and His524 present in the ligand binding domain of ERα.

As will be understood by a skilled person, the invention provides for the synthesis and the in vitro assays of tetrahydroisoquinoline derivatives designed to inhibit STS and act as SERMs. The library of phenolic compounds and some sulfamate analogues were synthesized by parallel solid-phase chemistry using a multidetachable sulfamate linker. The library of phenols was tested on estrogen sensitive breast cancer T-47D cells to discard compounds bearing estrogenicity or cytotoxicity at concentrations tested.

Among compounds of the library, the phenolic derivatives 25, 29 and 31 showed no such undesirable activity and were selected for further testing. Their respective corresponding sulfamate analogues 32, 33 and 34 were tested on homogenated HEK-293 cells overexpressing STS and each showed inhibitory activity towards STS with $IC_{50}$ values of 16.6 nM, 8.9 nM and 3.9 nM, respectively. The six compounds were tested on T-47D cells and each showed no estrogenicity; some antiestrogenic activities were observed.

Following the above results, the compounds according to the invention were tested on osteoblast-like Saos-2 cells, since SERM compounds must be active in tissues where estrogenic activity is beneficial. All compounds stimulated Saos-2 cell proliferation with sulfamate compound 29 showing a higher stimulation effect. Further, we evaluated the effect of our compounds on the ALP activity of Saos-2 cells. The six compounds significantly increased the ALP activity with 29 again showing a higher stimulation effect. To make sure that the observed stimulation was mediated by estrogen receptors, we used the ERα antagonist MPP, the ERβ antagonist PHTPP and the pure antiestrogen (ICI 164,384) and investigated their effect on the stimulation induced by E2, raloxifene and compound 29. For compound 29, the induced stimulation is mediated by both estrogen subtypes with ERβ mediating the activation a bit more than ERα. Finally, we made a 3D modelization of one of the six compounds and superimposed its structure over a known potent STS inhibitor (EM-1913) and an SERM (raloxifene). The superimposition shows that our molecule could make interactions with the hydrophobic cavity in STS active site as well as key interactions with key amino acids important for the binding and the SERM activity on ERα.

Chemistry—General information: Chemical reagents were purchased from Aldrich Chemical Co. (Milwaukee, Wis., USA) and solvents were obtained from Fisher Scientific (Montreal, QC, Canada) and VWR (Ville Mont-Royal, QC, Canada). Trityl chloride resin was supplied by EMD Biosciences (Novabiochem, La Jolla, Calif., USA). Flash chromatography was performed on Silicycle 60 230-400-mesh silica gel (Québec, QC, Canada). Thin-layer chromatography (TLC) was performed on Whatman 0.25-mm silica gel 60 $F_{254}$ plates (Fisher Scientific, Nepean, ON, Canada) and compounds were visualized by exposure to UV light (254 nm), a solution of ammonium molybdate/sulphuric acid/ethanol (plus heating). Infrared (IR) spectra were recorded on an ABB MB3000 spectrometer (Québec, QC, Canada) and obtained from a thin film of the solubilized compound on NaCl pellets (usually in $CH_2Cl_2$ or acetone). Only significant bands are reported (in $cm^{-1}$). $^1H$ and $^{13}C$ NMR spectra were recorded at 400 and 100 MHz, respectively, using a Bruker AVANCE 400 spectrometer (Billerica, Mass., USA). The chemical shifts (δ) are expressed in ppm and referenced to chloroform (7.26 and 77.0 ppm), acetone (2.05 and 29.8 ppm) or methanol (3.31 and 49.0 ppm) for $^1H$ and $^{13}C$, respectively. The multiplicity signal are designed as s (singulet) d (doublet), t (triplet), q (quadruplet), p (pentaplet), m (multiplet). Low-resolution mass spectra (LRMS) were recorded on a Shimadzu Prominence apparatus (Kyoto, Japan) equipped with an atmospheric pressure chemical ionization (APCI) source on positive mode.

Example 9—Synthesis of Aldehydes Building Blocks

Aldehydes 3 and 4 were commercially available and aldehydes 1 and 2 were synthesized as follows:

To a solution of 2- or 4-hydroxy-benzaldehyde (1.64 mmol) in anhydrous acetone (25 mL) was added cesium carbonate (4.92 mmol) and the solution was stirred at room temperature for 10 min under an argon atmosphere. Chloropropylpiperidine hydrochloride (2.46 mmol) and sodium iodide (0.82 mmol) was added to the solution and the mixture was heated at reflux overnight. The resulting solution was filtered and evaporated to dryness. The crude compound was diluted with EtOAc, washed successively with a saturated carbonate solution and water, dried over $MgSO_4$, filtered and evaporated under reduce pressure. Purification by flash chromatography (hexanes/acetone/TEA: 80:19:1 to 70:29:1) yielded the desired compound 1 (360 mg, 89%), and 2 (400 mg, 99%), respectively.

2-[3-(piperidin-1-yl)propoxy]benzaldehyde (1): $^1H$ NMR (400 MHz, $CDCl_3$) δ: 1.45 (q, J=6.0 Hz, 2H), 1.59 (p, J=5.6 Hz, 4H), 2.05 (m, 2H), 2.40 (broad s, 4H), 2.50 (t, J=7.4 Hz, 2H), 4.14 (t, J=6.3 Hz, 2H), 7.01 (t, J=8.1 Hz, 2H), 7.53 (m, 1H), 7.83 (dd, J=1.8, 7.8 Hz, 1H), 10.51 (s, 1H). APCI-MS for $C_{15}H_{22}O_2N$ $[M+H]^+$: 248.3 m/z.

4-[3-(piperidin-1-yl)propoxy]benzaldehyde (2): $^1H$ NMR (400 MHz, $CDCl_3$) δ: 1.45 (m, 2H), 1.59 (q, J=5.6 Hz, 4H), 2.00 (m, 2H), 2.40 (broad s, 4H), 2.47 (t, J=7.4 Hz, 2H), 4.10 (t, J=6.4 Hz, 2H), 7.00 (d, J=8.7 Hz, 2H), 7.82 (d, J=8.7 Hz, 2H), 9.88 (s, 1H). APCI-MS for $C_{15}H_{22}O_2N$ $[M+H]^+$: 248.3 m/z.

Example 10—Synthesis of Secondary Amines 1a, 2a, 1b, 2b, 3c and 4c (General Procedure)

To a solution of aldehyde 1, 2, 3 or 4 (1.21 mmol) in absolute ethanol (12 mL) was added the appropriate amine a (1-(pyridin-2-yl)methanamine), b (1-(furan-2-yl)methanamine) or c (3-(1H imidazol-1-yl)propan-1-amine) (1.45 mmol) and 4 A° molecular sieves. The solution was stirred at room temperature for 2.5 h and filtered to remove molecular sieves. Sodium borohydride (2.90 mmol) was then added in small portion to the resulting ethanol solution at 0° C. and allowed to return at room temperature and stirred overnight. Water (15 mL) was added and the solution stirred for 15 min before to be concentrated under reduced pressure. The aqueous layer was extracted with DCM (5×5 mL), and the combined extracts was washed with brine, dried with $MgSO_4$, filtered and evaporated to dryness. Purification by flash chromatography (DCM/MeOH:TEA (98:1:1 to 90:9:1) yielded 1a (370 mg, 90%), 2a (318 mg, 78%), 1b (320 mg, 70%), 2b (347 mg, 76%), 3c (400 mg, 99%) or 4c (400 mg, 97%) according to the aldehyde and primary amine used.

1-{2-[3-(piperidin-1-yl)propoxy]phenyl}-N-(pyridin-2-ylmethyl)methanamine (1a): $^1H$ NMR (400 MHz, $CDCl_3$) δ: 1.44 (m, 2H), 1.59 (p, J=5.6 Hz, 4H), 1.89 (broad s, NH), 2.01 (m, 2H), 2.38 (broad s, 4H), 2.48 (t, J=7.5 Hz, 2H), 3.87 (s, 2H), 3.92 (s, 2H), 4.03 (t, J=6.2 Hz, 2H), 6.85 (d, J=8.0 Hz, 1H), 6.90 (t, J=7.4 Hz, 1H), 7.14 (m, 1H), 7.21 (m, 1H), 7.27 (m, 1H), 7.37 (d, J=6.8 Hz, 1H), 7.63 (td, J=1.8, 7.7 Hz, 1H), 8.54 (ddd, J=0.9, 1.8, 4.9 Hz, 1H). APCI-MS for $C_{21}H_{30}ON_3$ $[M+H]^+$: 340.3 m/z.

1-{4-[3-(piperidin-1-yl)propoxy]phenyl}-N-(pyridin-2-ylmethyl)methanamine (2a): $^1$H NMR (400 MHz, CDCl$_3$) δ: 1.45 (m, 2H), 1.60 (p, J=5.6 Hz, 4H), 1.98 (m, 2H), 2.42 (broad s, 4H), 2.49 (t, J=7.5 Hz, 2H), 3.78 (s, 2H), 3.91 (s, 2H), 4.00 (t, J=6.4 Hz, 2H), 6.85 (d, J=8.6 Hz, 2H), 7.16 (ddd, J=1.2, 4.9, 7.5 Hz, 1H), 7.25 (d, J=8.5 Hz, 2H), 7.31 (d, J=7.8 Hz, 1H), 7.64 (td, J=1.8, 7.7 Hz, 1H), 8.56 (ddd, J=1.0, 1.9, 4.9 Hz, 1H). APCI-MS for C$_{21}$H$_{30}$ON$_3$ [M+H]$^+$: 340.3 m/z.

1-(furan-2-yl)-N-{2-[3-(piperidin-1-yl)propoxy]benzyl}methanamine (1b): $^1$H NMR (400 MHz, CDCl$_3$) δ: 1.45 (m, 2H), 1.59 (p, J=5.6 Hz, 4H), 1.99 (m, 2H), 2.40 (broad s, 4H), 2.48 (t, J=7.5 Hz, 2H), 3.76 (s, 2H), 3.81 (s, 2H), 4.03 (t, J=6.2 Hz, 2H), 6.18 (dd, J=1.0, 3.2 Hz, 1H), 6.31 (dd, J=1.8, 3.1 Hz, 1H), 6.86 (d, J=8.0 Hz, 1H), 6.90 (t, J=7.4 Hz, 1H), 7.22 (m, 2H), 7.36 (dd, J=0.6, 1.6 Hz, 1H). APCI-MS for C$_{20}$H$_{29}$O$_2$N$_2$ [M+H]$^+$: 329.3 m/z.

1-(furan-2-yl)-N-{4-[3-(piperidin-1-yl)propoxy]benzyl}methanamine (2b): $^1$H NMR (400 MHz, CDCl$_3$) δ: 1.44 (m, 2H), 1.59 (p, J=5.6 Hz, 4H), 1.97 (m, 2H), 2.40 (broad s, 4H), 2.47 (t, J=7.5 Hz, 2H), 3.72 (s, 2H), 3.77 (s, 2H), 4.00 (t, J=6.4 Hz, 2H), 6.18 (dd, J=0.91, 3.2 Hz, 1H), 6.32 (dd, J=1.9, 3.2 Hz, 1H), 6.85 (d, J=8.6 Hz, 2H), 7.22 (d, J=8.6 Hz, 2H), 7.37 (dd, J=0.8, 1.9 Hz, 1H). APCI-MS for C$_{20}$H$_{29}$O$_2$N$_2$ [M+H]$^+$: 329.3 m/z.

3-(1H-imidazol-1-yl)-N-(pyridin-2-ylmethyl)propan-1-amine (3c): $^1$H NMR (400 MHz, CDCl$_3$) δ 1.97 (p, J=6.8 Hz, 2H), 2.64 (t, J=6.7 Hz, 2H), 3.88 (s, 2H), 4.06 (t, J=6.9 Hz, 2H), 6.91 (s, 1H), 7.04 (s, 1H), 7.18 (ddd, J=1.2, 4.9, 7.6 Hz, 1H), 7.26 (d, J=7.8 Hz, 1H), 7.47 (s, 1H), 7.65 (td, J=1.8, 7.7 Hz, 1H), 8.56 (m, 1H). APCI-MS for C$_{12}$H$_{17}$N$_4$ [M+H]$^+$: 217.3 m/z.

N-(furan-2-ylmethyl)-3-(1H-imidazol-1-yl)propan-1-amine (4c): $^1$H NMR (400 MHz, CDCl$_3$) δ 1.92 (p, J=6.9 Hz, 2H), 2.59 (t, J=6.7 Hz, 2H), 3.75 (s, 2H), 4.04 (t, J=6.9 Hz, 2H), 6.15 (dd, J=0.6, 3.2 Hz, 1H), 6.32 (dd, J=1.9, 3.2 Hz, 1H), 6.89 (t, J=1.3 Hz, 1H), 7.05 (s, 1H), 7.37 (dd, J=0.8, 1.8 Hz, 1H), 7.45 (s, 1H). APCI-MS for C$_{11}$H$_{16}$ON$_3$ [M+H]$^+$: 206.3 m/z.

Example 11—Synthesis of Phenol Library

The compounds 19-31 were synthesized in good quantity (28 to 39 mg) following the strategy we previously developed and published for similar phenolic derivatives.[16] All these compounds were purified by reverse phase on LC-MS preparative system (Model Prominence, Shimadzu, Kyoto, Japan) equipped with a photodiode detector (SPD M 20A) and mass analyser (MS 2020) with atmospheric-pressure chemical positive ionisation (APCI) systems with a synergy C18 column (250×21.2 mm×4 μM). These compounds were purified in 50 min using a solvent gradient already established (70-100% MeOH, 30-0% water) at flow rate of 10 mL/min at room temperature.

(7-hydroxy-3,4-dihydroisoquinolin-2(1H)-yl)(4-{[{2-[3-(piperidin-1-yl)propoxy]benzyl}(pyridin-2-ylmethyl)amino]methyl}phenyl)methanone (19): $^1$H NMR (400 MHz, CD$_3$OD) δ: 1.48 (broad s, 2H), 1.60 (q, J=4.7, 5.3 Hz, 4H), 1.97 (m, 2H), 2.47 (broad s, 4H), 2.54 (t, J=7.6 Hz, 2H), 2.76 (broad s, 1H), 2.85 (broad s, 1H), 3.58 (broad s, 1H), 3.70 (s, 2H), 3.71 (s, 2H), 3.76 (s, 2H), 3.91 (broad s, 1H), 4.02 (t, J=6.1 Hz, 2H), 4.50 (s, 1H), 4.74 (s, 1H), 6.63 (d, J=7.5 Hz, 2H), 6.94 (m, 2H), 6.97 (d, J=7.8 Hz, 1H), 7.18 (td, J=1.5, 7.7 Hz, 1H), 7.26 (m, 1H), 7.38 (d, J=6.4 Hz, 2H), 7.46 (d, J=6.3 Hz, 1H), 7.51 (d, J=7.9 Hz, 1H), 7.70 (dt, J=1.2, 8.0 Hz, 1H), 7.79 (td, J=1.80, 7.7 Hz, 1H), 8.40 (d, J=4.4 Hz, 1H). APCI-MS for C$_{38}$H$_{45}$O$_3$N$_4$ [M+H]$^+$: 605.4 m/z. HPLC purity of 91.0%.

(7-hydroxy-3,4-dihydroisoquinolin-2(1H)-yl)(4-{[{4-[3-(piperidin-1-yl)propoxy]benzyl}(pyridin-2-ylmethyl)amino]methyl}phenyl)methanone (20): $^1$H NMR (400 MHz, CD$_3$OD) δ: 1.53 (d, J=6.6 Hz, 2H), 1.67 (p, J=5.8 Hz, 4H), 2.02 (p, J=6.1 Hz, 2H), 2.68 (m, 6H), 2.76 (broad s, 2H), 2.85 (broad s, 1H), 3.56 (s, 2H), 3.59 (m, 1H), 3.63 (s, 2H), 3.71 (s, 2H), 3.91 (s, 1H), 4.05 (t, J=6.0 Hz, 2H), 4.50 (s, 1H), 4.75 (s, 1H), 6.63 (d, J=6.3 Hz, 2H), 6.87 (d, J=8.6 Hz, 2H), 6.97 (d, J=7.2 Hz, 1H), 7.29 (m, 3H), 7.40 (d, J=7.3 Hz, 2H), 7.50 (d, J=7.8 Hz, 2H), 7.68 (d, J=7.8 Hz, 1H), 7.82 (td, J=1.8, 7.7 Hz, 1H), 8.41 (d, J=4.4 Hz, 1H). APCI-MS for C$_{38}$H$_{45}$O$_3$N$_4$ [M+H]$^+$: 605.4 m/z. HPLC purity of 90.0%.

4-{[(furan-2-ylmethyl){2-[3-(piperidin-1-yl)propoxy]benzyl}amino]methyl}phenyl)(7-hydroxy-3,4-dihydroisoquinolin-2(1H)-yl)methanone (21): $^1$H NMR (400 MHz, CD$_3$OD) δ: 1.67 (broad s, 2H), 1.85 (broad s, 4H), 2.11 (dq, J=5.88, 11.4 Hz, 2H), 2.77 (broad s, 1H), 2.86 (broad s, 1H), 3.14 (m, 2H), 3.61 (broad s, 1H), 3.67 (s, 2H), 3.68 (s, 2H), 3.70 (s, 2H), 3.93 (broad s, 1H), 3.93 (t, J=6.2 Hz, 1H), 4.05 (t, J=5.8 Hz, 2H), 4.51 (s, 1H), 4.77 (s, 1H), 6.28 (d, J=3.0 Hz, 2H), 6.38 (d, J=3.1 Hz, 2H), 6.63 (d, J=6.6 Hz, 2H), 6.95 (m, 4H), 7.23 (td, J=1.6, 7.7 Hz, 1H), 7.40 (d, J=7.5 Hz, 2H), 7.49 (m, 4H). APCI-MS for C$_{37}$H$_{44}$O$_4$N$_3$ [M+H]$^+$: 594.4 m/z. HPLC purity of 89.9%.

(4-{[(furan-2-ylmethyl){4-[3-(piperidin-1-yl)propoxy]benzyl}amino]methyl}phenyl)(7-hydroxy-3,4-dihydroisoquinolin-2(1H)-yl)methanone (22): $^1$H NMR (400 MHz, CD$_3$OD) δ: 1.51 (d, J=5.9 Hz, 2H), 1.64 (p, J=5.6 Hz, 4H), 2.00 (dq, J=6.05, 11.9 Hz, 2H), 2.61 (m, 6H), 2.77 (broad s, 2H), 2.86 (broad s, 1H), 3.54 (s, 2H), 3.60 (s, 2H), 3.62 (m, 3H), 3.92 (s, 1H), 4.01 (t, J=6.1 Hz, 2H), 4.52 (s, 1H), 4.76 (s, 1H), 6.24 (dd, J=0.9, 3.3 Hz, 1H), 6.36 (dd, J=1.9, 3.2 Hz, 1H), 6.63 (d, J=6.2 Hz, 2H), 6.86 (d, J=8.6 Hz, 2H), 6.98 (d, J=8.0 Hz, 1H), 7.28 (d, J=8.6 Hz, 2H), 7.40 (d, J=6.7 Hz, 2H), 7.49 (m, 3H). APCI-MS for C$_{37}$H$_{44}$O$_4$N$_3$ [M+H]$^+$: 594.5 m/z. HPLC purity of 92.0%.

(7-hydroxy-3,4-dihydroisoquinolin-2(1H)-yl)[4-({[3-(1H-imidazol-1-yl)propyl](pyridin-2-ylmethyl)amino}methyl)phenyl]methanone (23): $^1$H NMR (400 MHz, CD$_3$OD) δ: 2.01 (p, J=6.9 Hz, 2H), 2.51 (t, J=6.8 Hz, 2H), 2.77 (broad s, 1H), 2.86 (broad s, 1H), 2.86 (t, J=6.1 Hz, 1H), 3.60 (br t, J=5.0 Hz, 1H), 3.68 (s, 2H), 3.74 (s, 2H), 3.92 (br t, J=5.0 Hz, 1H), 4.02 (t, J=6.9 Hz, 2H), 4.50 (s, 1H), 4.76 (s, 2H), 6.63 (d, J=6.4 Hz, 2H), 6.88 (s, 1H), 6.98 (m, 2H), 7.30 (ddd, J=1.3, 5.0, 7.5 Hz, 1H), 7.40 (d, J=6.0 Hz, 2H), 7.49 (m, 2H), 7.59 (dt, J=1.1, 7.9 Hz, 1H), 7.82 (td, J=1.8, 7.7 Hz, 1H), 8.44 (ddd, J=0.9, 1.8, 5.1 Hz, 1H). APCI-MS for C$_{29}$H$_{32}$O$_2$N$_5$ [M+H]$^+$: 482.3 m/z. HPLC purity of 99.0%.

[4-({(furan-2-ylmethyl)[3-(1H-imidazol-1-yl)propyl]amino}methyl)phenyl](7-hydroxy-3,4-dihydroisoquinolin-2(1H)-yl)methanone (24): $^1$H NMR (400 MHz, CD$_3$OD) δ: 1.99 (p, J=6.8 Hz, 2H), 2.47 (t, J=6.7 Hz, 2H), 2.77 (broad s, 1H), 2.86 (broad s, 1H), 3.65 (m, 5H), 3.93 (broad s, 1H), 4.07 (t, J=6.8 Hz, 2H), 4.52 (s, 1H), 4.77 (s, 1H), 6.23 (d, J=3.2 Hz, 1H), 6.35 (dd, J=1.9, 3.2 Hz, 1H), 6.63 (d, J=5.2 Hz, 2H), 6.93 (s, 1H), 7.00 (m, 1H), 7.03 (s, 1H), 7.46 (m, 5H), 7.59 (s, 1H). APCI-MS for C$_{23}$H$_{31}$O$_3$N$_4$ [M+H]$^+$: 471.3 m/z. HPLC purity of 90.0%.

(4-{[(furan-2-ylmethyl)(pyridin-2-ylmethyl)amino]methyl}phenyl)(7-hydroxy-3,4-dihydroisoquinolin-2(1H)-yl)methanone (25): $^1$H NMR (400 MHz, CD$_3$OD) δ: 2.77 (broad s, 1H), 2.86 (broad s, 1H), 3.60 (s, 1H), 3.70 (s, 2H), 3.71 (s, 2H), 3.80 (s, 2H), 3.91 (s, 1H), 4.51 (s, 1H), 4.75 (s, 1H), 6.26 (d, J=3.1 Hz, 1H), 6.35 (dd, J=1.8, 3.2 Hz, 1H), 6.63 (d, J=4.6 Hz, 2H), 6.98 (d, J=7.1 Hz, 1H), 7.28 (m, 1H), 7.40 (d, J=6.1 Hz, 2H), 7.47 (s, 1H), 7.51 (d, J=7.9 Hz, 2H), 7.69 (d, J=7.9 Hz, 1H), 7.81 (td, J=1.8, 7.7 Hz, 1H), 8.42 (d, J=4.6 Hz, 1H). APCI-MS for $C_{28}H_{28}O_3N_3$ [M+H]$^+$: 454.2 m/z. HPLC purity of 94.7%.

(4-{[(4-bromobenzyl)(furan-2-ylmethyl)amino]methyl}phenyl)(7-hydroxy-3,4-dihydroisoquinolin-2(1H)-yl)methanone (26): $^1$H NMR (400 MHz, CD$_3$OD) δ: 2.77 (t, J=5.6 Hz, 1H), 2.86 (s, 1H), 3.55-3.95 (m, 8H), 4.51 (s, 1H), 4.76 (s, 1H), 6.33 (s, 1H), 6.40 (s, 1H), 6.63 (d, J=4.4 Hz, 2H), 6.98 (d, J=7.9 Hz, 1H), 7.33 (d, J=8.2 Hz, 2H), 7.40-7.55 (m, 7H). APCI-MS for $C_{29}H_{28}BrO_3N_2$ [M+H]$^+$: 531.5 and 533.5 m/z. HPLC purity of 97.1%.

[4-({(furan-2-ylmethyl)[2-(morpholin-4-yl)ethyl]amino}methyl)phenyl](7-hydroxy-3,4-dihydroisoquinolin-2(1H)-yl)methanone (27): $^1$H NMR (400 MHz, CD$_3$OD) δ: 2.44 (s, 4H), 2.53 (dd, J=5.7, 8.2 Hz, 2H), 2.66 (dd, J=5.8, 8.4 Hz, 2H), 2.77 (broad s, 1H), 2.86 (s, 1H), 3.65 (m, 4H), 3.70 (s, 4H), 3.92 (broad s, 1H), 4.53 (s, 1H), 4.65-4.77 (s, 1H), 6.27 (d, J=3.2 Hz, 1H), 6.36 (d, J=2.9 Hz, 1H), 6.63 (d, J=6.1 Hz, 2H), 6.98 (d, J=7.1 Hz, 2H), 7.39-7.54 (m, 6H). APCI-MS for $C_{28}H_{34}O_4N_3$ [M+H]$^+$: 476.4 m/z. HPLC purity of 91.0%.

(7-hydroxy-3,4-dihydroisoquinolin-2(1H)-yl)[4-({[(5-methylthiophen-2-yl)methyl](pyridin-2-ylmethyl)amino}methyl)phenyl]methanone (28): $^1$H NMR (400 MHz, CD$_3$OD) δ: 2.44 (d, J=1.2 Hz, 3H), 2.76 (t, J=5.7 Hz, 1H), 2.85 (broad s, 1H), 3.60 (broad s, 1H), 3.69 (s, 2H), 3.75 (2s, 4H), 3.90 (broad s, 1H), 4.50 (s, 1H), 4.75 (s, 1H), 6.62 (m, 3H), 6.74 (d, J=3.3 Hz, 1H), 6.97 (d, J=7.5 Hz, 1H), 7.28 (ddd, J=1.3, 5.0, 7.4 Hz, 1H), 7.40 (d, J=6.5 Hz, 2H), 7.54 (d, J=7.8 Hz, 2H), 7.73 (dt, J=1.1, 7.9 Hz, 1H), 7.83 (td, J=1.8, 7.7 Hz, 1H), 8.42 (ddd, J=0.89, 1.7, 5.1 Hz, 1H). APCI-MS for $C_{29}H_{30}O_2N_3S$ [M+H]$^+$: 484.2 m/z. HPLC purity of 99.4%.

[4-({(furan-2-ylmethyl)[(5-methylthiophen-2-yl)methyl]amino}methyl)phenyl](7-hydroxy-3,4-dihydroisoquinolin-2(1H)-yl)methanone (29): $^1$H NMR (400 MHz, CD$_3$OD) δ: 2.44 (s, 3H), 2.78 (broad s, 1H), 2.86 (broad s, 1H), 3.65 (m, 5H), 3.74 (s, 2H), 3.92 (s, 1H), 4.53 (s, 1H), 4.76 (s, 1H), 6.26 (d, J=3.1 Hz, 1H), 6.37 (dd, J=1.9, 3.2 Hz, 1H), 6.60 (m, 3H), 6.73 (d, J=3.4 Hz, 1H), 6.98 (d, J=7.4 Hz, 1H), 7.44 (m, 3H), 7.53 (d, J=7.7 Hz, 2H). APCI-MS for $C_{28}H_{29}O_3N_2S$ [M+H]$^+$: 473.3 m/z. HPLC purity of 98.1%.

(4-{[(furan-2-ylmethyl)(4-hydroxybenzyl)amino]methyl}phenyl)(7-hydroxy-3,4-dihydroisoquinolin-2(1H)-yl)methanone (30): $^1$H NMR (400 MHz, CD$_3$OD) δ: 2.77 (t, J=5.7 Hz, 2H), 2.86 (broad s, 1H), 3.49 (s, 2H), 3.62 (3s, 6H), 3.92 (broad s, 1H), 4.52 (s, 1H), 4.76 (s, 1H), 6.23 (d, J=3.0 Hz, 1H), 6.36 (dd, J=1.9, 3.1 Hz, 1H), 6.63 (m, 2H), 6.74 (d, J=8.0 Hz, 2H), 6.97 (d, J=7.1 Hz, 2H), 7.19 (d, J=8.3 Hz, 2H), 7.40 (d, J=6.9 Hz, 2H), 7.49 (t, J=8.1 Hz, 3H). APCI-MS for $C_{29}H_{29}O_4N_2$ [M+H]$^+$: 469.2 m/z. HPLC purity of 89.3%.

(7-hydroxy-3,4-dihydroisoquinolin-2(1H)-yl)(4-{[(4-methoxybenzyl)(pyridin-2-ylmethyl)amino]methyl}phenyl)methanone (31): $^1$H NMR (400 MHz, CD$_3$OD) δ: 2.76 (broad s, 1H), 2.85 (broad s, 1H), 3.56 (s, 2H), 3.59 (broad s, 1H), 3.64 (s, 2H), 3.71 (s, 2H), 3.76 (s, 3H), 3.91 (broad s, 1H), 4.50 (s, 1H), 4.75 (s, 1H), 6.62 (broad s, 2H), 6.87 (d, J=8.6 Hz, 2H), 6.98 (d, J=8.1 Hz, 1H), 7.29 (m, 3H), 7.40 (m, 2H), 7.51 (d, J=7.8 Hz, 2H), 7.69 (d, J=7.9 Hz, 1H), 7.82 (td, J=1.78, 7.7 Hz, 1H), 8.40 (d, J=4.4 Hz, 1H). APCI-MS for $C_{31}H_{32}O_3N_3$ [M+H]$^+$: 494.3 m/z. HPLC purity of 98.3%.

Example 12—Synthesis of Sulfamates 32-34

General procedure: The compounds 32-34 were synthesized following the strategy we previously developed and published for similar sulfamate derivatives.[16] The compounds were purified by flash chromatography.

2-[(4-{[(furan-2-yl methyl)(pyridin-2-yl methyl)amino]methyl}phenyl)carbonyl]-1,2,3,4-tetrahydroisoquinolin-7-yl sulfamate (32): $^1$H NMR (400 MHz, CDCl$_3$) δ: 2.88 (m, 2H), 3.70 (m, 6H), 3.82 (s, 2H), 3.98 (broad s, 1H), 4.60 (broad s, 1H), 4.88 (broad s, 1H), 5.12 (broad s, 2H), 6.22 (dd, J=0.9, 3.2 Hz, 1H), 6.33 (dd, J=1.8, 3.2 Hz, 1H), 7.18 (m, 4H), 7.44 (m, 5H), 7.58 (d, J=7.8 Hz, 1H), 7.69 (td, J=1.8, 7.7 Hz, 1H), 8.53 (dd, J=1.5, 4.7 Hz, 1H). APCI-MS for $C_{28}H_{29}O_5N_4S$ [M+H]$^+$: 533.3 m/z. HPLC purity of 79.9%.

2-{[4-({(furan-2-ylmethyl)[(5-methylthiophen-2-yl)methyl]amino}methyl)phenyl]carbonyl}-1,2,3,4-tetrahydroisoquinolin-7-yl sulfamate (33): $^1$H NMR (400 MHz, CDCl$_3$) δ: 2.47 (s, 3H), 2.84 (m, 2H), 3.66 (s, 2H), 3.69 (s, 2H), 3.77 (s, 2H), 3.98 (broad s, 1H), 4.64 (broad s, 1H), 4.89 (broad s, 2H), 5.00 (m, 2H), 6.22 (dd, J=0.83, 3.1 Hz, 1H), 6.35 (dd, J=1.8, 3.2 Hz, 1H), 6.59 (dd, J=1.4, 3.3 Hz, 1H), 6.72 (d, J=3.4 Hz, 1H), 7.15 (m, 3H), 7.42 (d, J=8.0 Hz, 3H), 7.50 (d, J=8.0 Hz, 2H). APCI-MS for $C_{28}H_{30}O_5N_3S_2$ [M+H]$^+$: 552.3 m/z. HPLC purity of 90.9%.

2-[(4-{[(4-methoxybenzyl)(pyridin-2-yl methyl)amino]methyl}phenyl)carbonyl]-1,2,3,4-tetrahydroisoquinolin-7-yl sulfamate (34): $^1$H NMR (400 MHz, CDCl$_3$) δ: 2.89 (m, 2H), 3.57 (s, 2H), 3.64 (m, 3H), 3.74 (s, 2H), 3.80 (s, 3H), 3.91 (broad s, 1H), 4.59 (s, 1H), 4.8-5.2 (m, 3H), 6.87 (d, J=8.6 Hz, 2H), 7.17 (m, 4H), 7.31 (d, J=8.6 Hz, 2H), 7.39 (m, 2H), 7.46 (m, 2H), 7.58 (d, J=7.9 Hz, 1H), 7.68 (td, J=1.8, 7.7 Hz, 1H), 8.51 (dt, J=1.3, 5.0 Hz, 1H). APCI-MS for $C_{31}H_{33}O_5N_4S$ [M+H]$^+$: 573.3 m/z. HPLC purity of 83.0%.

Biological Assays

Example 13—Chemicals and Reagents

17β-estradiol, Tris, EDTA, glycerol, insulin and bovine serum albumin (BSA) were purchased from Sigma-Aldrich Canada Ltd (Oakville, ON). 3-(4,5-dimethylthiazol-2-yl)-5-(3-carboxymethoxyphenyl)-2-(4-sulfophenyl)-2H tetrazolium, inner salt (MTS) was purchased from Promega (Madison, Wis.). Radiolabeled [6,7-$^3$H] estrone sulfate (54.3 Ci/mmol) was purchased from Perkin Elmer (Woodbridge, ON, Canada). Raloxifene hydrochloride was bought from Cayman Chemical (Ann Harbor, Mich.). Biodegradable Counting Scintillant was purchased from Amersham Biosciences. The two selective estrogen receptor antagonists, 1,3-bis(4-hydroxyphenyl)-4-methyl-5-[4-(2-piperidinylethoxy)phenol]-1H pyrazole dihydrochloride (MPP) and 4-[2-phenyl-5,7-bis(trifluoromethyl)pyrazolo[1,5-a]pyrimidin-3-yl]phenol (PHTPP), were purchased from Tocris Biosciences (Minneapolis, Minn.). Penicillin/streptomycin mix, L-glutamine, non-essential amino acids, sodium pyruvate, normal and charcoal-stripped Fetal Bovine Serum (FBS) and geneticin (G418 sulfate) were purchased from Wisent, Inc. (St-Bruno, QC, Canada). All cell culture medias were purchased from Life Technologies (Grand Island, N.Y.) except for phenol-red free McCoy's 5A medium that was purchased from PromoCell (Heidelberg, Germany). STS inhibitor EM-1913 and pure antiestrogen ICI-164,384 (EM-100) were synthesized in our Laboratory of Medicinal Chemistry using published procedure.[55,71]

For the purpose of in vitro assays, all chemicals tested (inhibitors and reference compounds) were first dissolved in DMSO and subsequent dilutions were done in the proper buffer or cell culture media. The final concentration of DMSO in the culture medium was 0.1% or less.

Example 14—Cell Culture

The ER$^+$ breast cancer cell line T-47D and the osteoblast-like Saos-2 cells were purchased from the American Type Culture Collection (ATCC) (Manassas, Va.). The HEK-293 cell line overexpressing STS was obtained from Dr. Van Luu-The (CHUQ-CHUL Research Center).[69] All cell lines were maintained in culture flasks (175 cm$^2$ growth area, BD Falcon) at 37° C. in a 5% $CO_2$ humidified atmosphere. The T-47D cells were grown in phenol red free RPMI 1640 medium supplemented with 10% FBS, penicillin (100 IU/mL), streptomycin (100 µg/mL), L-glutamine (2 mM) and 17β-estradiol (1 nM). The Saos-2 cells were grown in phenol red free McCoy's 5A medium supplemented with 10% FBS, penicillin (100 IU/mL) and streptomycin (100 µg/mL). The HEK-293 cells transfected with STS were maintained in Minimum Essential Medium supplemented with 10% FBS, penicillin (100 IU/mL), streptomycin (100 µg/mL), L-glutamine (2 mM), non-essential amino acids (0.1 mM), sodium pyruvate (1 mM) and geneticin (G418 sulfate) (700 µg/mL).

Example 15—Steroid Sulfatase (STS) Inhibition Assay

An enzymatic assay previously described was used for the inhibition of the transformation of estrone sulfate (E1S) to estrone (E1) by STS.[72] Briefly, the transfected HEK-293 cells were homogenized by repeated (5 times) cycles of freezing (−80° C.) and thawing on ice (4° C.). The homogenates were then incubated for 2 h at 37° C. (shaking water bath) with or without inhibitors (0.01 µM-1 µM) in presence of [$^3$H]-E1S (9 nM), adjusted to 1 µM with E1S, in a Tris-acetate buffer (pH 7.4) containing 5 mM EDTA and 10% glycerol. After the incubation, 1 mL of xylene was added to each tube and the solutions were then centrifuged at 3000 rpm for 20 min to separate the organic ([$^3$H]-E1) and aqueous ([$^3$H]-E1S) phases. Once 500 µL of each phase was added to 10 mL of Biodegradable Counting Scintillant, the radioactivity of samples was recorded using a Wallac 1411 Liquid Scintillation Counter. The percentage of inhibition was determined by comparison with the control (buffer+homogenate+[$^3$H]-E1S) which was set to 0% of inhibition. $IC_{50}$ value was obtained using GraphPad Prism 5 (GraphPad Software, La Jolla, Calif.).

Example 16—Cell Proliferation

CellTitter 96® Aqueous One Solution Cell Proliferation Assay was used as an indirect colorimetric measurement of cell proliferation according to the manufacturer's instructions. Briefly, after the treatments, 20 µL of MTS solution was added to each well (100 µL) of the plates and incubated at 37° C. for 2 h (Saos-2) or 4 h (T-47D). The absorbance at 490 nm was then measured with a Thermo max microplate reader (Molecular Devices, Sunnyvale, Calif.). The control (culture media+DMSO) is set to 100% of cell proliferation.

Example 17—T-47D Cells

T-47D cells were suspended in RPMI supplemented with insulin (50 ng/ml), instead of 17β-estradiol, and 5% charcoal-stripped FBS to deprive the media of estrogens. The cells were plated in 96-well plates at a density of 3 000 cells/well and allowed to attach for 48 h. After this pre-incubation, the inhibitors and the reference compounds diluted in fresh culture media were added to the wells and replaced every 2 days for 7 days of treatment.

Example 18—Saos-2 Cells

Saos-2 cells were suspended in phenol-red free McCoy's 5A medium supplemented with 10% charcoal-stripped FBS, penicillin (100 IU/mL) and streptomycin (100 µg/mL). The cells were seeded in 96-well plates at a density of 3 000 cells/well and allowed to attach. After 24 h, the inhibitors and the reference compounds diluted in fresh culture media were added to the wells and replaced every 2 days for 7 days of treatment.

Example 19—Alkaline Phosphatase (ALP) Activity

Saos-2 cells were treated similarly as reported in the cell proliferation assay. The cells were seeded at a density of 2 000 cells/well and were treated with the inhibitors and the reference compounds for 3 days. The alkaline phosphatase (ALP) activity was measured using Sensolyte® pNPP Alkaline Phosphatase Assay Kit *Colorimetric* (AnaSpec, Fremont, Calif.) following the manufacturer's protocol. Briefly, after the 3 days of treatment, the cells were washed twice with washing buffer (provided with the kit) and lysed with 0.2% Triton X-100. The cell lysates were centrifuged and the supernatants were used to determine the ALP activity. The supernatants were deposed in a 96-well plate and incubated 30 min with a p-nitrophenyl phosphate solution (provided with the kit). The absorbance at 405 nm was measured with a Thermo max microplate reader (Molecular Devices, Sunnyvale, Calif.). The control (culture media+DMSO) is set to 100% of alkaline phosphatase activity.

Other compounds were prepared as outlined in Schemes 3 and 4 below.

Amide Derivatives 8 and 9 in Scheme 3 Below

Figure 11:
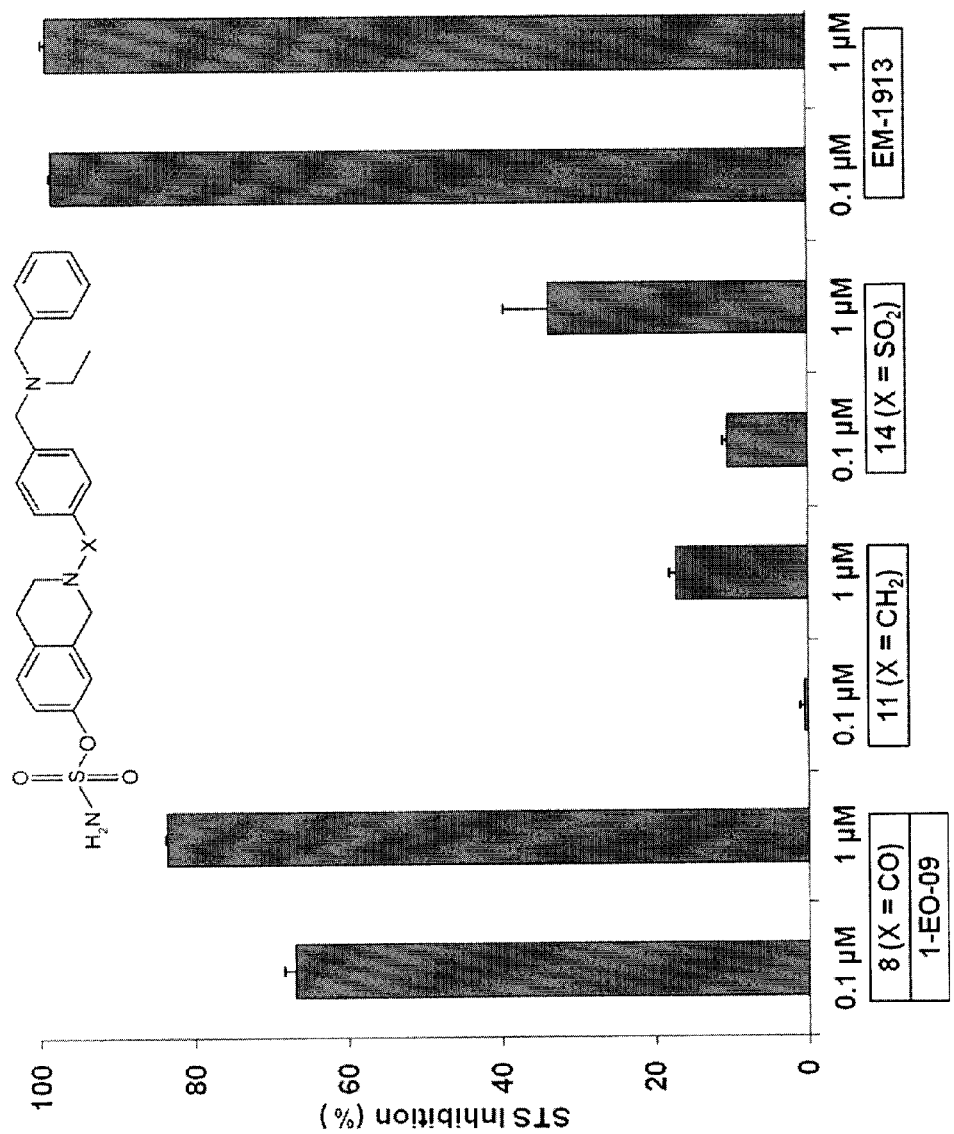
FIG. 11 illustrates the effect of amide (X=CO), amine (X=CH$_2$) and sulfonamide (X=SO$_2$) on STS inhibition. EM-1913 is a potent inhibitor of STS used as reference compound.[55]
Figure 12:
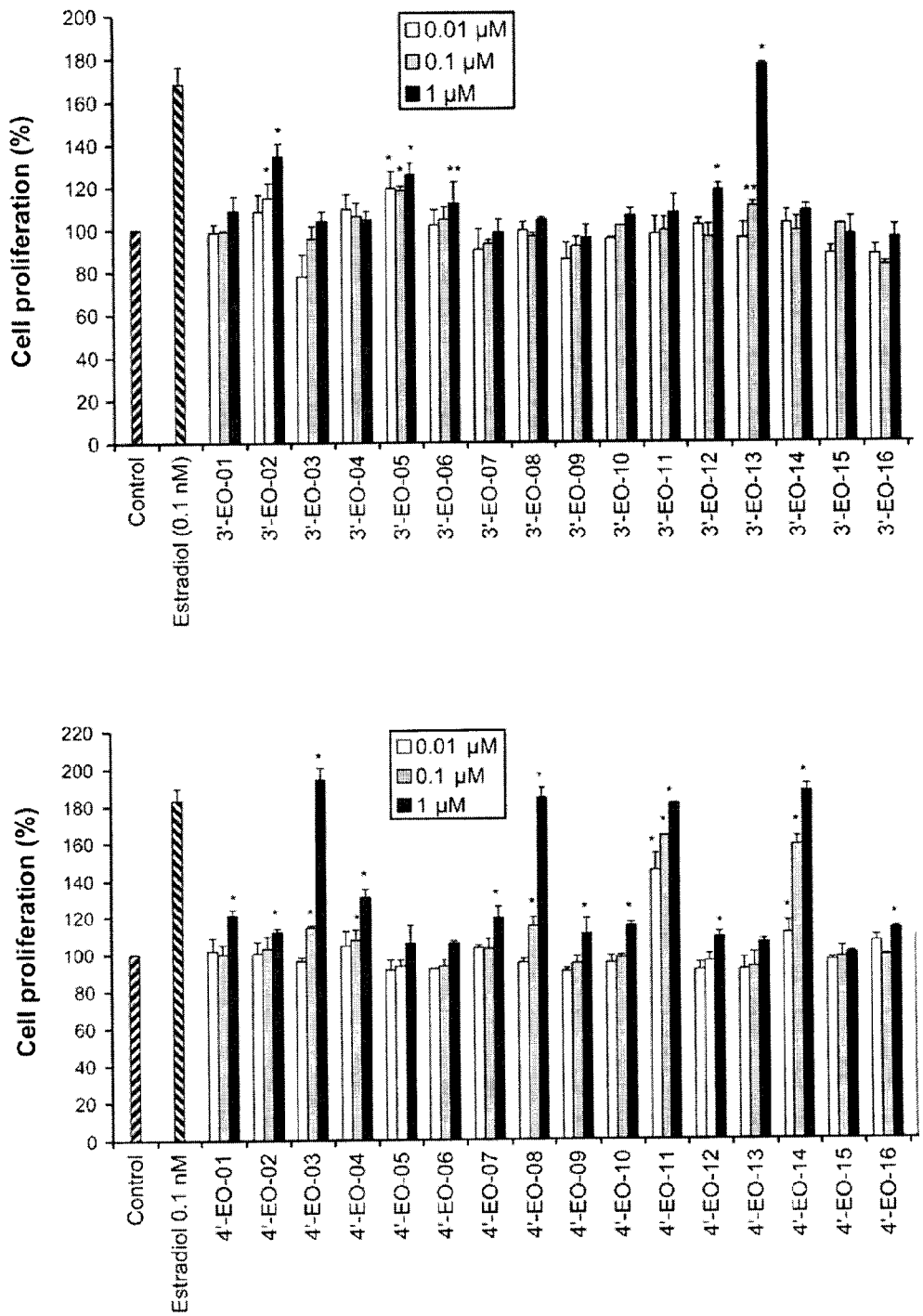
FIG. 12 illustrates the effect of estradiol and the phenol derivatives of libraries 3'-EO (upper) and 4'-EO (lower) on the growth of estrogen-starved MCF-7 (ER$^+$) cells after 7 days of treatment. Control is fixed at 100% of cell proliferation. The potent natural estrogen estradiol was used as a reference compound. Results are expressed as mean±SEM of one experiment in triplicate. **=P<0.05 vs. control; *=P<0.01 vs. control.
Figure 13:
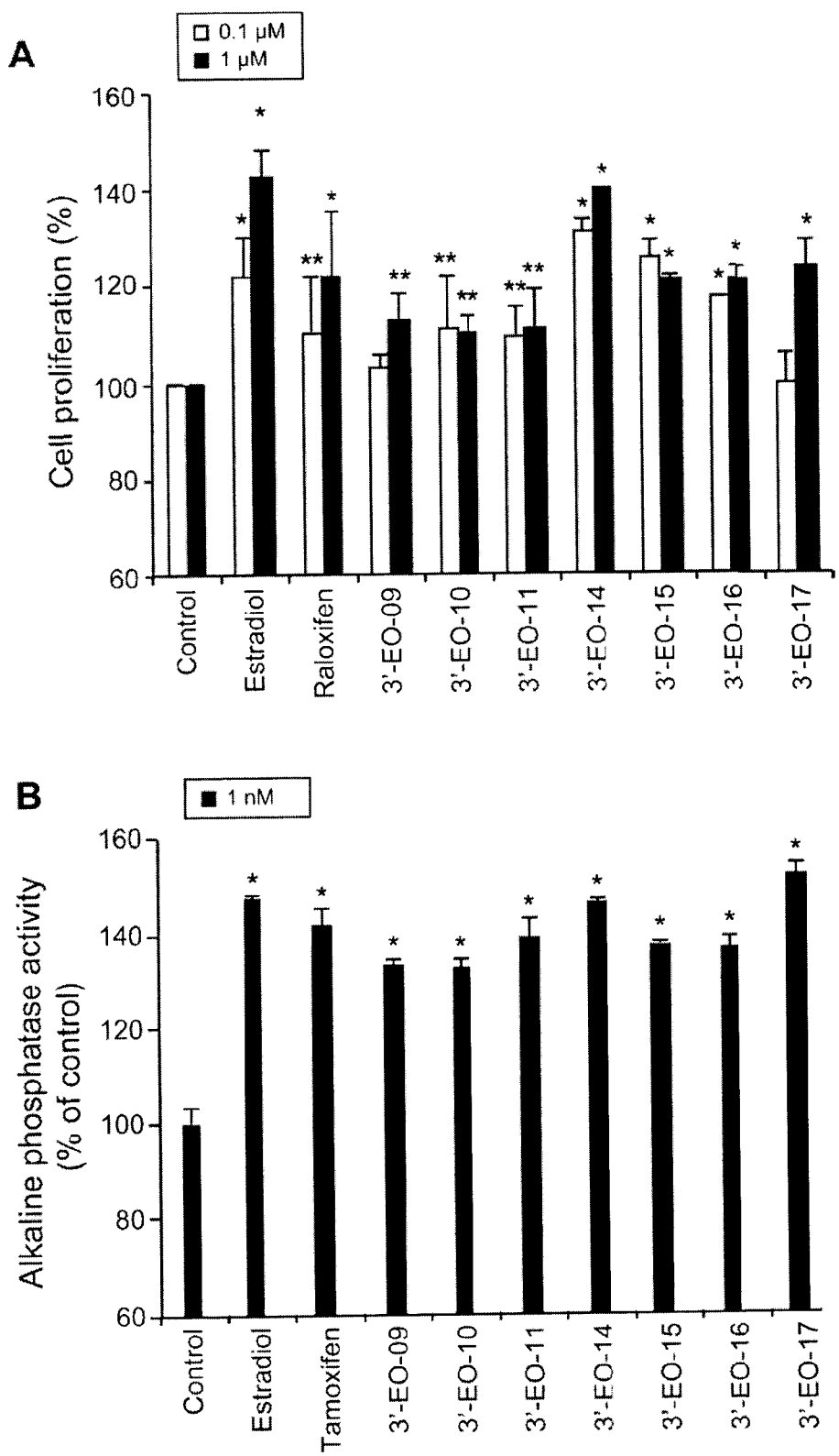
FIG. 13 illustrates the effect of estradiol, raloxifen and phenol derivatives 3'-EO-9 to 11 and 3'-EO-14 to 17 on the growth (A) and alkaline phosphatase activity (B) of estrogen-starved Saos-2 cells (ER$^+$) after 7 days of treatment. Control is fixed at 100% of cell proliferation. The potent natural estrogen estradiol and the SERM raloxifen were used as a reference compounds. Results are expressed as mean±SEM of one experiment in triplicate. **=P<0.05 vs. control; *=P<0.01 vs. control.

The general synthetic methodology for the preparation of all library members is outlined in Scheme 3. The starting compound 1,2,3,4-tetrahydroisoquinolin-7-ol (1) was selectively protected as the N-Fmoc derivative 2, which after a sulfamoylation of the phenol yielded the sulfamate 3. This sulfamate derivative was then reacted with the trityl chloride resin to give the solid-phase bounded compound 4. Deprotection of the N-Fmoc provided resin 5 with a free NH, which can be diversified with various spacers or different side chains. Since the first spacer considered was a benzamide, resin 6 was obtained by acylation of resin 5 with carboxybenzaldehyde. Another level of diversity was then added by performing a reductive amination of resin 6 with various secondary amines that yielded resin 7. Finally, both the sulfamate derivatives 8 and the phenol derivatives 9 were obtained by cleavage from the solid support using acidic and nucleophilic conditions, respectively. We thus generated four libraries (1-EO, 2-EO, 3-EO and 4-EO; 54 sulfamate derivatives) as potential STS inhibitors (Table 2, Table 3 and FIG. 11) and two libraries (3'-EO and 4'-EO; 34 phenol derivatives) as potential SERM (FIGS. 12 and 13). For libraries 1, 3 and 3', the secondary amine is in para position relative to the benzamide group, whereas for libraries 2, 4 and 4', the secondary amine is in meta position.

Scheme 3 Synthetic route to obtaining sulfamate derivatives 8 (Libraries 1-4) and phenol derivatives 9 (Libraries 3′ and 4′).

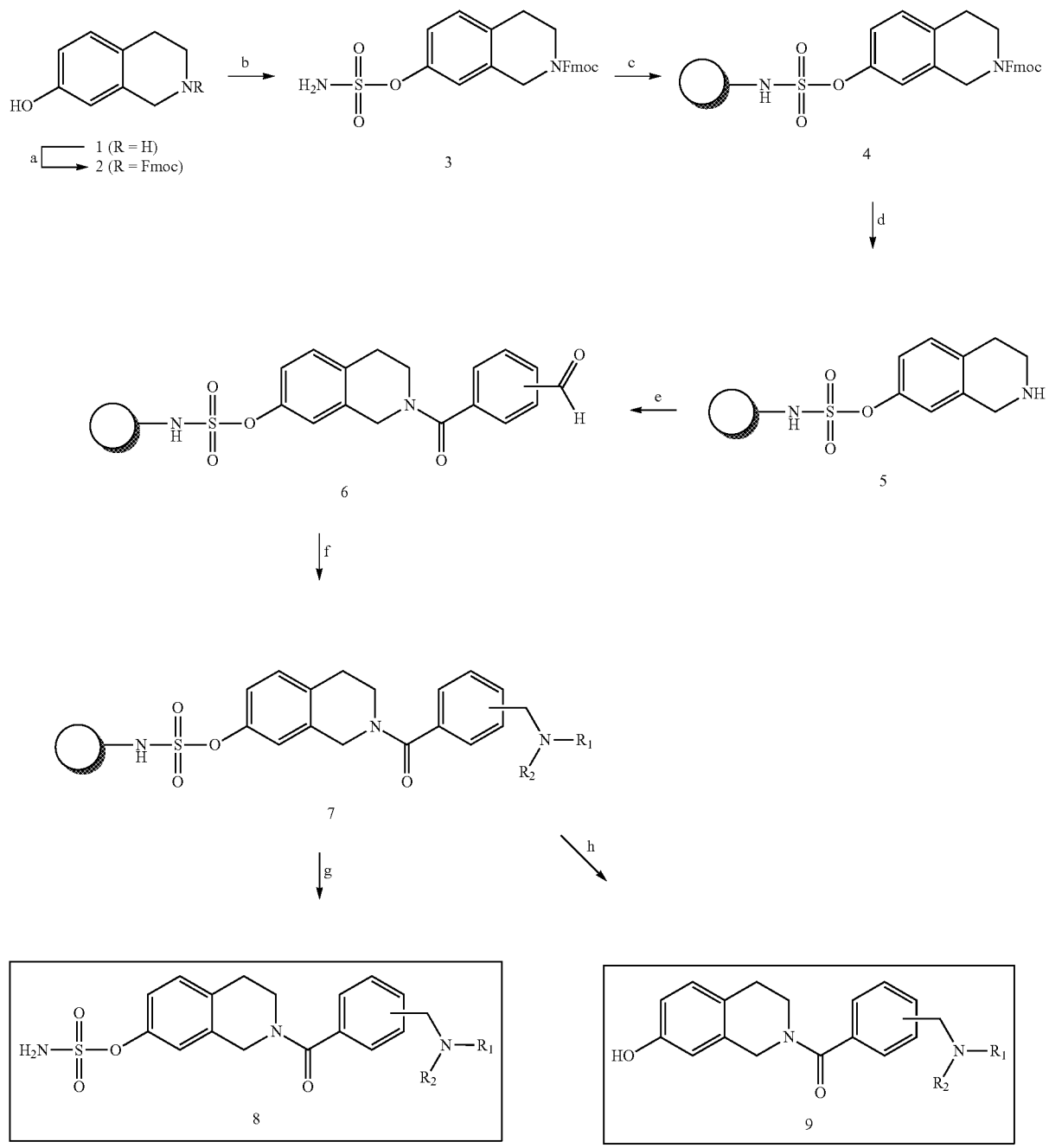

Reagents and conditions: (a) Fmoc-O-succinimide, NaHCO$_3$, H$_2$O; (b) NH$_2$SO$_2$Cl, 2,6-tert-butyl-4-methylpyridine, DCM; (c) trityl chloride resin, DIPEA, DMA/DCM; (d) 20% piperidine in DMF; (e) carboxybenzaldehyde, DIPEA, HOBt, PyBOP, DMF; (f) secondary amine (R$_1$R$_2$NH), NaBH(OAc)$_3$, 10% AcOH in NMP; (g) 30% HFIP in DCM; (h) 30% DEA in THF, 60° C.

Amine and Sulfonamide Derivatives 11 and 14 in Scheme 4 Below

In order to determine the relative importance of chemical functionality on inhibitory activity (amide, amine, sulfonamide) at the junction point between the tetrahydroisoquinoline and the substituted benzylamine moiety, we synthesized the amine and sulfonamide analogs of the best amide derivative (1-EO-9) of library 1 (Scheme 4). The amine 11 was obtained by first performing a reductive amination on resin 5 using the N-ethylbenzylamine-benzaldehyde building block to give the corresponding amine intermediate 10, which was then submitted to an acidic cleavage to release the corresponding sulfamate 11. On the other side, the sulfonamide 14 was obtained by having the amine resin 5 react with the 4-sulfonylchloride benzaldehyde to give the aldehyde intermediate resin 12, which was then submitted to a reductive amination with N-ethylbenzylamine to provide resin 13. The sulphonamide 14 was finally cleaved from the solid support in mild acidic conditions.

Scheme 4 Synthetic route to obtaining sulfamates 11 (amine) and 14 (sulfonamide).

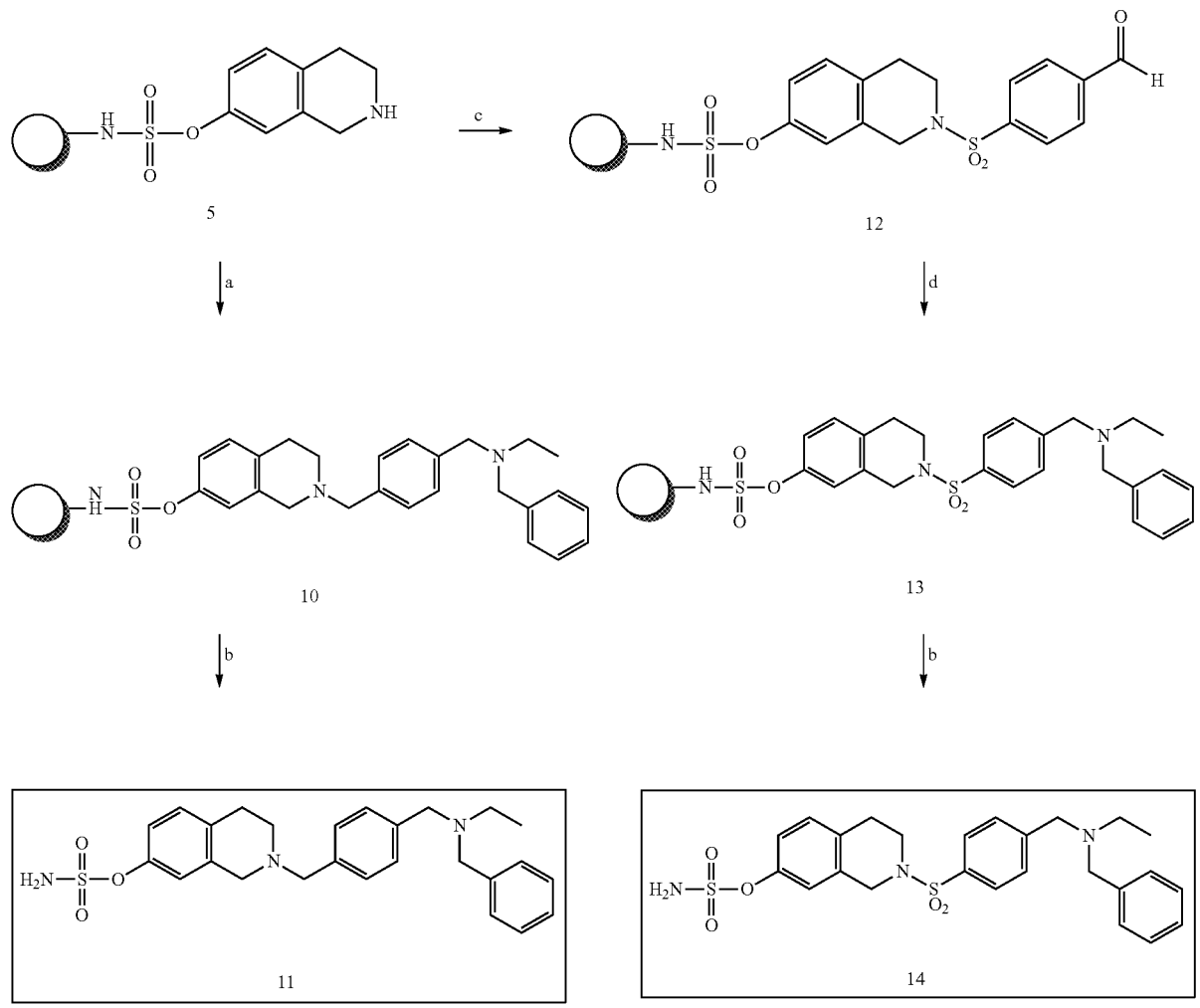

Reagents and conditions: (a) i) 4-{[benzyl(ethyl)amino]methyl}benzaldehyde, AcOH, NMP rt, 45 min; ii) NaBH(OAc)$_3$, NMP, 18 h, rt; (b) 30% HFIP in DCM, rt; (c) 4-sulfonylchloride-benzaldehyde, triethylamine, DCM, rt; (d) i) N-benzylethanamine, AcOH, NMP, rt, 45 min; ii) NaBH(OAc)$_3$, NMP, rt, 18 h.

STS inhibition studies for the compound obtained from Schemes 3 and 4 were conducted as outlined below.

The enzymatic assay was performed using homogenate of STS transfected HEK-293 cells as the source of enzyme activity. The transformation of [$^3$H]-E1S into [$^3$H]-E1 was measured using scintillation counting of labeled E1S and E1 in the aqueous and organic phases, respectively. Newly synthesized sulfamate compounds were tested at two concentrations (0.1 μM and 1 μM). Libraries 1-EO and 2-EO were synthesized using the p- and m-benzamide spacers as 1$^{st}$ level of molecular diversity and the same wide variety of secondary amines as 2$^{nd}$ level of diversity (Table 2), which were chosen in a somewhat random fashion while including a different pattern, format and heteroatom. As can be seen, library 1 (para) presents more inhibitory potency toward the enzyme compared to library 2 (meta). Compounds 1-EO-07, 1-EO-09 and 1-EO-10 represent a starting point for optimization, as they show more than 36% of inhibition when tested at a concentration of 0.1 μM. These compounds have relatively hydrophobic substituents compared to the rest of the library members. In fact, log P values for 1-EO-07, 1-EO-09 and 1-EO-10 are 3.87, 3.08 and 3.07, respectively. The average log P value for the rest of the library, excluding these three compounds, is 1.93.

Library 2 members with the tertiary amine side-chain in meta position showed overall less potency of inhibition compared to library 1 members in para position. As an example, compound 2-EO-09 gave 17% of STS inhibition at 0.1 μM while the para equivalent (1-EO-09) displayed 67% of inhibition at the same concentration. However, we decided to keep both orientations for the next libraries in order to see if optimized secondary amines in meta position would yield better results. It is important to keep in mind that the objective is not only to develop an STS inhibitor (sulfamate derivatives), but also to obtain a compound that can act as a SERM in its phenolic form. The usual interaction between an SERM, generally a phenol derivative, and the ER depends on the hydrogen bond.[35]

Results obtained from the STS studies of the compounds obtained from Schemes 3 and 4 are outlined in Tables 2 and 3 below.

TABLE 2

Structure of the sulfamate compounds of libraries 1-EO and 2-EO and their inhibitory activity (%) for the transformation of [$^3$H]-estrone sulfate into [$^3$H]-estrone by STS (HEK-293 transfected cells).

| R | Para compound | | | Meta compound | | |
|---|---|---|---|---|---|---|
| | | STS inhibition (%)[a] | | | STS inhibition (%)[a] | |
| | ID | 0.1 μM | 1 μM | ID | 0.1 μM | 1 μM |
| ----N(morpholine)O | 1-EO-01 | 10.9 ± 3.5 | 50.6 ± 1.2 | 2-EO-01 | 0.0 ± 4.7 | 20.9 ± 4.4 |
| ----N(piperidine) | 1-EO-02 | 11.5 ± 2.4 | 38.3 ± 3.6 | 2-EO-02 | 1.0 ± 5.1 | 11.9 ± 2.6 |
| ----N(thiomorpholine)S | 1-EO-03 | 32.3 ± 1.0 | 80.2 ± 0.9 | 2-EO-03 | 2.3 ± 0.1 | 39.6 ± 2.8 |
| ----N(piperazine)N— | 1-EO-04 | 2.9 ± 0.5 | 23.3 ± 1.3 | 2-EO-04 | 0.0 ± 12.2 | 12.6 ± 2.3 |
| ----N(piperazine)N-benzyl | 1-EO-05 | 20.8 ± 3.7 | 75.8 ± 1.6 | 2-EO-05 | 0.0 ± 3.1 | 23.7 ± 0.6 |
| ----N(piperazine)N-pyrimidine | 1-EO-06 | 14.7 ± 3.6 | 41.9 ± 0.8 | 2-EO-06 | 1.6 ± 1.6 | 24.4 ± 0.4 |
| ----N(piperidine)-CH2-phenyl | 1-EO-07 | 41.4 ± 0.8 | 81.3 ± 0.5 | 2-EO-07 | 1.4 ± 0.6 | 41.9 ± 2.7 |
| ----N(piperidine)-N(piperidine) | 1-EO-08 | 8.5 ± 1.2 | 53.7 ± 4.7 | 2-EO-08 | 0.0 ± 2.4 | 8.0 ± 1.1 |
| ----N(ethyl)(benzyl) | 1-EO-09 | 66.9 ± 1.5 | 83.6 ± 0.2 | 2-EO-09 | 17.3 ± 2.5 | 69.0 ± 0.0 |
| ----N(dipropyl) | 1-EO-10 | 36.6 ± 1.3 | 84.7 ± 0.2 | 2-EO-10 | 8.3 ± 0.0 | 54.8 ± 1.2 |

[a] Compounds were tested at two concentrations, 0.1 μM and 1 μM. Results are expressed as mean ± SEM of one experiment performed in triplicate.

TABLE 3

Structure of the sulfamate compounds of libraries 3-EO and 4-EO and their inhibition (%) of the transformation of [$^3$H]-estrone sulfate into [$^3$H]-estrone by STS (HEK-293 transfected cells).

| R | Para compound | | | Meta compound | | |
|---|---|---|---|---|---|---|
| | | STS inhibition (%) [a] | | | STS inhibition (%) [a] | |
| | ID | 0.1 μM | 1 μM | ID | 0.1 μM | 1 μM |
| N-CH2-Ph (propyl linker) | 3-EO-01 | 64.8 ± 3.8 | 94.3 ± 0.3 | 4-EO-01 | 23.1 ± 7.5 | 67.4 ± 10.9 |
| N-CH2-Ph, CH2CH2OH | 3-EO-02 | 27.9 ± 2.6 | 78.0 ± 1.1 | 4-EO-02 | 26.7 ± 7.2 | 32.4 ± 6.3 |
| N-CH2-Ph, CH2CH2CH2OH | 3-EO-03 | 5.7 ± 4.4 | 64.3 ± 1.6 | 4-EO-03 | 25.8 ± 3.9 | 37.3 ± 7.0 |
| N-CH2-Ph, CH2CH2NMe2 | 3-EO-04 | 13.9 ± 4.8 | 57.8 ± 3.4 | 4-EO-04 | 0.0 ± 0.0 | 28.6 ± 2.2 |
| N-CH2-Ph, CH2CH2CH2NMe2 | 3-EO-05 | 16.2 ± 4.6 | 61.6 ± 4.9 | 4-EO-05 | 23.8 ± 4.1 | 26.0 ± 8.5 |
| N-Me, CH2CH2-piperidine | 3-EO-06 | 0.3 ± 1.7 | 26.8 ± 13.5 | 4-EO-06 | 24.5 ± 7.4 | 30.8 ± 6.4 |
| N-Me, CH2CH2CH2-piperidine | 3-EO-07 | 17.4 ± 12.3 | 40.7 ± 8.6 | 4-EO-07 | 24.1 ± 0.4 | 30.6 ± 6.9 |
| N-(CH2CH2-NMe)2 | 3-EO-08 | 3.8 ± 9.6 | 15.9 ± 21.5 | 4-EO-08 | 0.0 ± 0.0 | 17.1 ± 7.6 |

TABLE 3-continued

Structure of the sulfamate compounds of libraries 3-EO and 4-EO and their inhibition (%) of the transformation of [$^3$H]-estrone sulfate into [$^3$H]-estrone by STS (HEK-293 transfected cells).

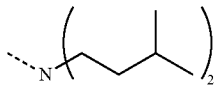

| R | Para compound ID | STS inhibition (%) [a] 0.1 μM | 1 μM | Meta compound ID | STS inhibition (%) [a] 0.1 μM | 1 μM |
|---|---|---|---|---|---|---|
| 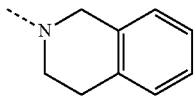 | 3-EO-09 | 47.0 ± 13.0 | 90.8 ± 1.7 | 4-EO-09 | 32.3 ± 2.9 | 75.9 ± 4.2 |
| 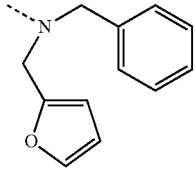 | 3-EO-10 | 56.0 ± 7.2 | 83.0 ± 11.9 | 4-EO-10 | 24.1 ± 5.6 | 50.2 ± 1.9 |
| 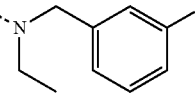 | 3-EO-11 | 90.8 ± 2.6 | 98.2 ± 0.4 | 4-EO-11 | 27.5 ± 0.9 | 90.5 ± 1.4 |
| 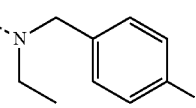 | 3-EO-12 | 80.2 ± 8.0 | 97.2 ± 0.6 | 4-EO-12 | 20.9 ± 7.1 | 24.9 ± 0.6 |
| 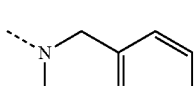 | 3-EO-13 | 78.2 ± 1.7 | 95.9 ± 0.6 | 4-EO-13 | 24.2 ± 4.9 | 84.5 ± 3.7 |
| 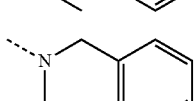 | 3-EO-14 | 42.5 ± 3.5 | 87.7 ± 0.7 | 4-EO-14 | 6.5 ± 6.9 | 19.9 ± 12.6 |
| 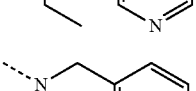 | 3-EO-15 | 35.7 ± 4.3 | 85.2 ± 1.7 | 4-EO-15 | 14.3 ± 4.7 | 33.5 ± 5.8 |
| 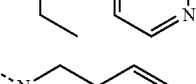 | 3-EO-16 | 47.0 ± 1.8 | 86.6 ± 1.8 | 4-EO-16 | 33.3 ± 0.0 | 52.8 ± 1.3 |
| (4-F-benzyl ethylamine) | 3-EO-17 | 69.1 ± 1.9 | 91.2 ± 2.7 | 4-EO-17 | 10.9 ± 7.4 | 66.5 ± 4.5 |

[a] Compounds were tested at two concentrations, 0.1 μM and 1 μM. Results are expressed as mean ± SEM of one experiment performed in triplicate.

Before the synthesis of subsequent libraries, we were concerned about the influence of the chemical functionality acting at the junction point between the tetrahydroisoquinoline moiety and the benzylamine portion on STS inhibition. We thus synthesized the amine and sulfonamide analogs (sulfamate derivatives 11 and 14) of 1-EO-9 of library 1. The inhibition levels of amine analog 11 (1% at 0.1 μM and 17% at 1 μM) and sulfonamide analog 14 (10% at 0.1 μM and 31% at 1 μM) were lower than the inhibition of the amide derivative 1-EO-9 (67% at 0.1 μM and 84% at 1 μM) (FIG. 11). We thus conserved the amide functionality at the junction point for elaboration of subsequent libraries 3-EO and 4-EO.

Based on the results obtained for compounds of libraries 1 and 2, we selected new amines to yield libraries 3-EO and 4-EO (Table 3). It can be seen that the inhibitory potency was increased for both orientations, but the para position (library 3) still gave better results. As expected, the most hydrophobic substituents produced higher inhibitory effects. For instance, compound 3-EO-11 bearing a N-furyl-N-benzyl side chain gave 91% of STS inhibition at 0.1 µM. Hydrophobic compounds 3-EO-12 and 3-EO-13 bearing a N-ethyl-N-bromobenzyl side chain gave interesting results with 80% and 78% of inhibition at 0.1 µM. Also, it is important to note that an inhibitory effect has also been achieved with more polar side chains. Interestingly, compounds 3-EO-14, 3-EO-15 and 3-EO-16 showed inhibition of 36-47% at 0.1 µM and 85-88% at 1 µM. These three sulfamate derivatives possess a N-pyridine-N-ethyl side chain, with a difference in the position of the nitrogen in the pyridine ring. These results show that side chains with a heteroatom capable of forming hydrogen bonds are promising in obtaining an SERM effect. Some inhibitors of library 4 had an inhibitory effect only at higher concentrations. For example, three compounds (4-EO-09, 4-EO-11 and 4-EO-13) gave more than 75% of inhibition at 1 µM.
Proliferative (Estrogenic) Activity (MCF-7 (ER+) Cells)

The next step was to determine the presence or absence of estrogenic activity. To do so, cell proliferative assays were carried out on MCF-7 cells. This breast cancer cell line is known to express the estrogen receptor (ER).[74] This means that molecules possessing estrogenic activity, such as the potent estrogen estradiol (E2) used as a reference compound, will activate the ER, thus inducing cell growth over the control fixed at 100%. Phenols of the corresponding sulfamate library 3-EO and 4-EO are referred to as library 3'-EO and library 4'-EO, respectively. Proliferative activities of all members of these two libraries of phenol derivatives have been tested to investigate their estrogenic activity at three concentrations of 0.01 µM, 0.1 µM and 1 µM (FIG. 12).

As can be seen on FIG. 12A, library 3'-EO, with the side chain in para position, has only a few phenol derivatives that display an estrogenic activity. Thus, only phenol derivatives 3'-EO-02, 3'-EO-05, 3'-EO-12 and 3'-EO-13 induce the proliferation of ER+ cell line MCF-7 at a concentration of 1 µM (135, 126, 118 and 177%, respectively). As a point of comparison, the potent estrogen E2 induced a proliferation of 176% at the lower concentration of 0.1 nM. Although these proliferative effects are low in comparison to the effect of a potent estrogen, it is desirable to obtain compounds without estrogenic potency. The phenol derivative 3'-EO-11, corresponding to the sulfamate derivative 3-EO-11, did not stimulate the ER-cell growth at the concentrations tested. In contrast to library 3'-EO, library 4'-EO, with the side chain in meta position, seemed to contain more estrogenic compounds (FIG. 12B). Most of the compounds stimulated the growth of the estrogen-dependent MCF-7 cells at 1 µM. Thus, not only were the sulfamate derivatives from library 4-EO less potent than those from library 3-EO, but most of the phenol derivatives from library 4'-EO were estrogenic. With the results of estrogenic assays for phenol derivatives and considering the results of STS inhibition for the sulfamate derivatives, it can be seen that phenol derivatives 3-EO-9 to 11 and 3-EO-14 to 17 would be interesting for further investigation concerning the SERM effect.
Proliferative and Alkaline Phosphatase (ALP) Activities (Saos-2 (ER+) Cells)

Estrogens are known to have a beneficial effect on bones. Indeed, osteoblast cells express the ER and modulate the formation of bone tissue.[75] Osteoblast cells are thus a good in vitro model for the evaluation of SERM compounds because their proliferation is partly mediated by estrogenic molecules such as E2. The phenol derivatives 3'-EO-09 to 3'-EO-11 and 3'-EO-14 to 3'-EO-17 were tested on the osteoblast-like cell line Saos-2 to further evaluate their SERM capacity (FIG. 13A). The reference compounds raloxifen (SERM) and E2 (estrogen), at a concentration of 1 µM, stimulated the proliferation of Saos-2 by 123% and 144%, respectively. All of the phenolic compounds tested were also able to significantly stimulate Saos-2 cell proliferation, but the proliferative effects are more important for 3'-EO-14 to 3'-EO-17 than for 3'-EO-09 to 3'-EO-11. Compound 3'-EO-14 produced a good stimulation of Saos-2 cell proliferation (140%). This compound surpasses the stimulation induced by raloxifen and reaches a similar level of cell proliferation as E2.

We also investigated the effect of selected phenol derivatives on alkaline phosphatase activity in Saos-2 cells (FIG. 13B). ALP activity is a more sensitive test than cell proliferation and allows us to determine if a compound can activate osteoblast maturation and mineralization. As reference compounds, tested at a concentration of 1 nM, E2 and the SERM tamoxifen increased ALP activity to 148% and 143%, respectively, when compared to control (no treatment) fixed at 100%. At the same concentration, the phenol derivatives increased the ALP activity 133 to 152%, and higher effects were obtained with 3'-EO-14 (147%) and 3'-EO-17 (152%).

Experimental for the Compounds of Schemes 3 and 4 Above
Chemistry

N-Fmoc protection of 1,2,3,4-tetrahydroisoquinolin-7-ol (synthesis of 2): To a stirred solution of 1,2,3,4-tetrahydroisoquinolin-7-ol hydrobromide (5.0 g) in 500 mL of THF/$H_2O$ (1:1) and 65 mL of a solution of $NaHCO_3$ (1 N) was added Fmoc-O-succinimide (7.69 g). The solution was vigorously stirred for 2 h at room temperature under argon atmosphere. Water was then added and the mixture was extracted with EtOAc. The organic phase was washed with water and with brine, and dried over $Na_2SO_4$ and evaporated to dryness. Purification by flash chromatography with hexanes/EtOAc (1:1) yielded 7.36 g (91%) of phenol derivative 2.

(9H-Fluoren-9-yl)methyl-7-hydroxy-3,4-dihydroisoquinoline-2(1H)-carboxylate (2): White solid; IR (film) υ: 3321 (OH), 1674 (C=O, carbamate); $^1H$ NMR (acetone-$d_6$) δ: 2.68 (m, 2H), 3.61 (t, J=6.0 Hz, 2H), 4.32 (t, J=6.6 Hz, 1H), 4.45 (d, J=6.6 Hz, 2H), 4.49 (s, 2H), 6.62 (s, 1H), 6.68 (d, J=6.4 Hz, 1H), 6.98 (d, J=8.2 Hz, 1H), 7.33 (br s, 2H), 7.40 (m, 2H), 7.68 (br s, 2H), 7.86 (br s, 2H), 8.23 (br s, 1H); $^{13}C$ NMR (acetone-$d_6$) δ: 42.6, 46.4, 48.1, 67.7, 113.2, 114.7, 120.7, 125.9, 126.0, 127.9, 128.4, 130.4, 142.1, 145.1, 155.7, 156.5. APCI-MS (+): 372 m/z $[M+H]^+$.

Sulfamoylation of N-Fmoc protected 1,2,3,4-tetrahydroisoquinolin-7-ol (synthesis of 3): The stirred solution of N-Fmoc protected 1,2,3,4-tetrahydroisoquinolin-7-ol (5.0 g) (2) in 100 mL of dry dimethylacetamide (DMA) under argon was cooled to 0° C., followed by addition of sulfamoyl chloride (4.6 g).[76] After 1 h of stirring at room temperature, the reaction was cooled back to 0° C. followed by another addition of sulfamoyl chloride (4.6 g). The mixture was then allowed to react for 3 h at room temperature. The reaction was quenched with water, and the crude product was extracted with EtOAc. The organic phase was washed with brine, dried over $Na_2SO_4$, and evaporated to dryness. Purification by trituration with diethyl ether yielded 5.16 g (85%) of sulfamate 3.

(9H-Fluoren-9-yl)methyl-7-(sulfamoyloxy)-3,4-dihydroisoquinoline-2(1H)-carboxylate (3): White solid; IR (film) υ: 3213 (NH$_2$), 1682 (C=O, carbamate), 1381 and 1180 (S=O, sulfamate); $^1$H NMR (CDCl$_3$) δ: 2.78 (br s, 2H), 3.65 (br s, 2H), 4.26 (t, J=6.4 Hz, 1H), 4.49 (m, 3H), 4.61 (s, 1H), 5.47 (br s, 2H), 7.07 (d, J=19.7 Hz, 1H), 7.14 (s, 2H), 7.31 (d, J=6.7 Hz, 2H), 7.39 (d, J=6.1 Hz, 2H), 7.57 (br s, 2H), 7.75 (d, J=12.9 Hz); $^{13}$C NMR (acetone-d$_6$) δ: 42.7, 46.2, 48.2, 67.9, 120.7, 120.8, 121.3, 125.9, 128.0, 128.5, 130.8, 142.2, 145.1, 155.7; APCI-MS (+): 451 m/z [M+H]$^+$.

Coupling of NFmoc protected 7-sulfamate-1,2,3,4-tetrahydro-isoquinoline with trityl resin (synthesis of 4): Trityl chloride resin (1.75 mmol/g theoretical loading) (10 g) was swollen under argon in 50 mL of dry CH$_2$Cl$_2$. After 5 min of stirring, sulfamate 3 (9.49 g) was added as a solution in 50 mL of dry DMA/CH$_2$Cl$_2$ (1:1) followed by the addition of DIPEA (18.3 mL), and the mixture was shaken for 24 h at room temperature. The resin was filtered and washed successively with CH$_2$Cl$_2$ (3×), MeOH (3×), CH$_2$Cl$_2$ (3×) and MeOH (3×), then dried overnight under vacuum to afford 14.05 g of resin 4. The coupling (loading) yield calculated by the means of the mass increase was 56%. The filtrate was collected and evaporated to dryness to isolate 3.74 g of unreacted sulfamate 3. The loading yield calculated by the recovered amount of compound 3 was 60%.

Procedure for the NFmoc deprotection of resins 4 (synthesis of 5): The N-Fmoc protected resins 4 (13.85 g) were reacted for 2 h with 260 mL of a solution of piperidine in DMF (20%) for the cleavage of the Fmoc protecting group. The resins were filtered and washed with CH$_2$Cl$_2$ (3×), with MeOH (3×), and again with CH$_2$Cl$_2$ (3×), then dried overnight under vacuum to give 11.00 g of resin 5.

Acylation of the resins 5 with carboxybenzaldehyde (synthesis of 6): Resins 5 (2.4 g) were swollen under argon in 25 mL of dry DMF. After 5 min of shaking, the resins were filtered and 3-carboxybenzaldehyde (or 4-carboxybenzaldehyde) (2.16 g), N-hydroxybenzotriazol (HOBt) (1.95 g) and benzotriazol-1-yl-oxytripyrrolidinophosphonium hexafluorophosphate (PyBOP) (7.95 g) were added as a solution in 25 mL of dry DMF followed by addition of a solution of DIPEA (5.02 mL) in 24 mL of dry DMF. The resins were shaken for 3 h at room temperature, then filtered and washed with DMF (3×) and with CH$_2$Cl$_2$ (4×). The resins were dried overnight under vacuum to give 2.61 g of resin 6. The coupling (loading) yield calculated by the means of the mass increase was 81%.

Reductive amination of the resins 6 with secondary amines (synthesis of 7): Resins 6 were weighted, and then divided in 10 or 17 wells to perform reductive amination (70 mg of resin 6/well for libraries 1 and 2) (125 mg of resin 6/well for libraries 3 and 4). Each well was swollen under argon in 2 mL of N-methyl-2-pyrrolidone (NMP). After 2 min of stirring, the resins were filtered and secondary amine (0.5 mmol) was added as a solution in 1 mL of NMP followed by the addition of 1 mL of a solution of acetic acid in NMP (30%). The resins were then stirred for 10 min followed by the addition of NaBH(OAc)$_3$ (0.7 mmol) as a solution in 1 mL of NMP. The resins were stirred for 18 h at room temperature, then filtered and washed successively with DMF, H$_2$O, EtOH, DMF, H$_2$O, EtOH and CH$_2$Cl$_2$. The resins were dried overnight under vacuum to afford resin 7.

Acid cleavage of the resins 7 (synthesis of 8; Libraries 1-4): Resins 7 were allowed to react for 1 h with 3 mL of a solution of 1,1,1,3,3,3-hexafluoro-2-propanol (HFIP) in CH$_2$Cl$_2$ (30%), then filtered and washed with CH$_2$Cl$_2$. The organic layer was collected in pre-weighed tubes and the solvent was evaporated under reduced pressure. Residual solvents were removed by co-evaporation with toluene and CH$_2$Cl$_2$, and then dried under vacuum pump to generate sulfamate compounds 8. Range and average quantities obtained for each library: 1-EO=6.0-25.0 mg, average=13.8 mg; 2-EO=11.0-26.0 mg, average=17.7 mg; 3-EO=18.0-33.6 mg, average=27.1 mg; 4-EO=18.6-40.9, average=32.4 mg. All library members were obtained as one major compound (by TLC analysis) having the right mass (by LRMS analyses). Three compounds from both libraries 1-EO and 2-EO and four compounds from both libraries 3-EO and 4-EO were randomly chosen for IR, $^1$H NMR and LRMS characterizations.

Nucleophilic cleavage of the resins 7 (synthesis of 9): Resins 7 were allowed to react for 24 h at 60° C. with 3 mL of a solution of DEA in THF (30%), then filtered and washed with DMF. The organic layer was collected in pre-weighed tubes and the solvent was evaporated under reduced pressure. Residual solvents were removed by co-evaporation with toluene and CH$_2$Cl$_2$, and then dried under vacuum pump to generate phenol derivatives 9. Range and average quantities obtained for each library: 3'-EO=15.6-32.6 mg, average=28.1 mg; 4'-EO=28.2-35.9, average=31.9 mg. All library members were obtained as one major compound (by TLC analyses) that possesses the right mass (by LRMS analyses). Four compounds from each library (3'-EO and 4'-EO) were randomly chosen for IR, $^1$H NMR and LRMS characterizations.

Reductive amination of resin 5 with 4-{[benzyl(ethyl)amino]methyl}benzaldehyde and cleavage from the resin (synthesis of 11): The resin 5 (70 mg, 0.06 mmol) was first swollen in 2 mL of NMP and stirred for 2 min. The resin was filtered and 4-{[benzyl(ethyl)amino]methyl}benzaldehyde (43 mg, 0.17 mmol) was added as a solution in 0.5 mL of NMP followed by the addition of 0.5 mL of a solution of acetic acid in NMP (30%). The resin was then stirred for 45 min under argon atmosphere followed by the addition of NaBH(OAc)$_3$ (0.7 M) in 0.5 mL of NMP. The resins were stirred for 18 h at room temperature under argon atmosphere, then filtered and washed successively with DMF, H$_2$O, EtOH, DMF, H$_2$O, EtOH and CH$_2$Cl$_2$. The resin was dried overnight under vacuum to afford resin 10. This resin was allowed to react for 1 h with 3 mL of a solution of 1,1,1,3,3,3-hexafluoro-2-propanol (HFIP) in CH$_2$Cl$_2$ (30%), then filtered and washed with CH$_2$Cl$_2$. The organic layer was evaporated under reduced pressure. Residual solvents were removed by co-evaporation with toluene and CH$_2$Cl$_2$, and then dried under vacuum. The crude compound was purified by flash chromatography using DCM/MeOH (9:1) to give compound 11 as yellow amorphous solid; IR (KBr) υ: 3394 (NH$_2$), 1373 and 1180 (S=O, sulfamate); $^1$H NMR (400 MHz, methanol-d$_4$) δ: 1.11 (t, J=7.1 Hz, 3H), 2.53 (q, J=7.1 Hz, 2H), 2.79 (t, J=6.1 Hz, 2H), 2.91 (t, J=5.9 Hz, 2H), 3.60 (s, 4H), 3.66 (s, 2H), 3.71 (s, 2H), 6.99 (d, J=2.2 Hz, 1H), 7.09 (dd, J$_1$=8.4 Hz, J$_2$=2.4 Hz, 1H), 7.17 (d, J=8.4 Hz, 1H), 7.24 (t, J=7.2 Hz, 1H), 7.31 (t, J=7.2 Hz, 2H), 7.37 (s, 5H); APCI-MS (+): 466.4 m/z [M+H]$^+$.

Sulfonylation of resin 5 (synthesis of 12): Resin 5 (100 mg, 0.08 mmol) was first swollen in 2 mL of DCM and stirred for 2 min. The resin was filtered and 2 mL of a solution of 4-sulfonylchloride benzaldehyde in DCM (0.3 M) was added. The suspension was stirred for 12 h under argon atmosphere at room temperature. The resin was then filtered and washed thoroughly with DCM and dried under vacuum.

Reductive amination of resin 12 with 4-ethylaminobenzyl and cleavage from the resin (synthesis of 14): The resin 12 (70 mg, 0.06 mmol) was first swollen in 2 mL of NMP and stirred for 2 min. The resin was filtered and N-benzylethanamine (23 mg, 0.17 mmol) was added as a solution in 0.5 mL of NMP followed by the addition of 0.5 mL of solution of acetic acid in NMP (30%). The resin was then stirred for 45 min under argon atmosphere followed by the addition of a solution of $NaBH(OAc)_3$ (0.7 M) in 0.5 mL of NMP. The resin was stirred for 18 h at room temperature under argon atmosphere, then filtered and washed successively with DMF, $H_2O$, EtOH, DMF, $H_2O$, EtOH and $CH_2Cl_2$. The resin was dried overnight under vacuum to afford resin 13. This resin was allowed to react for 1 h with 3 mL of a solution of 1,1,1,3,3,3-hexafluoro-2-propanol (HFIP) in $CH_2Cl_2$ (30%), then filtered and washed with $CH_2Cl_2$. The organic layer was evaporated under reduced pressure. Residual solvents were removed by co-evaporation with toluene and $CH_2Cl_2$, and then dried under vacuum. The crude compound was purified by flash chromatography using EtOAc/Hexanes (7:3) to give compound 14 as light yellow solid; IR (KBr) υ: 3356 and 3271 ($NH_2$), 1381 and 1180 (S=O, sulfamate and sulfonamide); $^1$H NMR (400 MHz, acetone-$d_6$) δ: 1.07 (t, J=7.1 Hz, 3H), 2.50 (q, J=7.1 Hz, 2H), 2.92 (t, J=5.8 Hz, 2H), 3.35 (t, J=6.0 Hz, 2H), 3.59 (s, 2H), 3.67 (s, 2H), 4.24 (s, 2H), 7.07-7.22 (m, 4H), 7.30 (d, J=7.7 Hz, 2H), 7.38 (d, J=7.5 Hz, 2H), 7.65 (d, J=8.2 Hz, 2H), 7.81 (d, J=8.4 Hz, 2H); APCI-MS (+): 516.3 m/z $[M+H]^+$.

Biological Assays for the Compounds of Schemes 3 and 4 Above

Inhibition of STS Activity:

This enzymatic assay was carried out according to a procedure previously described for the transformation of substrate [$^3$H]-E1S (100 μM) into [$^3$H]-E1 by homogenated HEK-293 cells over-expressing the enzyme activity.[56,73]

Proliferative (Estrogenic) Activity on MCF-7 ($ER^+$) Cells:

This cell assay was carried out according to a procedure previously described to determine the estrogenic activity of enzyme inhibitors on the growth of estrogen-sensitive MCF-7 cells.[77] All chemicals tested were first dissolved in DMSO and subsequent dilutions were done in the proper cell culture media. The final concentration of DMSO in the culture medium was 0.1% or less. 3-(4,5-dimethylthiazol-2-yl)-5-(3-carboxymethoxyphenyl)-2-(4-sulfophenyl)-2-H-tetrazolium (MTS) was used as an indirect colorimetric measurement of cell proliferation according to the manufacturer's instructions (Promega, Madison, Wis.). At the end of the treatments, 20 μL of MTS solution was added to each well (100 μL) and the MCF-7 cells were incubated 4 h at 37° C. The absorbance at 490 nm was then measured with a Thermo max microplate reader (Molecular Devices, Sunnyvale, Calif.). The control (culture media+DMSO) is set to 100% of cell proliferation.

Proliferative Activity on Saos-2 ($ER^+$) Cells:

The osteoblast-like Saos-2 cells were maintained in culture flasks (175 $cm^2$ growth area, BD Falcon) at 37° C. in a 5% $CO_2$ humidified atmosphere and grown in McCoy's 5A medium supplemented with 10% fetal bovine serum (FBS), penicillin (100 IU/mL) and streptomycin (100 μg/mL). Penicillin/streptomycin mix, L-Glutamine, normal and charcoal-stripped FBS were purchased from Wisent, Inc. (St-Bruno, QC, Canada), phenol-red free McCoy's 5A was purchased from PromoCell (Heidelberg, Germany). Chemicals tested were first dissolved in DMSO and subsequent dilutions were done in the cell culture medium. The final concentration of DMSO in the culture medium was 0.1% or less. For the proliferation assay, the 5% FBS in the culture medium was replaced with 10% charcoal-stripped FBS. The cells were seeded in 96-well plates at a density of 10 000 cells/well and allowed to attach 24 h. After 24 h, the phenolic compounds diluted in culture medium were added to the wells and replaced every 2 days for 7 days of treatment. As reported above, MTS was used as an indirect colorimetric measurement of cell proliferation according to the manufacturer's instructions, except the plate were incubated 2 h instead of 4 h. Results were reported as cell proliferation in % (mean±SD of one experiment) where the control of cell proliferation was fixed at 0%.

Alkaline Phosphatase Assay (Saos-2 Cells):

Saos-2 cells were used similarly as reported in the cell proliferation assay. The cells were seeded at a density of 2 000 cells/well and treated for 3 days with each compound to be tested. The alkaline phosphatase (ALP) activity was measured using the Sensolyte® pNPP Alkaline Phosphatase Assay Kit *Colorimetric* (AnaSpec, Freemont, Calif.) following the manufacturer's protocol. Briefly, after three days of treatment, the cells were washed twice with washing buffer (provided with the kit) and lysed with 0.2% Triton X-100. The cell lysates were centrifuged and the supernatants were used to determine ALP activity. The supernatants were deposed in a 96-well plate and incubated for 30 minutes with a p-nitrophenyl phosphate solution (provided with the kit). The absorbance at 405 nm was measured with a Thermo max microplate reader (Molecular Devices, Sunnyvale, Calif.). The control (culture media+DMSO) is set to 100% of alkaline phosphatase activity.

Table 4 below outlines further results in relation to compounds according to the invention presenting a dual action—STS inhibition and SERM effect (ISTS-SERM).

TABLE 4

STS inhibition and SERM activity on compound ISTS-SERM (EO-33)

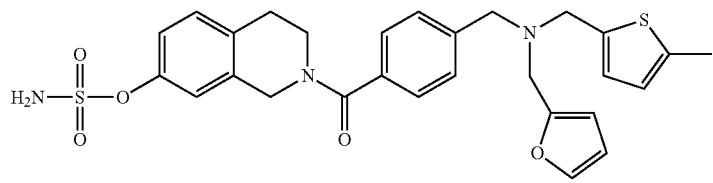

EO-33 (sulfamate compound)

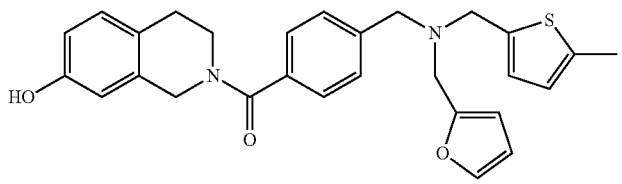

EO-29 (phenol compound)

| Compound | Steroid Sulfatase Inhibition[c] IC$_{50}$ (nM) | Breast cancer cells T-47D (ER$^+$)[a] | | SERM effect Proliferative activity (%) | | Bone cells Saos-2 (ER$^+$)[b] SERM effect Alkaline phosphatase activity (%)[d] |
|---|---|---|---|---|---|---|
| | | Antagonist activity (%) 1 μM | Agonist activity (%) 1 μM | 0.1 μM | 1 μM | 0.1 nM |
| EO-33 (sulfamate) | 3.9 | 25 | 0 | 33 | 211 | 48 |
| EO-29 (phenol) | >>1000 | 46 | 0 | 175 | 250 | 114 |
| Raloxifene | >>1000 | 96 | 0 | 75 | 83 | 86 |
| Estradiol | >>1000 | 0 | 100 | 100 | 100 | 100 |

STS: steroid sulfatase;
SERM: selective estrogen receptor modulator;
[a]antagonist (antiestrogenic) activity and agonist (estrogenic) activity of compounds EO-33 and EO-29 (1 μM) on estrogen sensitive T-47D cells in % of control (100%; 0.1 nM of estradiol);
[b]level of cellular proliferation of Saos-2 cells in percentage of control (100%; 0.1 nM of estradiol);
[c]IC$_{50}$ (nM) of the transformation of E1S into E1 in homogenate of HEK-293 transfected cells with STS;
[d]alkaline phosphatase activity.

Figure 14:
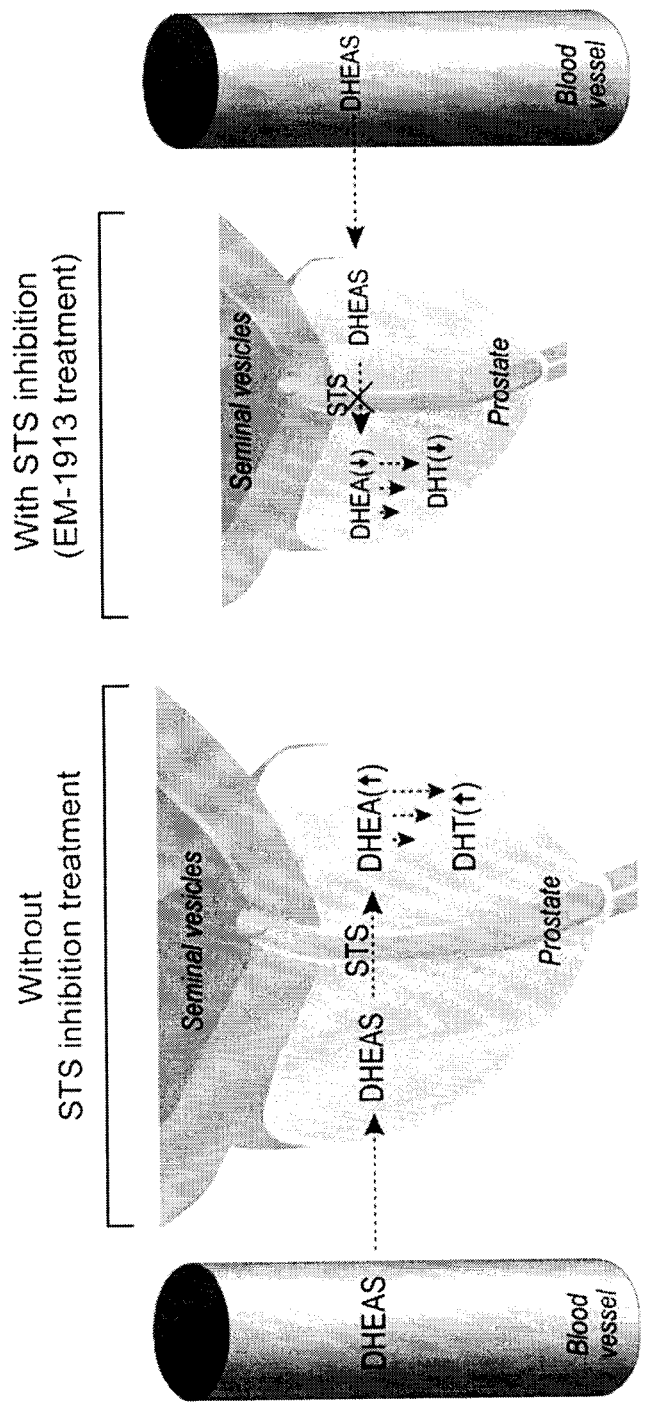
FIG. 14 illustrates the effect of EM-1913 (an inhibitor of STS without SERM effect) on the size of prostate and seminal vesicles stimulated with DHEAS (right part) compared to the effect of DHEAS alone (left part).

Previous studies conducted in our group have led to the disclosure of the effectiveness of STS inhibition in an in vivo model for androgen-sensitive tissues (EM-1913).[55,78] These teachings will be considered for further studies. More specifically, when tested in vivo, EM-1913 did not possess harmful estrogenic activity, since it did not stimulate the uterus weight of ovariectomized mice (OVX). In addition, it effectively blocked the stimulation of uterine weight induced by E1S in OVX mice. EM-1913 was also found to block the effect of DHEAS on the weight of AR$^+$ tissues (prostate and seminal vesicles). No more harmful androgenic effect was detected when EM-1913 was injected in the absence of DHEAS. These results outlined in FIG. 14 also show the ability of a STS inhibitor to block the androgenic effect of DHEAS (via hydrolysis of the sulfate group of DHEAS and its subsequent transformation into testosterone and dihydrotestosterone by 17β-HSDs and 5α-reductase).

Although the present invention has been described hereinabove by way of specific embodiments thereof, it can be modified, without departing from the spirit and nature of the subject invention as defined in the appended claims.

The present description refers to a number of documents, the content of which is herein incorporated by reference in their entirety.

REFERENCES

1. Jonat W., Pritchard K. I., Sainsbury R., Klijn J. G. Trends in endocrine therapy and chemotherapy for early breast cancer: a focus on the premenopausal patient. J. Cancer Res. Clin. Oncol. 2006, 132, 275-286.
2. Lin S. X., Chen J., Mazumdar M., Poirier D., Wang C., Azzi A., Zhou M. Molecular therapy of breast cancer: progress and future directions. Nat. Rev. Endocrinol. 2010, 6, 485-493.
3. McDonnell D. P., Wardell S. E. The molecular mechanisms underlying the pharmacological actions of ER modulators: implications for new drug discovery in breast cancer. Curr. Opin. Pharmacol. 2010, 10, 620-628.
4. Duggan C., Marriott K., Edwards R., Cuzick J. Inherited and acquired risk factors for venous thromboembolic disease among women taking tamoxifen to prevent breast cancer. J. Clin. Oncol. 2003, 21, 3588-3593.
5. Agnusdei D., Iori N. Raloxifene: results from the MORE study. J. Musculoskelet. Neuronal Interact. 2000, 1, 127-132.
6. Obiorah I., Jordan, V. C. Progress in endocrine approaches to the treatment and prevention of breast cancer. Maturitas. 2011, 70, 315-321.

7. Suzuki T., Moriya T., Ishida T., Ohuchi N., Sasano H. Intracrine mechanism of estrogen synthesis in breast cancer. *Biomed. Pharmacother.* 2003, 57, 460-462.
8. Subramanian A., Salhab M., Mokbel K. Oestrogen producing enzymes and mammary carcinogenesis: a review. *Breast Cancer Res. Treat.* 2008, 111, 191-202.
9. Maltais R., Poirier D. Steroid sulfatase inhibitors: a review covering the promising 2000-2010 decade. *Steroids.* 2011, 76, 929-948.
10. Ghosh D. Human sulfatases: a structural perspective to catalysis. *Cell Mol. Life Sci.* 2007, 64, 2013-2022.
11. Pasqualini J. R., Gelly C., Nguyen B. L., Vella C. Importance of estrogen sulfates in breast cancer. *J. Steroid Biochem.* 1989, 34, 155-163.
12. Chetrite G. S., Cortes-Prieto J., Philippe J. C., Wright F., Pasqualini J. R. Comparison of estrogen concentrations, estrone sulfatase and aromatase activities in normal, and in cancerous, human breast tissues. *J. Steroid Biochem. Mol. Biol.* 2000, 72, 23-27.
13. Pasqualini J. R., Chetrite G., Blacker C., Feinstein M. C., Delalonde L., Talbi M., Maloche C. Concentration of estrone, estradiol, and estrone sulfate and evaluation of sulfatase and aromatase activities in pre- and post-menopausal breast cancer patients. *J. Clin. Endocrinol. Metab.* 1996, 81, 1460-1464.
14. Santner S. J., Feil P. D., Santen R. J. In situ estrogen production via the estrone sulfatase pathway in breast tumors: relative importance versus the aromatase pathway. *J. Clin. Endocrinol. Metab.* 1984, 59, 29-33.
15. Imai Y., Nakamura T., Matsumoto T., Takaoka K., Kato S. Molecular mechanisms underlying the effects of sex steroids on bone and mineral metabolism. *J. Bone Miner. Metab.* 2009, 27, 127-130.
16. Ouellet E., Maltais R., Ouellet C., Poirier D. Investigation of dual-action steroid sulfatase inhibitors generated by parallel solid-phase synthesis. *Med. Chem. Commun.* 2013, 4, 681-692.
17. Huggins C., Hodges C. V. Studies on Prostatic Cancer. I. The Effect of Castration, of Estrogen and of Androgen Injection on Serum Phosphatases in Metastatic Carcinoma of the Prostate. *Cancer Res.* 1941, 1, 293-297.
18. Rasmussen G. H. Chapter 18. Chemical Control of Androgen Action. *Ann. Rep. Med. Chem.* 1986, 21, 179-188.
19. National Cancer Institute of Canada; *Canadian Cancer Statistics* 2012, Toronto, Canada, 2012.
20. Labrie F., Dupont A., Bélanger A. (1985) In: Important Advances in Oncology (De Vita V. T., Hellman S., Rosenbert S. A., eds), J.B. Lippincott, Philadelphia, pp. 193.
21. Labrie F., Cusan L., Gomez J., et al. Down-staging of early stage prostate cancer before radical prostatectomy: The first randomized trial of neoadjuvant combination therapy with flutamide and a luteinizing hormone-releasing hormone agonist. *Urology* 1994, 44, 29-37.
22. a) Labrie F. Intracrinology. *Mol. Cell. Endocrinol.* 1991, 78, C113-118; b) Labrie F., Bélanger A., Simard J. et al. DHEA and Peripheral Androgen and Estrogen Formation: Intracrinology. *N.Y. Academy of Sciences* 1995, 774, 16-28; c) Labrie F., Luu-The V., Labrie C., et al. Endocrine and Intracrine Sources of Androgens in Women: Inhibition of Breast Cancer and Other Roles of Androgens and Their Precursor Dehydroepiandrosterone. *Endocr. Rev.* 2003, 24, 152-182; d) Campos S. M. Aromatase Inhibitors for Breast Cancer in Postmenopausal Women. *The Oncologist* 2004, 9, 126-136.
23. Leuprolide Study Group. Leuprolide versus diethylstilbestrol for metastatic prostate cancer. *New Engl. J. Med.* 1984, 311, 1281-1286.
24. Nicholson R. I., Walker K. J., Turkes A., et al. Therapeutic significance and the mechanism of action of the LH-RH agonist ICI 118630 in breast and prostate cancer. *J. Steroid Biochem.* 1984, 20, 129-135.
25. de Bono J. S., Logothetis C. J., Molina A., et al Abiraterone and Increased Survival in Metastatic Prostate Cancer. *New Engl. J. Med.* 2011, 364, 1995-2005.
26. Parenti G., Meroni G., Ballabio A. The sulfatase gene family. *Curr. Opin. Gen. Develop.* 1997, 7, 386-391.
27. Stein C., Hille A., Seidel J., et al. Cloning and expression of human steroid-sulfatase. Membrane topology, glycosylation, and subcellular distribution in BHK-21 cells. *J. Biol. Chem.* 1989, 264, 13865-13872.
28. Purohit A., Dauvois S., Parker M. G., et al. The hydrolysis of oestrone sulphate and dehydroepiandrosterone sulphate by human steroid sulphatase expressed in transfected COS-1 cells. *J. Steroid Biochem. Molec. Biol.* 1994, 50, 101-104.
29. Ho S. M. Estrogens and anti-estrogens: Key mediators of prostate carcinogenesis and new therapeutic candidates. *J. Cell. Biochem.* 2004, 91, 491-503.
30. Bonkhoff H., Berges R. The Evolving Role of Oestrogens and Their Receptors in the Development and Progression of Prostate Cancer. *Eur. Urol.* 2009, 55, 533-542.
31. Kawashima H., Nakatani T. Involvement of estrogen receptors in prostatic diseases. *Int. J. Urol.* 2012, 19, 512-522.
32. Harrkonen P. L., Makela S. I. Role of estrogens in development of prostate cancer. *J. Steroid Biochem. Mol. Biol.* 2004, 92, 297-305.
33. Giton F., de la Taille A., Allory Y., et al. Estrone sulfate ($E_1S$), a prognosis marker for tumor aggressiveness in prostate cancer (PCa). *J. Steroid Biochem. Mol. Biol.* 2008, 109, 158-167.
34. Purohit A., Foster P. A. Steroid sulfatase inhibitors for estrogen- and androgen-dependent cancers. *J. Endocrinol.* 2012, 212, 99-110.
35. Hobisch A., Hittmair A., Daxenbichler G., et al. Metastatic lesions from prostate cancer do not express oestrogen and progesterone receptors. *J. Pathology* 1997, 182, 356-361.
36. Mosselman S., Polman J., Dijkema R. ERβ: Identification and characterization of a novel human estrogen receptor. *FEBS Lett.* 1996, 392, 49-53.
37. Byers M., Kuiper G. G. J. M., Gustafsson J. A., et al. Estrogen Receptor-β mRNA Expression in Rat Ovary: Down-Regulation by Gonadotropins. *Mol. Endocrinology* 1997, 11, 172-182.
38. Royuela M., de Miguel M. P., Bethencourt F. R., et al. Estrogen receptors alpha and beta in the normal, hyperplastic and carcinomatous human prostate. *J. Endocrinol.* 2001, 168, 447-454.
39. Lau K. M., LaSpina M., Long J., et al. Expression of Estrogen Receptor (ER)-α and ER-β in Normal and Malignant Prostatic Epithelial Cells: Regulation by Methylation and Involvement in Growth Regulation. *Cancer Res.* 2000, 60, 3175-3182.
40. Steiner M. S., Raghow S. Antiestrogens and selective estrogen receptor modulators reduce prostate cancer risk. *World J. Urol.* 2003, 21, 31-36.
41. Steiner M. S. Role of peptide growth factors in the prostate: a review. *Urology* 1993, 42, 99-110.

42. Steiner M. S. Review of Peptide Growth Factors in Benign Prostatic Hyperplasia and Urological Malignancy. *J. Urol.* 1995, 153, 1085-1096.
43. Lam H. Y. Tamoxifen is a calmodulin antagonist in the activation of cAMP phosphodiesterase. *Biochem. Biophys. Res. Comm.* 1984, 118, 27-32.
44. O'Brien C. A., Liskamp R. M., Solomon D. H. Inhibition of Protein Kinase C by Tamoxifen. *Cancer Res.* 1985, 45, 2462-2465.
45. Rohlff C., Blaogsklonny M. V., Kyle E., et al. Prostate cancer cell growth inhibition by tamoxifen is associated with inhibition of protein kinase C and induction of p21(waf1/cip1). *Prostate* 1998, 37, 51-59.
46. Setlur S. R., Mertz K. D., Hoshida Y. et al. Estrogen-Dependent Signaling in a Molecularly Distinct Subclass of Aggressive Prostate Cancer. *J. Natl. Cancer Inst.* 2008, 100, 815-825.
47. Briganti A. Oestrogens and Prostate Cancer: Novel Concepts About an Old Issue. *Eur. Urol.* 2009, 55, 543-545.
48. Nelles J., Hu W. Y., Prins G. S. Estrogen action and prostate cancer. *Expert Rev. Endocrionol. Metab.* 2011, 6, 437-451.
49. Pickar J. H., MacNeil T., Ohleth K. SERMs: Progress and future perspectives. *Maturitas* 2010, 67, 129-138.
50. Taneja S. S., Smith M. R., Dalton J. T., et al. Toremifene—a promising therapy for the prevention of prostate cancer and complications of androgen deprivation therapy. *Expert Opin. Investig. Drugs* 2006, 15, 293-305.
51. Price D., Stein B., Sieber P., et al. Toremifene for the Prevention of Prostate Cancer in Men With High Grade Prostatic Intraepithelial Neoplasia: Results of a Double-Blind, Placebo Controlled, Phase IIB Clinical Trial. *J. Urol.* 2006, 176, 965-970.
52. Nunez-Nateras R., Castle E. P. Effect of the simultaneous blockade of androgen and estrogen receptors on prostate cancer: Preliminary results. *J. Clin. Oncol.* 2011, 29, suppl 7: abstr 168.
53. Brawer M. K. Hormonal Therapy for Prostate Cancer. *Review in Urol.* 2006, 8, suppl. 2: S35-S47.
54. Smith M. R., Morton R. A., Barnette K. G., et al. Toremifene to Reduce Fracture Risk in Men Receiving Androgen Deprivation Therapy for Prostate Cancer. *J. Urol.* 2010, 184, 1316-1321.
55. Ciobanu L. C., Luu-The V., Martel C., Labrie F., Poirier D., Inhibition of Estrone Sulfate-induced Uterine Growth by Potent Nonestrogenic Steroidal Inhibitors of Steroid Sulfatase. *Cancer Res.,* 2003, 63, 6442-6446.
56. Ciobanu L. C., Poirier D. Synthesis of libraries of 16beta-aminopropyl estradiol derivatives for targeting two key steroidogenic enzymes. *Chem Med Chem.* 2006, 1, 1249-1259.
57. Ciobanu L. C., Maltais R., Poirier D. The sulfamate functional group as a new anchor for solid-phase organic synthesis. *Org. Lett.* 2000, 2, 445-448.
58. Poirier D., Ciobanu L. C., Berube M. A multidetachable sulfamate linker successfully used in a solid-phase strategy to generate libraries of sulfamate and phenol derivatives. *Bioorg. Med. Chem. Lett.* 2002, 12, 2833-2838.
59. Hernandez-Guzman F. G., Higashiyama T., Pangborn W., Osawa Y. Ghosh D. Structure of human estrone sulfatase suggests functional roles of membrane association. *J. Biol. Chem.* 2003, 278, 22989-22997.
60. Wang T., You Q., Huang F. S., Xiang H. Recent advances in selective estrogen receptor modulators for breast cancer. *Mini Rev. Med. Chem.* 2009, 9, 1191-1201.
61. Musa M., Omar M., Khan F., Cooperwood J. S. Medicinal chemistry and emerging strategies applied to the development of selective estrogen receptor modulators (SERMs). *Curr. Med. Chem.* 2007, 14, 1249-1261.
62. Tripathi R. P., Verma S. S., Pandey J., Tiwari V. K. Recent development on catalytic reductive amination and applications. *Curr. Org. Chem.* 2008, 12, 1093-1115.
63. Orimo H. The mechanism of mineralization and the role of alkaline phosphatase in health and disease. *J. Nippon Med. Sch.* 2010, 77, 4-12.
64. Qu Q., Perälä-Heape M., Kapanen A., Dahllund J., Salo J., Väänänen H. K., Härkönen P. Estrogen enhances differentiation of osteoblasts in mouse bone marrow culture. *Bone.* 1998, 22, 201-209.
65. Sun J., Huang Y. R., Harrington W. R., Sheng S., Katzenellenbogen J. A., Katzenellenbogen B. S. Antagonists selective for estrogen receptor alpha. *Endocrinology.* 2002, 143, 941-947.
66. Compton D. R., Sheng S., Carlson K. E., Rebacz N. A., Lee I. Y., Katzenellenbogen B. S., Katzenellenbogen J. A. Pyrazolo[1,5-a]pyrimidines: estrogen receptor ligands possessing estrogen receptor β antagonist activity. *J. Med. Chem.* 2004, 47, 5872-5893.
67. Cambridge Soft Chem 3D Pro (version 5.0), Cambridge Soft Corporation, Cambridge Mass., www.cambsoft.com.
68. PDB file ideal coordinates for 34 atoms from MSD-Chem, HIC-up files for compound ZTW raloxifene core (http://xray.bmc.uu.se/hicup/RAL/index.html), Hetero-Compounds Information Center, Uppsala, Department of Cell and Molecular Biology, Uppsala University.
69. Ciobanu L. C., Boivin R. P., Luu-The V., Poirier D. 3β-Sulfamate derivatives of C19 and C21 steroids bearing a t-butylbenzyl or a benzyl group: synthesis and evaluation as non-estrogenic and non-androgenic steroid sulfatase inhibitors. *J. Enzyme Inhib. Med. Chem.* 2003, 18, 15-26.
70. Boivin R. P., Luu-The V., Lachance R., Labrie F., Poirier D. Structure-activity relationship of 17α-derivatives of estradiol as inhibitors of steroid sulfatase. *J. Med. Chem.* 2000, 43, 4465-4478.
71. Wakeling A. E., Bowler J. Novel antioestrogens without partial agonist activity. *J. Steroid Biochem.* 1988, 31, 645-653.
72. Ciobanu L. C., Luu-The V., Poirier D. Nonsteroidal compounds designed to mimic potent steroid sulfatase inhibitors. *J. Steroid Biochem. Mol. Biol.* 2002, 80, 339-353.
73. Ciobanu L. C., Boivin R. P., Luu-The V., Labrie F., Poirier D. Potent inhibition of steroid sulfatase activity by 3-O-sulfamate 17alpha-benzyl (or 4'-tert-butylbenzyl)estra-1,3,5(10)-trienes: combination of two substituents at positions C3 and c17alpha of estradiol. *J. Med. Chem.* 1999, 42, 2280-2286.
74. Brooks S. C., Locke E. R., Soule H. D. Estrogen Receptor in a Human Cell Line (MCF-7) from Breast Carcinoma. *J. Biol. Chem.,* 1973, 248, 6251-6253.
75. Miki Y., Suzuki T., Hatori M., Igarashi K, Aisaki K. I., Kanno J., Nakamura Y., Uzuki M., Sawai T, Sasano H. Effects of aromatase inhibitors on human osteoblast and osteoblast-like cells: a possible androgenic bone protective effects induced by exemestane. *Bone,* 2007, 40, 876-887.
76. Peterson E. M., Brownell J, Vince R. Synthesis and biological evaluation of 5'-sulfamoylated purinyl carbocyclic nucleosides. *J. Med. Chem.,* 1992, 35, 3991-4000.
77. Laplante Y., Cadot C., Fournier M. A., Poirier D. Estradiol and estrone C-16 derivatives as inhibitors of type 1 17beta-hydroxysteroid dehydrogenase: blocking of ER+ breast cancer cell proliferation induced by estrone. *Bioorg. Med. Chem.,* 2008, 16, 1849-1860.

78. a) Roy J., Lefebvre J., Maltais R., Poirier D. *Mol. Cell. Endocrinol.* 2013, 176, 148-155; b) Poirier D., Roy J., Lefèbvre J., et al. (2011) A potent steroid sulfatase inhibitor blocks the DHEAS-stimulated growth of androgen-sensitive tissues and human prostate cancer xenografts (LNCaP cells) in nude mice. *Congress on Steroid Research.* Chicago Mich., March 27-29. P. 2-46.

79. Colette S., Defrère S., Lousse J. C., Langendonckt A. V., Gotteland J. P., Loumaye E., Donnez J. Inhibition of steroid sulfatase decreases endometriosis in a in vivo murine model. *Hum. Reprod.* 2011, 26, 1362-1370.

80. Saito T., Yoshizawa M., Yamauchi Y., Kinoshita S., Fujii T., Mieda M., Sone H., Yamamoto Y., Koizumi N. Effects of the novel orally active antiestrogen TZE-5323 on experimental endometriosis. *Arzneimittelforschung.* 2003, 53, 507-514.

The invention claimed is:

1. A compound of formula A or A' below, or a pharmaceutically acceptable salt thereof, or a solvate or hydrate thereof,

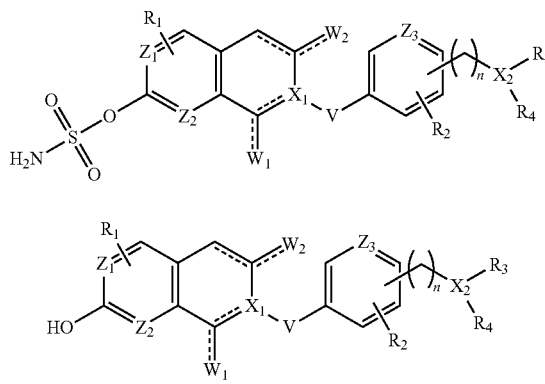

wherein:
$X_1$ is N, and $X_2$ is C, CH or N;
$R_3$ and $R_4$ are each independently H or a $C_1$-$C_{30}$ saturated or unsaturated chemical group that optionally includes at least one heteroatom selected from O, S, F, Cl, Br and I, optionally the group includes at least one $C_5$-$C_8$ carbocycle or heterocycle which is fused or unfused, optionally $R_3$ and $R_4$ together with the C atom or N atom to which they are attached form a $C_5$-$C_8$ carbocycle or heterocycle which is fused or unfused, the $C_5$-$C_8$ cycle optionally containing at least one heteroatom selected from O, S, F, Cl, Br and I and being substituted with at least one of $R_1$ and $R_2$ as defined below;
V is C=O, C=S or $CH_2$;
$R_1$ and $R_2$ are each independently H, a $C_1$-$C_6$ alkyl, a $C_1$-$C_6$ aryl, a $C_1$-$C_{12}$ alkylaryl, phenyl, a $C_1$-$C_6$ alkoxy, a $C_1$-$C_6$ thioalkoxy, F, Cl, Br or I;
n is an integer from 1 to 12;
$Z_1$ and $Z_2$ are each CH, $Z_3$ is CH or N; and
$W_1$ and $W_2$ are each independently H, $CH_2$, O or S.

2. A compound according to claim 1, which is of formula B or B' below,

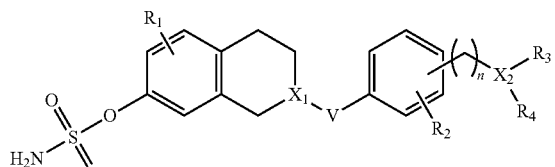

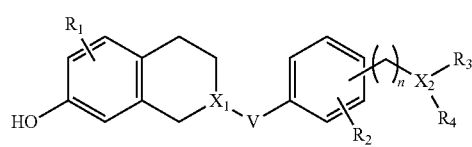

wherein $X_1$, $X_2$, $R_1$ to $R_4$, V and n are as defined in claim 1.

3. A compound according to claim 1, which is of formula C or C' below,

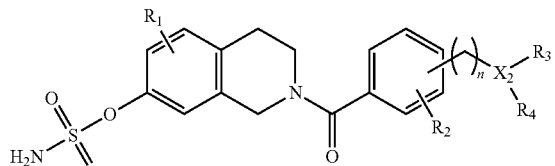

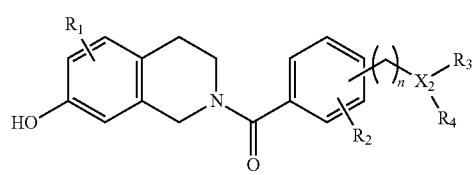

wherein $X_2$, $R_1$ to $R_4$ and n are as defined in claim 1.

4. A compound according to claim 1, which is of formula D or D' below,

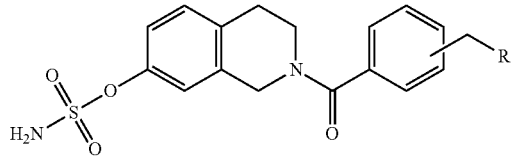

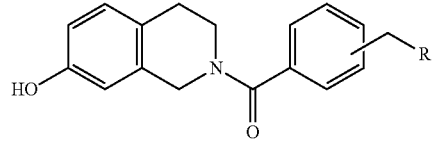

wherein R is —N(CH$_2$)$_{m1}$R$_5$(CH$_2$)$_{m2}$R$_6$, m1 and m2 being each independently an integer from 1 to 12; and $R_6$ and $R_6$ being each independently a $C_1$-$C_{30}$ saturated or unsaturated chemical group that optionally includes at least one heteroatom selected from O, S, F, Cl, Br and I, optionally the group includes at least one $C_5$-$C_8$ cycle which is optionally substituted.

5. A compound according to claim 1, which is of formula D or D' below,

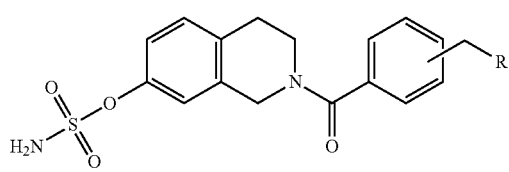
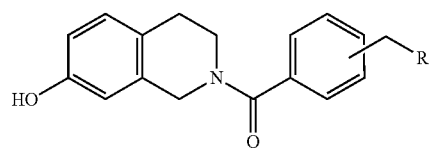
wherein R is selected from:
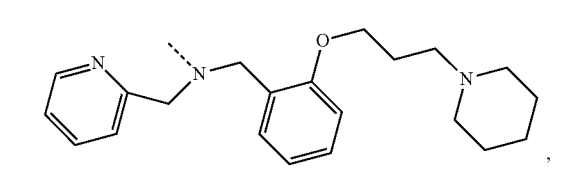
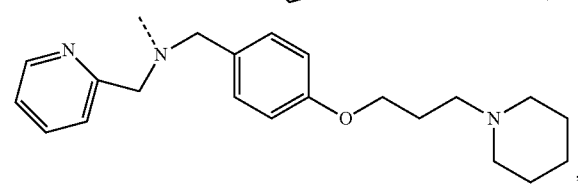
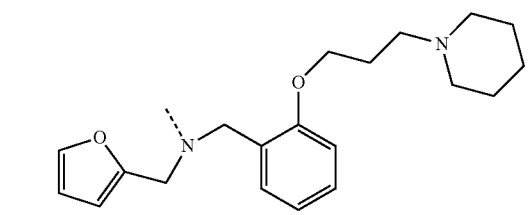
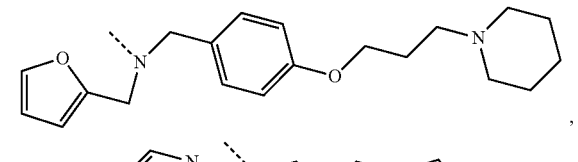
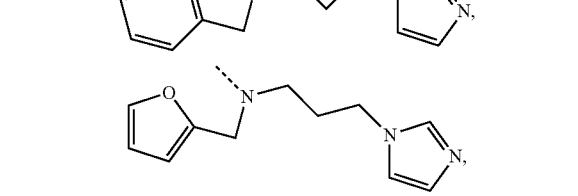
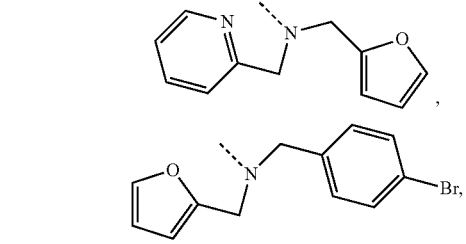
-continued
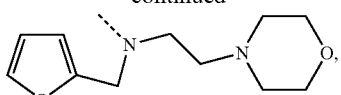
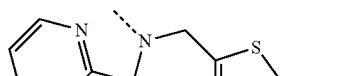
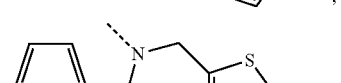
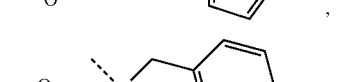
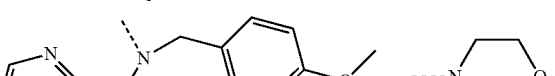
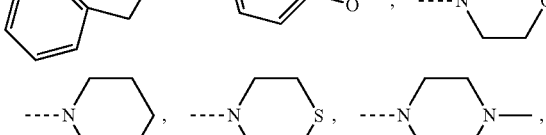
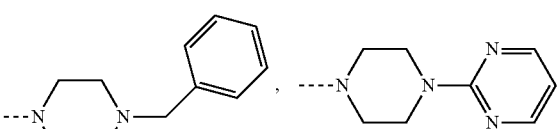
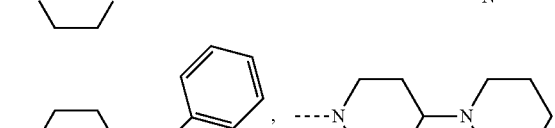
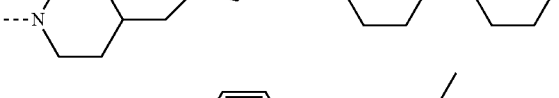
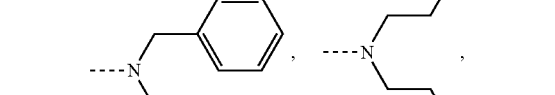
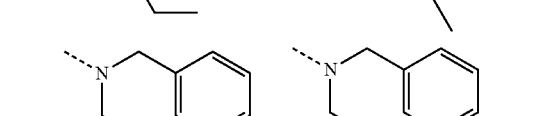
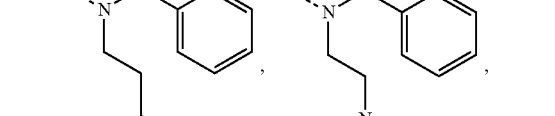
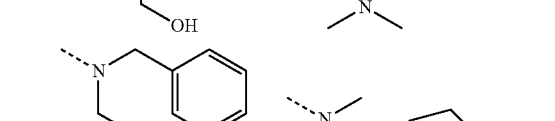
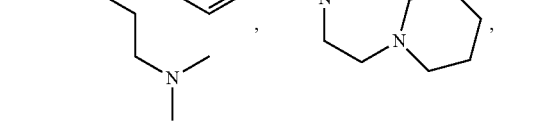

-continued

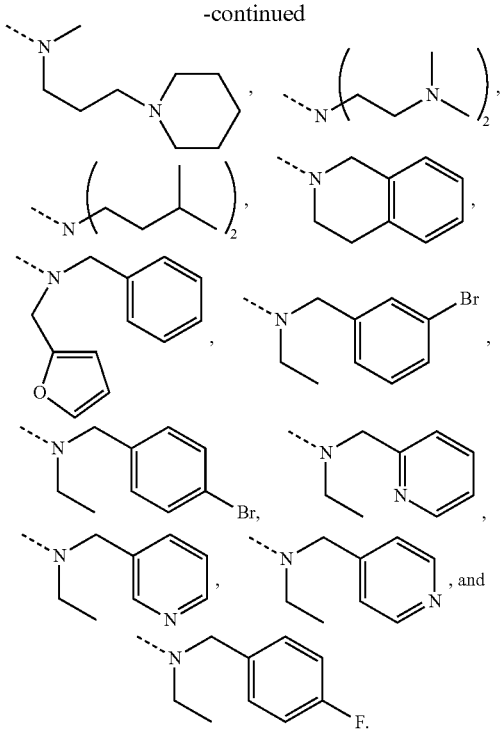

6. A compound according to claim 1, which is of formula D or D' below,

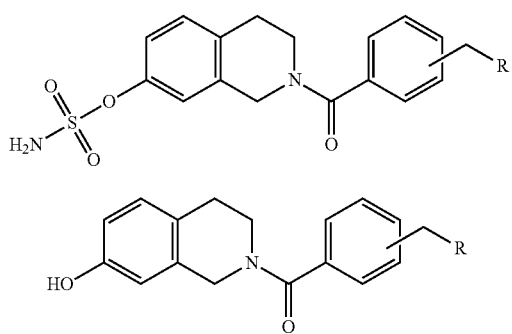

wherein R is selected from:

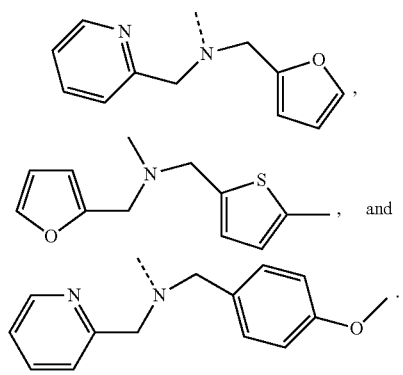

7. A pharmaceutical composition comprising a compound as defined in claim 1, and a pharmaceutically acceptable carrier.

8. A method of concurrently inhibiting steroid sulfatase (STS) activity and inducing selective estrogen receptor modulator (SERM) effects, in a subject in need thereof, the method comprising administering to the subject a therapeutically effective amount of a compound as defined in claim 1.

9. A method of concurrently inhibiting steroid sulfatase (STS) activity, and performing at least one of:
  inducing selective estrogen receptor modulator (SERM) effects;
  increasing alkaline phosphatase (ALP) activity;
  selectively blocking activation of estrogen receptor in a first group of cells while stimulating estrogen receptor in a second group of cells;
  selectively blocking activation of estrogen receptor in a first group of cells while stimulating estrogen receptor in a second group of cells, and increasing alkaline phosphatase (ALP) activity in the second group of cells,
in a subject in need thereof, the method comprising administering to the subject a therapeutically effective amount of a compound as defined in claim 1.

10. A method of:
  selectively blocking activation of estrogen receptor in a first group of cells while stimulating estrogen receptor in a second group of cells; or
  blocking activation of estrogen receptor in a first group of cells, stimulating estrogen receptor in a second group of cells, and increasing alkaline phosphatase (ALP) activity in the second group of cells,
in subject in need thereof, the method comprising administering to the subject a therapeutically effective amount of a compound as defined in claim 1.

11. A method according to claim 9, wherein the cells of the first group are breast cells or prostate cells, and the cells of the second group are bone cells.

12. A method of concurrently inhibiting steroid sulfatase (STS) activity and inducing selective estrogen receptor modulator (SERM) effects, in cells, the method comprising contacting the cells with a compound as defined in claim 1, and the method being performed in vitro.

13. A method of concurrently inhibiting steroid sulfatase (STS) activity and performing at least one of:
  inducing selective estrogen receptor modulator (SERM) effects;
  increasing alkaline phosphatase (ALP) activity;
  selectively blocking activation of estrogen receptor in a first group of cells while stimulating estrogen receptor in a second group of cells;
  selectively blocking activation of estrogen receptor in a first group of cells while stimulating estrogen receptor in a second group of cells, and increasing alkaline phosphatase (ALP) activity in the second group of cells,
the method comprising contacting the cells with of a compound as defined in claim 1, and the method being performed in vitro.

14. A method of:
  selectively blocking activation of estrogen receptor in a first group of cells and stimulating estrogen receptor in a second group of cells or
  selectively blocking activation of estrogen receptor in a first group of cells, stimulating estrogen receptor in a second group of cells, and increasing alkaline phosphatase (ALP) activity in the second group of cells, the method comprising contacting the cells with a compound as defined in claim 1, and the method being performed in vitro.

\* \* \* \* \*